US011353458B2

(12) United States Patent
Bounds et al.

(10) Patent No.: US 11,353,458 B2
(45) Date of Patent: Jun. 7, 2022

(54) PROGNOSTIC METHOD

(71) Applicant: GlaxoSmithKline Intellectual Property Development Limited, Middlesex (GB)

(72) Inventors: Danton Bounds, London (GB); Jenny L. Craigen, Stevenage (GB); William E. Fieles, Collegeville, PA (US); Fiona M. Germaschewski, Stevenage (GB); Gaelle Herledan, London (GB); Lydia Lee, London (GB); Patrick A. Mayes, Collegeville, PA (US); Lee McCahon, Stevenage (GB); Katherine (Nee Sully) Nevin, Stevenage (GB); Jennifer Paterson, London (GB); Manuel Rodriguez-Justo, London (GB); Laura M. Seestaller-Wehr, Collegeville, PA (US); James Tunstead, Collegeville, PA (US); Kwee L. Yong, London (GB)

(73) Assignee: GlaxoSmithKline Intellectual Property Development Limited, Brentford (GB)

( * ) Notice: Subject to any disclaimer, the term of this patent is extended or adjusted under 35 U.S.C. 154(b) by 362 days.

(21) Appl. No.: 15/771,622

(22) PCT Filed: Oct. 28, 2016

(86) PCT No.: PCT/IB2016/056511
§ 371 (c)(1),
(2) Date: Apr. 27, 2018

(87) PCT Pub. No.: WO2017/072716
PCT Pub. Date: May 4, 2017

(65) Prior Publication Data
US 2018/0306791 A1 Oct. 25, 2018

Related U.S. Application Data

(60) Provisional application No. 62/248,595, filed on Oct. 30, 2015, provisional application No. 62/261,957, filed on Dec. 2, 2015.

(51) Int. Cl.
| G01N 33/574 | (2006.01) |
| A61K 39/395 | (2006.01) |
| G01N 15/14 | (2006.01) |
| A61P 35/00 | (2006.01) |
| C07K 16/28 | (2006.01) |
| G01N 33/50 | (2006.01) |
| A61K 39/00 | (2006.01) |

(52) U.S. Cl.
CPC ........ G01N 33/57407 (2013.01); A61P 35/00 (2018.01); C07K 16/2878 (2013.01); G01N 15/14 (2013.01); G01N 33/5091 (2013.01); *A61K 39/395* (2013.01); *A61K 2039/505* (2013.01); *G01N 2333/70578* (2013.01); *G01N 2800/52* (2013.01)

(58) Field of Classification Search
CPC .. C07K 16/2878; A61K 39/395; G01N 15/14; G01N 2333/70578; G01N 2800/52
See application file for complete search history.

(56) References Cited

U.S. PATENT DOCUMENTS

| 2013/0101599 A1* | 4/2013 | Borges | C07K 16/2803 424/158.1 |
| 2014/0161828 A1* | 6/2014 | Armitage | A61K 39/3955 424/181.1 |

FOREIGN PATENT DOCUMENTS

| WO | WO-2012163805 A1 * | 12/2012 | ......... A61K 47/6849 |
| WO | WO-2013119990 A2 * | 8/2013 | ......... A61K 47/6849 |
| WO | WO 2014/124280 A1 | 8/2014 | |

OTHER PUBLICATIONS

Ghermezi et al., Blood, 2014, 124(21): 3405.*
Paul, Fundamental Immunology, 3rd Edition, 1993, pp. 292-295.*
Rudikoff et al., Proc. Natl. Acad. Sci. USA, 1982, 79(6):1979-1983.*
D'Costa et al., Blood, 2009, 113:5911-5919.*
Yong et al.,Evaluation of Bcma as a Therapeutic Target in Multiple Myeloma Using an Antibody-Drug Conjugate Blood, 2013, 122(21):4447, 3 pages.*
Berenson et al., "Serum B-Cell Maturation Antigen is a Novel Prognostic Indicator for Multiple Myeloma Patients and Correlates with Clinical Status and Survival", *Haematologica*, vol. 100, No. s1, pp. 93-94 (2015).
Ghermezi et al., "Serum B-Cell Maturation Antigen is a Novel Prognostic Indicator for Multiple Myeloma Patients and Correlates with Clinical Status and Survival", *Blood*, vol. 124, No. 21, p. 3405, abstract (2014).
Lee et al., "Evaluation of B cell maturation antigen as a target for antibody drug conjugate mediated cytotoxicity in multiple myeloma", *British Journal of Haematology*, vol. 174, No. 6, pp. 911-922 (2016).

(Continued)

*Primary Examiner* — Hong Sang
(74) *Attorney, Agent, or Firm* — Banner & Witcoff, Ltd.

(57) ABSTRACT

Methods are provided for determining prognosis of multiple myeloma in a patient by measuring expression of BCMA in a sample. Also provided are methods for treating multiple myeloma by measuring expression of BCMA in a sample and administering an effective amount of an antigen binding protein that binds BCMA. Also provided are kits for measuring BCMA expression in a sample.

8 Claims, 27 Drawing Sheets
Specification includes a Sequence Listing.

(56) References Cited

OTHER PUBLICATIONS

Sanchez et al., "Serum B-cell maturation antigen is elevated in multiple myeloma and correlates with disease status and survival", *British Journal of Haematology*, vol. 158, No. 6, pp. 727-738 (2012).
Yong, et al., "Evaluation of Bcma as a Therapeutic Target in Multiple Myeloma Using an Antibody-Drug Conjugate—the Myeloma Beacon, Abstract 4447 (Poster Presentation)", *652 Myeloma: Pathophysiology and Pre-Clinical Studies, Excluding Therapy*, vol. 3, p. 1, abstract (2013).

\* cited by examiner

| | | |
|---|---|---|
| TOTAL PATIENTS n | | 70 |
| BCMA EXPRESSION BY FLOW n | | 64 |
| BCMA EXPRESSION BY IHC n | | 64 |
| BCMA EXPRESSION BY FLOW & IHC n | | 58 |
| BCMA EXPRESSION BY FLOW MEDIAN MFI RATIO, RANGE | | 4.1, 1.0-67 |
| BCMA EXPRESSION BY IHC MEDIAN BCMA/BLIMP1 SCORE, RANGE | | 2, 1-5 |
| AGE MEDIAN, RANGE | | 64, 28-83 |
| SEX n(%) | M | 49(70%) |
| | F | 21(30%) |
| DISEASE STATE n(%) | D | 22(31.4%) |
| | R/RD | 47(67.1%) |
| | NA | 1(1.4%) |
| CYTOGENETIC RISK n(%) | STANDARD | 27(38.6%) |
| | POOR | 40(57.1%) |
| | NA | 3(4.3%) |
| ISOTYPE n(%) | IgG | 42(60%) |
| | IgA | 15(21.4%) |
| | IgD & LC | 11(15.7%) |
| | NA | 2(2.9%) |
| FOLLOWUP MEDIAN MONTHS, RANGE | | 24, 1-38 |
| RESPONSE TO TREATMENT n(%) | CR/PR | 34(48.6%) |
| | LESS THAN PR | 32(45.7%) |
| | NA | 4(5.7%) |
| PFS MEDIAN MONTHS | | 12 |
| OS MEDIAN MONTHS | | NR |

FIG. 10A

PROGNOSTIC METHOD

RELATED APPLICATIONS

This application is a § 371 application of International Application No. PCT/IB2016/056511, filed 28 Oct. 2016, which claims the benefit of U.S. Provisional Application No. 62/248,595, filed 30 Oct. 2015 and U.S. Provisional Application No. 62/261,957, filed 2 Dec. 2015, the disclosures of which are incorporated herein in their entireties.

TECHNICAL FIELD

The present invention relates to the use of BCMA expression levels in the prognosis and treatment of BCMA-associated disorders.

BACKGROUND

BCMA (CD269 or TNFRSF17) is a member of the TNF receptor superfamily. It is an integral membrane receptor for the ligands BAFF and APRIL. BCMA's ligands can also bind additional receptors: TACI (Transmembrane Activator and Calcium modulator and cyclophilin ligand Interactor), which binds APRIL and BAFF; as well as BAFF-R (BAFF Receptor or BR3), which shows restricted but high affinity for BAFF. Together, these receptors and their corresponding ligands regulate different aspects of humoral immunity, B-cell development and homeostasis.

BCMA's expression is typically restricted to the B-cell lineage and is reported to increase in terminal B-cell differentiation. BCMA is expressed by human plasma blasts, plasma cells from tonsils, spleen and bone marrow, but also by tonsillar memory B cells and by germinal centre B cells, which have a TACI-BAFFR low phenotype (Darce et al., 2007). BCMA is virtually absent on naïve and memory B-cells (Novak et al., 2004). The BCMA antigen is expressed on the cell surface so is accessible to the antibody, but is also expressed in the golgi. As suggested by its expression profile, BCMA signalling, typically linked with B-cell survival and proliferation, is important in the late stages of B-cell differentiation, as well as the survival of long lived bone marrow plasma cells (O'Connor et al., 2004) and plasmablasts (Avery et al., 2003). Furthermore, as BCMA binds APRIL with high affinity, the BCMA-APRIL signalling axis is suggested to predominate at the later stages of B-cell differentiation, perhaps being the most physiologically relevant interaction.

Multiple myeloma (MM) is a cancer characterized by the accumulation of malignant plasma cells in the bone marrow (BM), and is the second most common haematological malignancy in the UK. Proteasome inhibitors and immune-modulatory drugs (IMiDs) have improved the outlook for many patients, however disease relapse is inevitable and the majority will die of their cancer (Kumar et al., 2012; Kumar et al., 2008). Thus new therapies are urgently needed but their development is hampered by the clinical and genetic heterogeneity of this disease. Surface receptors with restricted expression on plasma cells are attractive targets for immune-based therapies (Danylesko et al., 2012). BCMA mRNA is not expressed in non-haemopoietic tissue nor is BCMA present on naïve B cells, but is upregulated during B-cell differentiation into plasmablasts and BM plasma cells (PC) (Laabi et al., 1994; Laabi et al., 1992). BCMA also appears to be essential for the survival of BM PC, as BCMA$^{-/-}$ animals have reduced survival of these cells but otherwise a normal phenotype (O'Connor et al., 2004). Moreover, it has previously been shown that APRIL induces proliferation in primary MM cells (Quinn et al., 2011) and immunohistochemistry confirms that APRIL is present in the MM marrow microenvironment, where it is produced by myeloid cells (Belnoue et al., 2012; Matthes et al., 2011). Thus BCMA is a good potential target for therapeutic strategies not only because of its restricted expression on PC, but because of its role in the survival and growth of MM cells.

BCMA expression (both transcript and protein) is reported to correlate with disease progression in MM. Using Affymetrix microarrays, it was demonstrated that the TACI and BCMA genes were over-expressed in Multiple Myeloma Cells (MMC) compared with their normal counterparts (Moreaux et al., 2004). Gene expression analysis has been used to compare human myeloma cells with purified plasma cells from patients with MGUS and from normal bone marrow as well as with primary tumour cells from B-cell lineage leukaemias (Bellucci et al., 2005). The BCMA gene was highly expressed in all myeloma samples. Although purified plasma cells from patients with MGUS had lower expression of BCMA, there was no significant difference when compared with the expression found in normal plasma cells or myeloma cells. In contrast, BCMA expression was significantly lower in B-cell Chronic Lymphocytic Leukaemia (CLL), pre-B Acute Lymphocytic Leukaemia (ALL) and T-cell ALL (T-ALL).

Mouse models that transgenically over-express BAFF or APRIL have a significant increase in B-cell lymphomas (Batten et al., 2004—BAFF; Planelles et al., 2004—APRIL). In humans, excess BAFF and APRIL have been detected in the sera and micro-environments of patients with a number of B-cell malignancies, as well as other B-cell disorders.

However, there is still a need in the art to determine the prognosis of a patient with Multiple myeloma in order for the appropriate course of treatment to be chosen.

SUMMARY OF THE INVENTION

The inventors have found that high BCMA levels were associated with poorer outcomes and have identified a subgroup of patients with standard risk genetics who have earlier relapse and shorter survival. This contribution allows the prognosis of a subset of patients so that they can be identified for a more aggressive treatment regimen.

A first aspect of the invention provides a method for determining prognosis of multiple myeloma in a subject comprising the steps of:
 (a) obtaining a sample from said subject; and
 (b) testing the sample for the level of BCMA expression;
wherein, if the subject has a high level of BCMA expression, then the prognosis of multiple myeloma in the subject is poor.

A further aspect of the invention provides an antigen binding protein that specifically binds to BCMA for use in the treatment of multiple myeloma in a subject classified with poor prognosis, wherein said subject is characterised by a high level of BCMA expression in a sample from the subject.

A further aspect of the invention provides a method of treating multiple myeloma in a subject, comprising administering a therapeutically effective amount of an antigen binding protein which specifically binds to BCMA to a subject, wherein said subject has a high level of BCMA expression.

A further aspect of the invention provides a method of treating multiple myeloma in a subject with a high level of BCMA expression calculated according to the method as defined herein.

A further aspect of the invention provides a method of treating multiple myeloma in a subject with an antigen binding protein that specifically binds to BCMA in a human identified as suitable for said treatment, wherein said human is identified as suitable for said treatment:
 (a) by a high level of BCMA expression; or
 (b) using the method as defined herein.

According to another aspect of the invention, there is provided a method of treating multiple myeloma in a subject, comprising:
 (a) identifying a subject having a high level of BCMA expression; and
 (b) administering to the subject a therapeutically effective amount of the antigen binding protein described herein.

In a further aspect of the invention, there is provided a method of treating multiple myeloma in a subject comprising the steps of:
 (a) obtaining a sample from a subject;
 (b) determining the level of BCMA expression in the sample; and
 (c) if the level of BCMA expression is high, administering a therapeutically effective amount of the antigen binding protein described herein.

According to a further aspect of the invention, there is provided a kit for determining prognosis of a subject, the kit comprising reagents for measuring expression levels of BCMA in a sample. In yet another aspect, the invention provides a kit for determining BCMA expression in a subject, the kit comprising reagents for measuring expression levels of BCMA in a sample.

Figure 1A:
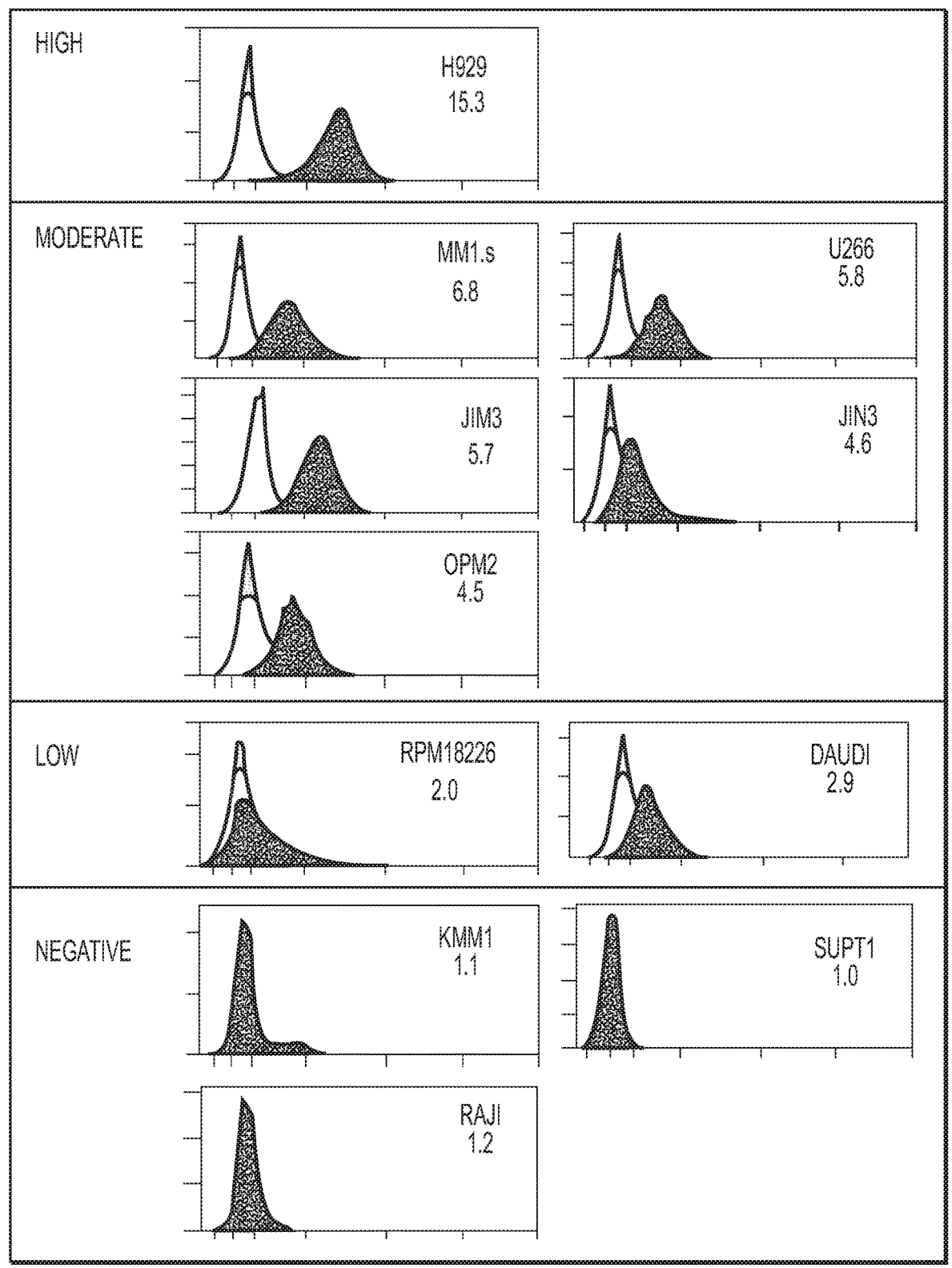
FIG. 1: BCMA expression by flow cytometry. (A) HMCL (H929, MM1.s, U266, JIM3, JJN3, OPM2, RPMI8226, KMM1) and human non-MM cell lines (SUPT1, Raji and Daudi) were incubated with isotype control IgG2a-488 (open histograms) or anti-BCMA S307118G03-488 (filled histograms). Numbers indicate ratio of mean fluorescence intensity (MFIr) of BCMA stained to isotype control stained cells. (B) Primary MM cells in BM MNCs from myeloma patients were identified by staining with CD138-APC, and specific staining for BCMA determined using anti-BCMA S307118G03-488 (filled histograms), control samples were incubated with IgG2a-488 (open histograms). Histograms of CD138+ gated population, MFIr indicated. (C) BCMA expression of patient samples by flow cytometry with J6M0-wtFc PE showing MFIr for individual patients (range: 1-67). (D) Primary myeloma cells were identified by staining for CD138, and co-stained with anti BCMA antibody J6M0-wtFc PE. Quantification of antibodies bound per cell (ABC) was done using BD Quantibrite beads. (range 348.7-4268.4 ABC, mean: 1181 ABC, median: 1084.9 ABC).

CD138 in BM and the BCMA/BLIMP1 score (n=40, $r^2$=0.37, p<0.0001 by Spearman rank correlation).

FIG. 10: Clinical correlation of BCMA expression. (A) Summary of clinical characteristics of patient cohort. D Diagnosis, R relapse, RD refractory disease, LC light chain, PFS progression free survival, OS overall survival, CR complete response PR partial response, NA not available or not applicable. (B) (i) PFS and (ii) OS according to BCMA/BLIMP1 score. NR, not reached. (C) (i) PFS and (ii) OS according to cytogenetic risk. (D) (i) PFS and (ii) OS according to cytogenetic risk and BCMA expression.

FIG. 11: Kinetics of surface BCMA internalization and re-expression following antibody binding. (A) H929 cells were pulsed with J6M0-MMAF at T=0 for 15 minutes, washed and incubated at 37° C. At specific time points, aliquots of cells were removed, and stained with anti-Fc to assess surface bound anti-BCMA. Twenty-four hours after the first pulse (T=24), cells were re-pulsed with J6M0-MMAF, and surface bound antibody monitored as before. (B) H929 cells were exposed to increasing doses of J6M0 in a 15 minute pulse and wash off, and surface bound antibody monitored overtime. (C) Cells were pulsed with murine anti-BCMA antibody (S336105A07), for 15 minutes, washed, fixed, incubated with anti-mouse Alexa 488 (green) and visualized immediately by confocal microscopy (i). Further aliquots of cells were pulsed with murine anti BCMA as before, washed, incubated at 37° C. and re-pulsed with J6M0 at 1 hour (ii-iv) or 7 hours (v-vii). After washing, cells were permeabilized and incubated with rabbit anti-EEA1. Finally, incubation with anti-mouse Alexa 488 (green) revealed surface BCMA labeled with first antibody pulse at T=0, anti-human Alexa 568 (red) indicated newly expressed BCMA detected with second pulse at T=1 hr or T=7 hrs, and anti-rabbit Alexa 633 (blue) detected EEA in endosomes. Images ii-vii are dual overlays of signal from these 3 antibodies. Images ii and v: first anti-BCMA pulse and anti EEA; iii and vi: second anti-BCMA pulse and anti EEA; iv and vii: first and second anti BCMA pulses. (D) H929 cells were treated with a 15 minute pulse (Washout) of 10 μg/ml murine anti-BCMA (S307118G03), washed and stained with anti-mouse antibody to assess surface BCMA expression. An aliquot of cells was then incubated at 37° C. in the absence, or presence of cycloheximide for 6 hours, then washed and incubated with anti-mouse antibody, or with J6M0 (to reveal newly expressed surface BCMA), followed by goat anti-human antibody. The second pulse with human anti-BCMA antibody reveals increased BCMA staining that is reduced by cycloheximide by ~25%. It therefore appears that about 25% of the BCMA receptor re-expression observed after a $2^{nd}$ pulse of anti BCMA is due to de novo synthesis of the receptor. The first 2 bars are controls (unstained and stained with isotype antibody respectively).

FIG. 12: Cytotoxicity of J6M0-MMAF on cell lines. (A) Non-transduced (NT), low BCMA-transduced (Low), and high BCMA-transduced (High) ARH77 cells were incubated with J6M0-MMAF at four concentrations (0.01, 0.02, 0.05 and 0.1 μg/mL), and analysed by AnnexinV/PI staining and flow cytometry after 3 days. Inset figures show flow cytometry overlays of each batch of cells stained with S307118G03 (black) or isotype control (white) and MFIr. Mean±SEM of 3 experiments. (B) Cell lines with high (H929), moderate (OPM2), low (KMM1) and negative (SUPT1, Raji) expression of BCMA were incubated with J6M0-MMAF and analysed as above for viable cells at two time points. Top panel shows live cells after 4 days showing dose dependent killing. Bottom panel shows live cells following incubation with J6M0-MMAF at 1 μg/mL on day 2 and 4. Mean±SEM, n=3 for both. (C) MM1.s cells were incubated with J6M0-MMAF at 0.2 μg/ml for 2 days in the presence of medium only, Rituximab (anti-CD20), or S307118G03 (anti-BCMA), and viable cells enumerated as above. Mean±SEM (n=3). (D) HMCL were cultured with J6M0-MMAF for 2 days and viability of bulk and progenitor populations compared. Progenitors were enumerated by performing clonogenic assays on aliquots of MNCs, removed after 2 days exposure to drug. CFC, colony-forming cell.

Figure 13:
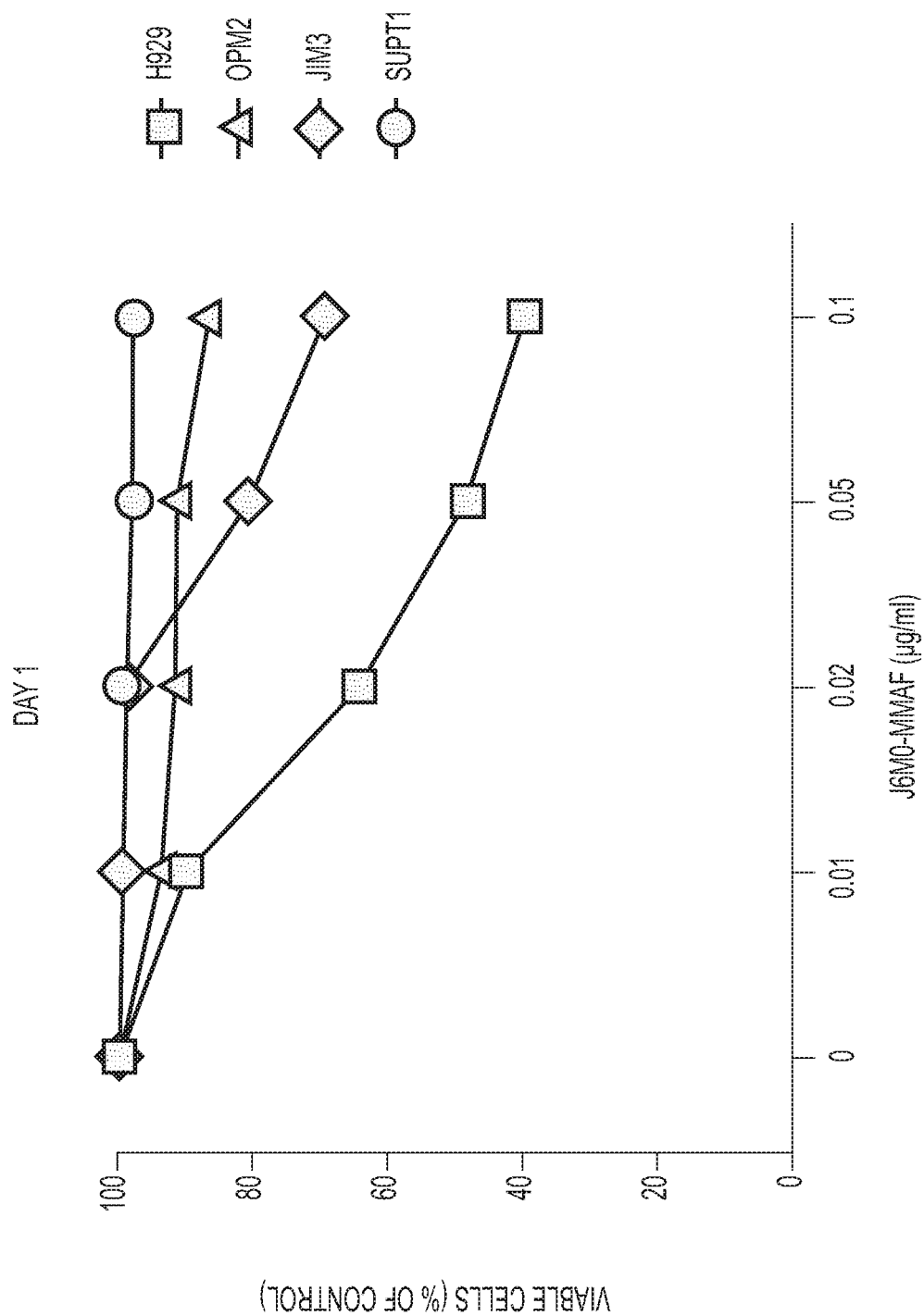

FIG. 13: J6M0-MMAF mediated cytotoxicity at Day 1 with cell lines. Percentage viability at 24 hours when cell lines with high (H929), moderate (OPM2, JIM3), and negative (SUPT1) expression of BCMA were incubated with 0.1 μg/ml J6M0-MMAF and analysed by flow cytometry. Data are normalized to control cultures, mean of 2.

FIG. 14: J6M0-MMAF activity on primary CD138+ cells. (A) BM MNCs from one representative patient (GSK 087) with moderate BCMA expression incubated with J6M0-MMAF. Viable CD138+ cells (percentage of control) after 2 and 6 days (left panel) obtained by analyzing CD138+ cells by flow cytometry and gating CD138+ fraction (middle panel) onto AnnexinV/PI dot-plot (right panel). (B) Four representative experiments showing viable CD138+ cells after culture of BM MNCs from myeloma patients with concentrations of J6M0-MMAF at varying time points. For each patient, histogram showing binding of J6M0-wtFc PE to CD138+ cells (black) compared to cells pre-incubated with Fc block as control (white) and where available IHC staining with MIB1 (pink, nuclear) and CD138 (membrane, brown) as a measure of plasma cell proliferation.

Figure 15:
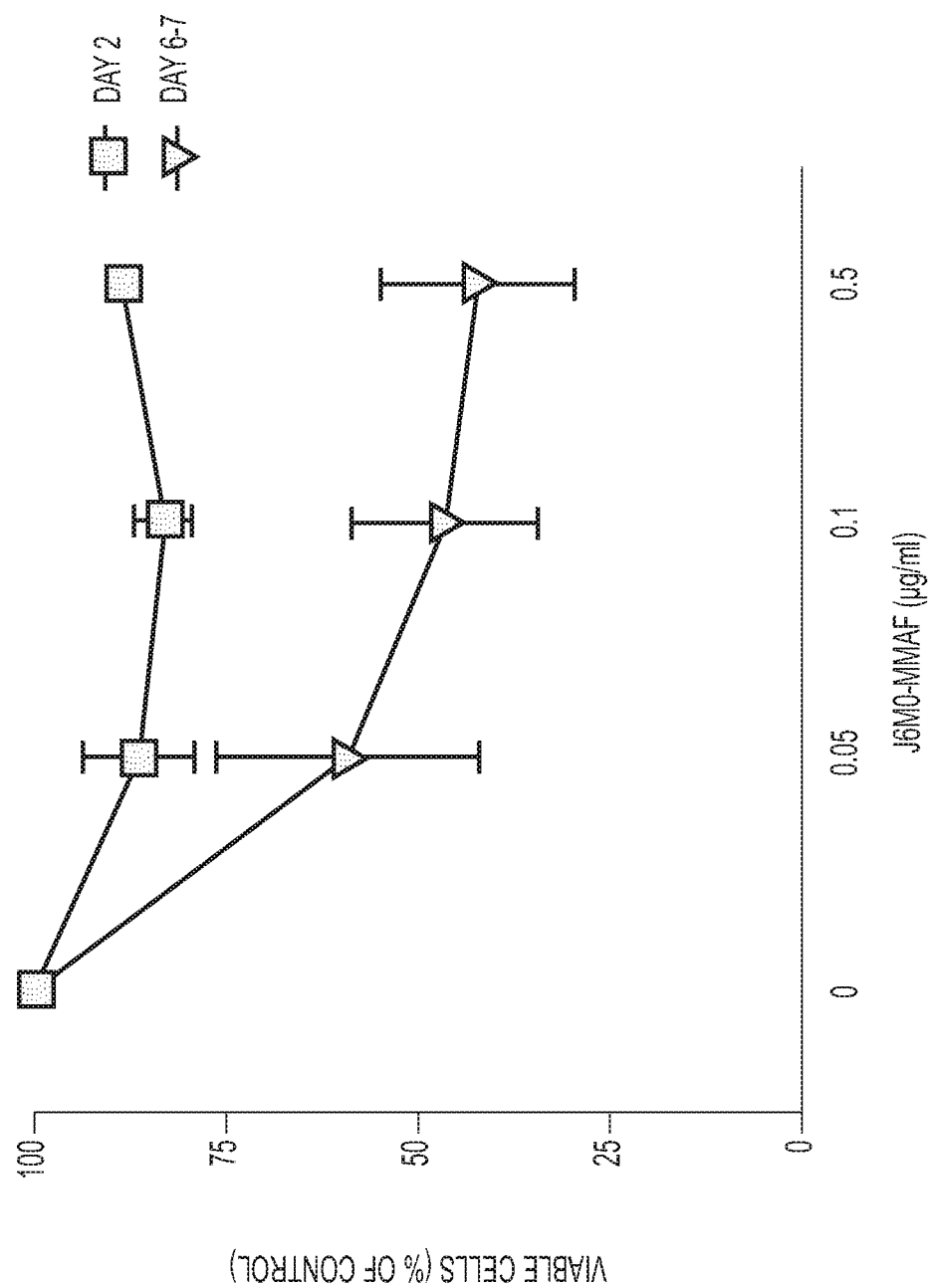

FIG. 15: Viability of primary myeloma cells on incubation with J6M0-MMAF. Patient BM MNCs were incubated with varying concentrations of J6M0-MMAF. Mean±SEM (n=3).

DETAILED DESCRIPTION

Methods of Prognosis

The inventors have surprisingly found that high BCMA levels in patients were associated with poorer outcomes and have identified a subgroup of patients with standard risk genetics who have earlier relapse and shorter survival. This discovery allows the prognosis of this subset of patients so that they can be identified for a more aggressive treatment regimen.

Accordingly, the invention provides a method for the prognosis of multiple myeloma in a subject comprising the steps of:

(a) obtaining a sample from said subject; and (b) testing the sample for the level of BCMA expression;

wherein, if the subject has a high level of BCMA expression, then the prognosis of multiple myeloma in the subject is poor.

In one aspect, the poor prognosis is at least one of: an increase in recurrence/relapse risk, a decrease in the likelihood of survival, a decrease in the time of survival, or an increase in the risk of metastasis. In one aspect, the poor prognosis is early relapse (such as 6 months) or shorter survival (such as 18 months).

In another aspect, the level of BCMA expression is determined using flow cytometry. For example, as shown by the Examples described herein, BCMA expression can be determined using the mean fluorescence obtained using flow cytometry with an anti-BCMA antibody and comparing it to a control (e.g., an isotype control). Such a calculation can determine the mean fluorescence intensity (MFI) ratio of BCMA stained:control stained cells.

In an alternative aspect, the level of BCMA expression is determined by measuring the proportion of plasma cells expressing BCMA. In a further aspect, the proportion may be determined using an immunohistochemistry method.

In one aspect, the proportion of plasma cells expressing BCMA is high when the proportion is greater than 60%. In a further aspect, the proportion is greater than 70%, such as greater than 75%, 80%, 85%, 90%, 95% or 99%.

BLIMP1 (also known as PR domain zinc finger protein 1 or PRDM1) is a transcription factor that controls plasma cell differentiation and appears critical for survival of normal and malignant plasma cells. Therefore, in one aspect, the plasma cells are identified by BLIMP1 expression (i.e. they are BLIMP+ cells). For example, as described in the Examples herein, formalin-fixed paraffin-embedded tissue was stained with anti-BLIMP1 (e.g. clone ROS195G, CNIO, Madrid, Spain) using a protocol optimised on the Bond-III automated staining platform (Leica Biosystems) and the staining for BLIMP1 was used to identify plasma cells.

In one aspect, the proportion of plasma cells expressing BCMA is calculated using a BCMA/BLIMP1 score which is determined by calculating the proportion of BLIMP+ cells that are also BCMA+. In a further aspect BCMA/BLIMP1 scores are assigned as follows:

| BCMA/BLIMP1 score | Proportion of cells |
| --- | --- |
| 0 | 0% |
| 1 | 1-10% |
| 2 | 10-40% |
| 3 | 40-60% |
| 4 | 60-80% |
| 5 | >80% |

In one aspect, the proportion of plasma cells expressing BCMA is high when the BCMA/BLIMP1 score is greater than 4, such as 4-5.

As described herein, the BCMA/BLIMP1 score provided additional prognostic information over and above FISH results, such that patients could be risk-stratified for early relapse and overall survival. Even patients with standard risk genetics were identified to have an earlier relapse rate and shorter survival time if their BCMA levels were high. This discovery offers another method of identifying patients with a poor prognosis, even in the presence of otherwise low/medium cytogenetics. Therefore, in one aspect, the subject tested has standard risk genetics.

As used herein, "samples", such as human samples, include, but are not limited to, whole blood, blood extracts, serum, bone marrow samples, cell extracts or homogenised tissue taken from a patient. A sample for use in the invention can refer to specimen material used for a given assay, reaction, run, trial, and/or experiment. For example, a sample may comprise an aliquot of the specimen material collected, up to and including the entire specimen. Samples may be crude samples or processed samples, e.g., obtained after various processing or preparation steps carried out on the original specimen. For example, various cell separation methods, e.g., magnetically activated cell sorting, may be applied to separate or enrich analytes of interest in a biological fluid, such as blood. A sample may also comprise a dilution of a specimen, e.g., diluted serum or dilutions of other complex and/or protein-rich mixtures. For example, in some aspects, a specimen may be serially diluted to provide a number of serially-diluted samples for analysis. As used herein, the terms "assay", "reaction", "run", "trial" and/or "experiment" can be used interchangeably. Aspects of the present invention can be practiced using small starting amounts of sample to yield quantifiable results.

As described above, BCMA expression is reported to correlate with disease progression in MM. In addition, BCMA expression has also been associated with a number of other disorders. Accordingly the term "BCMA-associated disorders" includes, but is not limited to: Multiple Myeloma (MM), Monoclonal gammopathy of undetermined significance (MGUS), Smoldering multiple myeloma (SMM), Solitary Plasmacytoma (Bone, Extramedullary), Waldenström's Macroglobulinemia, Primary Amyloidosis (AL), Heavy chain disease, Systemic lupus erythematosus (SLE), POEMS syndrome/osteosclerotic myeloma, Type I and II cryoglobulinemia, Light chain deposition disease, Goodpastures syndrome, Idiopathic thrombocytopenic purpura (ITP), Acute glomerulonephritis, Pemphigus and Pemphigoid disorders and Epidermolysis bullosa acquisita, any Non-Hodgkin Lymphoma and Leukemia.

As used herein, the term, "BCMA-associated disorders", also includes clinical conditions based on hematologic tumours of B cell origin. Specific examples of clinical conditions based on hematologic tumors include, but are not limited to, leukemias such as chronic lymphocytic leukemia and acute lymphocytic leukemia; plasma cell malignancies such as multiple myeloma, MGUS and Waldenstrom's macroglobulinemia; lymphomas such as non-Hodgkin's lymphoma, and Hodgkin's lymphoma.

The term "BCMA-associated disorders" also includes cancers in which an abnormal number of blast cells or unwanted cell proliferation is present or that is diagnosed as a hematological cancer, including both lymphoid and myeloid malignancies.

Hematopoietic cancers also include lymphoid malignancies, which may affect the lymph nodes, spleens, bone marrow, peripheral blood, and/or extranodal sites. Lymphoid cancers include B-cell malignancies, which include, but are not limited to, B-cell non-Hodgkin's lymphomas (B-NHLs). B-NHLs may be indolent (or low-grade), intermediate-grade (or aggressive) or high-grade (very aggressive). Indolent B cell lymphomas include follicular lymphoma (FL); small lymphocytic lymphoma (SLL); marginal zone lymphoma (MZL) including nodal MZL, extranodal MZL, splenic MZL and splenic MZL with villous lymphocytes; lymphoplasmacytic lymphoma (LPL); and mucosa-associated-lymphoid tissue (MALT or extranodal marginal zone) lymphoma. Intermediate-grade B-NHLs include mantle cell lymphoma (MCL) with or without leukemic involvement, diffuse large cell lymphoma (DLBCL), follicular large cell (or grade 3 or grade 3B) lymphoma, and primary mediastinal lymphoma (PML). High-grade B-NHLs include Burkitt's lymphoma (BL), Burkitt-like lymphoma, small non-cleaved cell lymphoma (SNCCL) and lymphoblastic lymphoma. Other B-NHLs include immunoblastic lymphoma (or immunocytoma), primary effusion lymphoma, HIV associated (or AIDS related) lymphomas, and post-transplant lymphoproliferative disorder (PTLD) or lymphoma. B-cell malignancies also include, but are not limited to, chronic lymphocytic leukemia (CLL), prolymphocytic leukemia (PLL), Waldenstrom's macroglobulinemia (WM), hairy cell leukemia (HCL), large granular lymphocyte (LGL) leukemia, acute lymphoid (or lymphocytic or lymphoblastic) leukemia, and Castleman's disease. NHL may also include T-cell non-Hodgkin's lymphomas (T-NHLs), which include, but are not limited to T-cell non-Hodgkin's lymphoma not otherwise specified (NOS), peripheral T-cell lymphoma (PTCL), anaplastic large cell lymphoma (ALCL), angioimmunoblastic lymphoid disorder (AILD), nasal natural killer (NK) cell/T-cell lymphoma, gamma/delta lymphoma, cutaneous T cell lymphoma, mycosis fungoides, and Sezary syndrome.

Hematopoietic cancers also include Hodgkin's lymphoma (or disease) including classical Hodgkin's lymphoma, nodular sclerosing Hodgkin's lymphoma, mixed cellularity Hodgkin's lymphoma, lymphocyte predominant (LP) Hodgkin's lymphoma, nodular LP Hodgkin's lymphoma, and lymphocyte depleted Hodgkin's lymphoma. Hematopoietic cancers also include plasma cell diseases or cancers such as multiple myeloma (MM) including smoldering MM, monoclonal gammopathy of undetermined (or unknown or unclear) significance (MGUS), plasmacytoma (bone, extramedullary), lymphoplasmacytic lymphoma (LPL), Waldenström's Macroglobulinemia, plasma cell leukemia, and primary amyloidosis (AL). Hematopoietic cancers may also include other cancers of additional hematopoietic cells, including polymorphonuclear leukocytes (or neutrophils), basophils, eosinophils, dendritic cells, platelets, erythrocytes and natural killer cells. Tissues which include hematopoietic cells referred herein to as "hematopoietic cell tissues" include bone marrow; peripheral blood; thymus; and peripheral lymphoid tissues, such as spleen, lymph nodes, lymphoid tissues associated with mucosa (such as the gut-associated lymphoid tissues), tonsils, Peyer's patches and appendix, and lymphoid tissues associated with other mucosa, for example, the bronchial linings.

The methods described herein may require a comparison of the detected BCMA level with a control (e.g., in methods using flow cytometry). In the case of a qualitative method, this comparison is simply made against a sample with none/normal BCMA expression, such as in non-malignant plasma cells. In a quantitative method, the comparison is made with the level of BCMA expression in the control.

The control may be a sample taken from a healthy human known not to be suffering from a BCMA-associated disorder. The control will be chosen based on the particular BCMA-associated disorder which is being assessed.

Antigen Binding Proteins

A further aspect of the invention provides an antigen binding protein that specifically binds to BCMA for use in the treatment of multiple myeloma in a subject classified with poor prognosis, wherein said subject is characterised by a high proportion of plasma cells expressing BCMA in a sample from the subject.

The antigen binding proteins of the present invention may comprise heavy chain variable regions and/or light chain variable regions of the invention which may be formatted into the structure of a natural antibody or functional fragment or equivalent thereof. An antigen binding protein of the invention may therefore comprise the VH regions of the invention formatted into a full length antibody, a (Fab')2 fragment, a Fab fragment, or equivalent thereof (such as scFV, bi- tri- or tetra-bodies, Tandabs, etc.), when paired with an appropriate light chain. The antibody may be an IgG1, IgG2, IgG3, or IgG4; or IgM; IgA, IgE or IgD or a modified variant thereof. The constant domain of the antibody heavy chain may be selected accordingly. The light chain constant domain may be a kappa or lambda constant domain. Furthermore, the antigen binding protein may comprise modifications of all classes, e.g., IgG dimers, Fc mutants that no longer bind Fc receptors or mediate C1q binding. The antigen binding protein may also be a chimeric antibody of the type described in WO86/01533 which comprises an antigen binding region and a non-immunoglobulin region.

In another aspect of the invention. the antigen binding protein is selected from the group consisting of: a dAb, Fab, Fab', F(ab')2, Fv, diabody, triabody, tetrabody, miniantibody, and a minibody.

Chimeric antigen receptors (CARs) have been developed as artificial T cell receptors to generate novel specificities in T cells without the need to bind to MHC-antigenic peptide complexes. These synthetic receptors contain a target binding domain that is associated with one or more signalling domains via a flexible linker in a single fusion molecule. The target binding domain is used to target the T cell to specific targets on the surface of pathologic cells and the signalling domains contain molecular machinery for T cell activation and proliferation. The flexible linker which passes through the T cell membrane (i.e. forming a transmembrane domain) allows for cell membrane display of the target binding domain of the CAR. CARs have successfully allowed T cells to be redirected against antigens expressed at the surface of tumour cells from various malignancies including lymphomas and solid tumours (Jena et al. (2010) *Blood,* 116(7): 1035-44).

The development of CARs has comprised three generations so far. The first generation CARs comprised target binding domains attached to a signalling domain derived from the cytoplasmic region of the CD3zeta or the Fc receptor gamma chains. First generation CARs were shown to successfully redirect T cells to the selected target, however, they failed to provide prolonged expansion and anti-tumor activity in vivo. The second and third generation CARs have focussed on enhancing modified T cell survival and increasing proliferation by including co-stimulatory molecules, such as CD28, OX-40 (CD134) and 4-1BB (CD137).

T cells bearing CARs could be used to eliminate pathologic cells in a disease setting. One clinical aim would be to transform patient cells with recombinant DNA containing an expression construct for the CAR via a vector (e.g. a lentiviral vector) following aphaeresis and T cell isolation. Following expansion of the T cells they are re-introduced into the patient with the aim of targeting and killing the pathologic target cells.

In one aspect of the invention the antigen binding protein is a chimeric antigen receptor. In a further aspect the CAR comprises a binding domain, a transmembrane domain and an intracellular effector domain.

In one aspect, the transmembrane domain can be derived either from a natural or from a synthetic source. In one aspect, the transmembrane domain can be derived from any membrane-bound or transmembrane protein. Alternatively the transmembrane domain can be synthetic and can comprise predominantly hydrophobic residues such as leucine and valine.

For example, the transmembrane domain can be the transmembrane domain of CD proteins, such as CD4, CD8, CD3 or CD28, a subunit of the T cell receptor, such as α, β, γ or δ, a subunit of the IL-2 receptor (α chain), a submit of the Low-Affinity Nerve Growth Factor Receptor (LNGFR or p75) (β chain or γ chain), or a subunit chain of Fc receptors. In one aspect, the transmembrane domain comprises the transmembrane domain of CD4, CD8 or CD28. In a further aspect, the transmembrane domain comprises the transmembrane domain of CD4 or CD8 (e.g. the CD8 alpha chain, as described in NCBI Reference Sequence: NP_001139345.1, incorporated herein by reference). In a yet further aspect, the transmembrane domain comprises the transmembrane domain of CD4.

The intracellular effector domain or "signalling domain" is responsible for intracellular signalling following the binding of the target binding domain to the target. The intracellular effector domain is responsible for the activation of at least one of the normal effector functions of the immune cell in which the CAR is expressed. For example, the effector function of a T cell can be a cytolytic activity or helper activity including the secretion of cytokines. Preferred examples of the effector domain for use in a CAR scaffold can be the cytoplasmic sequences of the natural T cell receptor and co-receptors that act in concert to initiate signal transduction following antigen binding, as well as any derivate or variant of these sequences and any synthetic sequence that has the same functional capability. Effector domains can be separated into two classes: those that initiate antigen-dependent primary activation, and those that act in an antigen-independent manner to provide a secondary or costimulatory signal. Primary activation effector domains can comprise signalling motifs which are known as immunoreceptor tyrosine-based activation motifs (ITAMs). ITAMs are well defined signalling motifs, commonly found in the intracytoplasmic tail of a variety of receptors, and serve as binding sites for syk/zap70 class tyrosine kinases. Examples of ITAMs used in the invention can include, as non limiting examples, those derived from CD3zeta, FcR-gamma, FcRbeta, FcRepsilon, CD3gamma, CD3delta, CD3epsilon, CD5, CD22, CD79a, CD79b and CD66d. In one aspect, the intracellular effector domain comprises a CD3zeta signalling domain (also known as CD247). Natural TCRs contain a CD3zeta signalling molecule, therefore the use of this effector domain is closest to the TCR construct which occurs in nature.

In one aspect of the invention the intracellular signalling domain is a CD3 zeta effector domain.

Effector domains may also provide a secondary or costimulatory signal. T cells additionally comprise costimulatory molecules which bind to cognate costimulatory ligands on antigen presenting cells in order to enhance the T cell response, for example by increasing proliferation activation, differentiation and the like. Therefore, in one aspect, the intracellular effector domain additionally comprises a costimulatory domain. In a further aspect, the costimulatory domain comprises the intracellular domain of a costimulatory molecule, selected from CD28, CD27, 4-1BB (CD137), OX40 (CD134), ICOS (CD278), CD30, CD40, PD-1 (CD279), CD2, CD7, NKG2C (CD94), B7-H3 (CD276) or any combination thereof. In a yet further aspect, the costimulatory domain comprises the intracellular domain of a costimulatory molecule, selected from CD28, CD27, 4-1BB, OX40, ICOS or any combination thereof.

In one aspect of the present invention, the antigen binding protein is a humanised or chimaeric antibody. In a further aspect of the invention, the antibody is humanised.

In one aspect of the invention, the antibody is a monoclonal antibody.

In another aspect of the invention, the antigen binding protein binds to human BCMA with high affinity, for example, when measured by Biacore the antigen binding protein binds to human BCMA with an affinity of 20 nM or less or an affinity of 15 nM or less or an affinity of 5 nM or less or an affinity of 1000 pM or less or an affinity of 500 pM or less or an affinity of 400 pM or less, or 300 pM or less or, for example, about 120 pM. In a further aspect of the invention, the antigen binding protein binds to human BCMA when measured by Biacore of between about 100 pM and about 500 pM or between about 100 pM and about 400 pM, or between about 100 pM and about 300 pM. In one aspect of the invention, the antigen binding protein binds BCMA with an affinity of less than 150 pm.

In one such aspect of the invention, the affinity of the antigen binding protein is measured by Biacore.

In another aspect of the invention, the antigen binding protein binds to human BCMA and neutralises the binding of the ligands BAFF and/or APRIL to the BCMA receptor in a cell neutralisation assay, wherein the antigen binding protein has an IC50 of between about 1 nM and about 500 nM, or between about 1 nM and about 100 nM, or between about 1 nM and about 50 nM, or between about 1 nM and about 25 nM, or between about 5 nM and about 15 nM. In a further aspect of the invention, the antigen binding protein binds BCMA and neutralises BCMA in a cell neutralisation assay, wherein the antigen binding protein has an IC50 of about 10 nM. In one such aspect of the invention, IC50 is measured by a cell neutralisation assay.

Afucosylated monoclonal antibodies are monoclonal antibodies engineered so that the oligosaccharides in the Fc region of the antibody do not have any fucose sugar units. Without being bound by theory, antibody-dependent cellular cytotoxicity (ADCC) is increased when antibodies are afucosylated. Therefore, in one aspect of the invention, the antigen binding protein comprises a chimaeric heavy chain constant region that has an altered glycosylation profile. In one such aspect of the invention, the heavy chain constant region has an altered glycosylation profile, such that the ratio of fucose to mannose is 0.8:3 or less, for example, wherein the antigen binding protein is completely defucosylated.

In one aspect, the antigen binding protein comprises CDRH3 of SEQ ID NO: 3 or a variant of SEQ ID NO: 3.

In one aspect of the invention, the antigen binding protein further comprises at least one of: CDRH1 of SEQ ID NO: 1; CDRH2 of SEQ ID NO: 2; CDRL1 of SEQ ID NO: 4; CDRL2 of SEQ ID NO: 5; and/or CDRL3 of SEQ ID NO: 6.

In one aspect, the antigen binding protein comprises:
i) CDRH3 as set out in SEQ ID NO: 3
ii) CDRH1 as set out in SEQ ID NO: 1; and
iii) CDRH2 as set out in SEQ ID NO: 2

In one aspect, the antigen binding protein comprises:
i) CDRH3 as set out in SEQ ID NO: 3
ii) CDRH1 as set out in SEQ ID NO: 1
iii) CDRH2 as set out in SEQ ID NO: 2
iv) CDRL1 as set out in SEQ ID NO: 4
v) CDRL2 as set out in SEQ ID NO: 5; and
vi) CDRL3 as set out in SEQ ID NO: 6.

In one aspect, the antigen binding protein comprises a heavy chain variable region encoded by any one of SEQ ID NO: 11 or SEQ ID NO: 13 or SEQ ID NO: 15.

In one aspect, the antigen binding protein comprises a light chain variable region encoded by any one of SEQ ID NO: 17 or SEQ ID NO: 19.

In one aspect, the antigen binding protein comprises a heavy chain variable region encoded by SEQ ID NO: 11 and a light chain variable region encoded by SEQ ID NO: 17.

In one aspect, the antigen binding protein comprises a heavy chain variable region encoded by SEQ ID NO: 15 and a light chain variable region encoded by SEQ ID NO: 17.

In an alternative aspect, the antigen binding protein is a humanised monoclonal antibody.

The invention also provides a polynucleotide sequence encoding a heavy chain variable region of any of the antigen-binding proteins described herein, and a polynucleotide encoding a light chain variable region of any of the antigen-binding proteins described herein.

The invention also provides a polynucleotide sequence encoding a heavy chain of any of the antigen-binding proteins described herein, and a polynucleotide encoding a light chain of any of the antigen-binding proteins described herein.

Such polynucleotides represent the coding sequence that corresponds to the equivalent polypeptide sequences. However, it will be understood that such polynucleotide sequences could be cloned into an expression vector along with a start codon, an appropriate signal sequence, and a stop codon.

In one aspect of the invention, the antigen binding protein additionally comprises a cytotoxic agent. Suitable cytotoxic agents include, but are not limited to, an auristatin including dovaline-valine-dolaisoleunine-dolaproine-phenylalanine (MMAF) and monomethyl auristatin E (MMAE) as well as ester forms of MMAE, a DNA minor groove binding agent, a DNA minor groove alkylating agent, an enediyne, a lexitropsin, a duocarmycin, a taxane, including paclitaxel and docetaxel, a puromycin, a dolastatin, a maytansinoid, and a vinca alkaloid. Specific cytotoxic agents include topotecan, morpholino-doxorubicin, rhizoxin, cyanomorpholino-doxorubicin, dolastatin-10, echinomycin, combretatstatin, chalicheamicin, maytansine, DM-1, DM-4, netropsin. Other suitable cytotoxic agents include anti-tubulin agents, such as an auristatin, a vinca alkaloid, a podophyllotoxin, a taxane, a baccatin derivative, a cryptophysin, a maytansinoid, a combretastatin, or a dolastatin. Antitubulin agent include dimethylvaline-valine-dolaisoleuine-dolaproine-phenylalanine-p-phenylened-iamine (AFP), MMAF, MMAE, auristatin E, vincristine, vinblastine, vindesine, vinorelbine, VP-16, camptothecin, paclitaxel, docetaxel, epothilone A, epothilone B, nocodazole, colchicines, colcimid, estramustine, cemadotin, discodermolide, maytansine, DM-1, DM-4 or eleutherobin.

In another aspect of the invention, the antigen binding protein is linked to the cytotoxic agent via a linker.

In yet another aspect of the invention, the cytotoxic agent is an auristatin or a dolostatin.

In one aspect of the invention, the cytotoxic agent is selected from MMAE and MMAF.

In one aspect, the cytotoxic agent is covalently bound to the antigen binding protein.

In one aspect of the invention, the linker is a cleavable linker. In an alternative aspect of the invention, the linker is a non-cleavable linker. In a further aspect, the linker is selected from; 6-maleimidocaproyl (MC), maleimidopropanoyl (MP), valine-citrulline (val-cit), alanine-phenylalanine (ala-phe), p-aminobenzyloxycarbonyl (PAB), N-Succinimidyl 4-(2-pyridylthio)pentanoate (SPP), N-succinimidyl 4-(N-maleimidomethyl)cyclohexane-1 carboxylate (SMCC), and N-Succinimidyl (4-iodo-acetyl) aminobenzoate (SIAB).

Antibody drug conjugates described herein may be produced by conjugating the small molecule anti-tubulin agent monomethylauristatin E (MMAE) or monomethylauristatin F (MMAF) to the anti-BCMA antibodies. In the case of MMAE the linker may consist of a thiol-reactive maleimide, a caproyl spacer, the dipeptide valine-citrulline, and p-aminobenzyloxycarbonyl, a self-immolative fragmenting group. In the case of MMAF a protease-resistant maleimidocaproyl linker may be used. The conjugation process leads to heterogeneity in drug-antibody attachment, varying in both the number of drugs bound to each antibody molecule (mole ratio [MR]), and the site of attachment. The most prevalent species is the material with an MR=4; less prevalent are materials with MR of 0, 2, 6, and 8. In one aspect, the overall average drug-to-antibody MR is approximately 4.

In one aspect, the antigen binding protein is an antibody which is a humanized IgG1 monoclonal (mAb) anti-BCMA antibody produced in an afucosylated form and conjugated to monomethyl auristatin-F (MMAF). The cytotoxic effects of this antibody require binding to the surface of BCMA-expressing cells, internalization, and transport to the lysosome where the antibody undergoes proteolytic degradation and cys-mcMMAF is released. This inhibits mitosis by disrupting microtubules, causing cell cycle arrest in G2/M and subsequent apoptosis. Notably, free cys-mcMMAF has low cytotoxic activity in vitro, thought to be due to a charged C-terminal phenylalanine group that impairs its ability to cross cell membranes (Doronina et al., 2006). Both NK and macrophage-mediated lysis may also play a role in the activity of J6M0-MMAF on MM cells as recently reported (Tai et al., 2014).

Methods of Treatment

The uses and methods of the invention described above allow for the prognosis of humans suffering from a BCMA-associated disorder. Once identified, the disorder may be treated. Accordingly, the invention provides a method of treating multiple myeloma in a subject, comprising administering a therapeutically effective amount of an antigen binding protein which specifically binds to BCMA to a subject, wherein said subject has a high proportion of plasma cells expressing BCMA.

According to a further aspect of the invention, there is provided a method of treating multiple myeloma in a subject with a high proportion of plasma cells expressing BCMA calculated according to the prognosis method described herein.

According to another aspect of the invention, there is provided a method of treating multiple myeloma in a subject, comprising identifying a subject having a high level of BCMA expression and administering to the subject a therapeutically effective amount of the antigen binding protein described herein. The level of BCMA expression can be calculated according to the prognosis method described herein.

In a further aspect of the invention, there is provided a method of treating multiple myeloma in a subject comprising the steps of i) obtaining a sample from a subject; ii) determining the level of BCMA expression in the sample, and iii) if the level of BCMA expression is high, administering a therapeutically effective amount of the antigen binding protein described herein. The level of BCMA expression can be determined according to the prognosis method described herein.

The inventors of the present application made the surprising observation that shorter disease-free survival was associated with a high BCMA expression level, even in patients with standard risk genetics which would not previously have been identified as patients at significant risk. Therefore, patients identified in this subset (i.e. with a poor prognosis) would be more suitable for an aggressive treatment regimen.

Such treatment regimen may require more frequent dosage with antigen binding proteins of the invention as herein described, higher dosage or combination therapies.

A number of the methods of treating a human with a BCMA-associated disorder described above include treating a human who has been identified as having a high proportion of plasma cells expressing BCMA. The identification may occur shortly before treatment, that is, the human is identified and then treated less than a week after identification, i.e.

less than 7, 6, 5, 4, 3, 2, or 1 day after identification. The identification may also have been carried out at a previous time. For example a human may have been identified as having a high proportion of plasma cells expressing BCMA more than a week before treatment, i.e. more than 1, 2, 3, 4, 5, 6, 8, 10, 12, 15, 20, 25, 30, 35, 40, 45, 50, or 100 weeks before administration of the BCMA antigen binding protein. Both aspects are included within the method of treatment of the invention.

The skilled person provided with the present invention will appreciate that a new, distinct sub-group of patients (those showing elevated levels of BCMA expression) are now able to be treated for multiple myeloma. Therefore the invention includes all permutations of methods and uses that allow treatment of this sub-group. For example, the invention provides a method of treating multiple myeloma in a human comprising the steps of: (a) determining that a sample obtained from a human contains a high proportion of plasma cells expressing BCMA; and (b) if a high proportion (such as a high BCMA/BLIMP1 score) is detected, administering a therapeutically effective amount of a BCMA antigen binding protein, such as the antigen binding protein described herein.

Furthermore, certain steps in the methods and uses of the invention may be combined. For example, the steps of: (a) obtaining a human sample; and (b) testing the sample for the proportion of plasma cells expressing BCMA may be combined into a single step of: (a') testing a human sample for the proportion of plasma cells expressing BCMA. These methods and uses are all intended to be included within the scope of the invention.

The mode of administration of the therapeutic agent of the invention may be any suitable route that delivers the agent to the host. The antigen binding proteins of the invention are particularly useful for parenteral administration, i.e., subcutaneously (s.c.), intrathecally, intraperitoneally, intramuscularly (i.m.) or intravenously (i.v.). In one such aspect the antigen binding proteins of the present invention are administered intravenously or subcutaneously.

Therapeutic agents of the invention may be prepared as pharmaceutical compositions containing an effective amount of the antigen binding protein of the invention as an active ingredient in a pharmaceutically acceptable carrier. In one aspect of the invention, the therapeutic agent of the invention is an aqueous suspension or solution containing the antigen binding protein in a form ready for injection. In another aspect, the suspension or solution is buffered at physiological pH. In one aspect, the compositions for parenteral administration will comprise a solution of the antigen binding protein of the invention or a cocktail thereof dissolved in a pharmaceutically acceptable carrier. In one aspect, the carrier is an aqueous carrier. A variety of aqueous carriers may be employed, including, but not limited to, 0.9% saline and 0.3% glycine. These solutions may be made sterile and generally free of particulate matter. These solutions may be sterilized by conventional, well known sterilization techniques (e.g., filtration). The compositions may contain pharmaceutically acceptable auxiliary substances as required to approximate physiological conditions such as pH adjusting and buffering agents, etc. The concentration of the antigen binding protein of the invention in such pharmaceutical formulation can vary widely, i.e., from less than about 0.5%, usually at or at least about 1% to as much as about 15 or 20% by weight and will be selected primarily based on fluid volumes, viscosities, etc., according to the particular mode of administration selected.

Thus, a pharmaceutical composition of the invention for intravenous infusion could be made up to contain about 250 ml of sterile Ringer's solution, and about 1 to about 30 or 5 mg to about 25 mg of an antigen binding protein of the invention per ml of Ringer's solution. Actual methods for preparing parenterally administrable compositions are well known or will be apparent to those skilled in the art and are described in more detail in, for example, Remington's Pharmaceutical Science, 15th ed., Mack Publishing Company, Easton, Pa. For the preparation of intravenously administrable antigen binding protein formulations of the invention see Lasmar and Parkins, (2000) *Pharma. Sci. Tech. Today,* 3: 129-137; Wang (1999) *Int. J. Pharm.* 185: 129-188; Stability of Protein Pharmaceuticals Part A and B ed Ahern T. J., Manning M. C., New York, N.Y.: Plenum Press (1992); Akers (2002) *J. Pharm. Sci.* 91: 2283-2300; Imamura, K et al., (2003) *J. Pharm. Sci.* 92: 266-274; Izutsu and Kkojima (2002) *J. Pharm. Pharmacol,* 54: 1033-1039; Johnson (2002) *J. Pharm. Sci,* 91: 914-922; and Ha et al., (2002) *J. Pharm. Sci,* 91, 2252-2264; the entire contents of which are incorporated herein by reference and to which the reader is specifically referred.

In one aspect, the therapeutic agent of the invention, when in a pharmaceutical preparation, is present in unit dose forms. The appropriate therapeutically effective dose will be determined readily by those of skill in the art. Suitable doses may be calculated for patients according to their weight. For example, suitable doses may be in the range of about 0.1 to about 20 mg/kg, for example about 1 to about 20 mg/kg, for example about 10 to about 20 mg/kg or for example about 1 to about 15 mg/kg, for example about 10 to about 15 mg/kg. To effectively treat conditions such as MM, SLE or IPT in a human, suitable doses may be within the range of about 0.1 to about 1000 mg, for example about 0.1 to about 500 mg, for example about 500 mg, for example about 0.1 to about 100 mg, or about 0.1 to about 80 mg, or about 0.1 to about 60 mg, or about 0.1 to about 40 mg, or for example about 1 to about 100 mg, or about 1 to about 50 mg, of an antigen binding protein of this invention, which may be administered parenterally, for example subcutaneously, intravenously or intramuscularly. Such dose may, if necessary, be repeated at appropriate time intervals selected as appropriate by a physician.

The dose and duration of treatment relates to the relative duration of the molecules of the present invention in the human circulation, and can be adjusted by one of skill in the art depending upon the condition being treated and the general health of the patient. It is envisaged that repeated dosing (e.g. once a week or once every two weeks or once every 3 weeks) over an extended time period (e.g. four to six months) maybe required to achieve maximal therapeutic efficacy.

The antigen binding proteins described herein can be lyophilized for storage and reconstituted in a suitable carrier prior to use. This technique has been shown to be effective with conventional immunoglobulins and art-known peroxidise and reconstitution techniques can be employed.

A further aspect of the invention provides a method of treating multiple myeloma in a human by administering to the human an antigen binding protein that specifically binds to BCMA in a human identified as suitable for said treatment:
  (a) by the human having a high proportion of plasma cells expressing BCMA; or
  (b) using the prognosis method described herein.

Kits

In another aspect, the invention provides a kit for determining prognosis of a subject, the kit comprising reagents for measuring expression levels of BCMA. In yet another aspect, the invention provides a kit for determining BCMA expression in a subject, the kit comprising reagents for measuring expression levels of BCMA in a sample.

In one aspect, the expression level of BCMA is measured by determining the proportion of plasma cells in a sample which express BCMA (e.g., using the BCMA/BLIMP1 score as described herein). In another aspect, the means for detecting plasma cells is an anti-BLIMP1 antibody and the means for measuring expression levels of BCMA is an anti-BCMA antibody. In another aspect, the reagents are those suitable for measuring BCMA expression levels by flow cytometry (such as the reagents used in the Examples described herein).

In another aspect, the invention there is provided a kit-of-parts comprising reagents for measuring expression levels of BCMA together with instructions for use.

All patent and literature references disclosed within the present specification are expressly and entirely incorporated herein by reference.

Definitions

The term, "antigen binding protein", as used herein refers to antibodies, antibody fragments and other protein constructs such as chimeric antigen receptors that are capable of binding to and neutralising human BCMA.

The terms Fv, Fc, Fd, Fab, or F(ab)2 are used with their standard meanings (see, e.g., Harlow et al., 1988).

The term, "antibody", is used herein in the broadest sense and specifically covers monoclonal antibodies (including full length monoclonal antibodies), polyclonal antibodies, multispecific antibodies (e.g., bispecific antibodies).

The term, "monoclonal antibody", as used herein refers to an antibody obtained from a population of substantially homogenous antibodies, i.e., the individual antibodies comprising the population are identical except for possible naturally occurring mutations that may be present in minor amounts. Monoclonal antibodies are highly specific being directed against a single antigenic binding site. Furthermore, in contrast to polyclonal antibody preparations which typically include different antibodies directed against different determinants (epitopes), each monoclonal antibody is directed against a single determinant on the antigen.

A "humanised antibody", as used herein, refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity (see, e.g., Queen et al., (1989) *PNAS USA*, 86:10029-10032, Hodgson et al., (1991) *Biotechnology*, 9:421). A suitable human acceptor antibody may be one selected from a conventional database, e.g., the KABAT® database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody. The prior art describes several ways of producing such humanised antibodies—see for example EP0239400.

The term, "specifically binds", as used throughout the present specification in relation to antigen binding proteins of the invention means that the antigen binding protein binds human BCMA (hBCMA) with no or insignificant binding to other human proteins. This term, however, does not exclude the fact that antigen binding proteins of the invention may also be cross-reactive with other forms of BCMA, for example, primate BCMA. For example, in one aspect of the invention, the antigen binding protein does not bind to TACI or BAFF-R.

"CDRs" are defined as the complementarity determining region amino acid sequences of an antibody which are the hypervariable domains of immunoglobulin heavy and light chains. There are three heavy chain and three light chain CDRs (or CDR regions) in the variable portion of an immunoglobulin. Thus, "CDRs", as used herein may refer to all three heavy chain CDRs, or all three light chain CDRs (or both all heavy and all light chain CDRs, if appropriate).

CDRs provide the majority of contact residues for the binding of the antibody to the antigen or epitope. CDRs of interest in this invention are derived from donor antibody variable heavy and light chain sequences, and include analogs of the naturally occurring CDRs, which analogs also share or retain the same antigen binding specificity and/or neutralizing ability as the donor antibody from which they were derived.

The CDR sequences of antibodies can be determined by the Kabat numbering system (Kabat et al., (1987) Sequences of proteins of Immunological Interest NIH), alternatively they can be determined using the Chothia numbering system (Al-Lazikani et al., (1997) *JMB* 273, 927-948), the contact definition method (MacCallum et al., (1996), *J Mol Biol*, 262(5), 732-745) or any other established method for numbering the residues in an antibody and determining CDRs known to the skilled man in the art.

Other numbering conventions for CDR sequences available to a skilled person include "AbM" (University of Bath) and "contact" (University College London) methods. The minimum overlapping region using at least two of the Kabat, Chothia, AbM and contact methods can be determined to provide the "minimum binding unit". The minimum binding unit may be a sub-portion of a CDR.

Throughout this specification, amino acid residues in antibody sequences are numbered according to the Kabat scheme. Similarly, the terms "CDR", "CDRL1", "CDRL2", "CDRL3", "CDRH1", "CDRH2", "CDRH3" follow the Kabat numbering system as set forth in Kabat et al., (1987).

The term, "variant", as used herein refers to at least one, two or three amino acid changes in the sequence. These amino acid changes may be deletion, substitution or addition but are preferably substitution. In one such aspect the substitutions are conservative substitutions. In an alternative aspect the variant sequence contains at least one substitution whilst retaining the canonical of the antigen binding protein.

The complementarity determining regions (CDRs) L1, L2, L3, H1 and H2 tend to structurally exhibit one of a finite number of main chain conformations. The particular canonical structure class of a CDR is defined by both the length of the CDR and by the loop packing, determined by residues located at key positions in both the CDRs and the framework regions (structurally determining residues or SDRs). Martin and Thornton (*J Mol Biol* (1996) 263: 800-815) have generated an automatic method to define the "key residue"

canonical templates. Cluster analysis is used to define the canonical classes for sets of CDRs, and canonical templates are then identified by analysing buried hydrophobics, hydrogen-bonding residues, and e.g. conserved glycines. The CDRs of antibody sequences can be assigned to canonical classes by comparing the sequences to the key residue templates and scoring each template using identity or similarity matrices.

The terms, "VH" and "VL", are used herein to refer to the heavy chain variable domain and light chain variable domain respectively of an antibody.

The phrase, "immunoglobulin single variable domain", as used herein refers to an antibody variable domain (VH, VHH, VL) that specifically binds an antigen or epitope independently of a different V region or domain. An immunoglobulin single variable domain can be present in a format (e.g., homo- or hetero-multimer) with other, different variable regions or variable domains where the other regions or domains are not required for antigen binding by the single immunoglobulin variable domain (i.e., where the immunoglobulin single variable domain binds antigen independently of the additional variable domains). A "domain antibody" or "dAb" is the same as an "immunoglobulin single variable domain" which is capable of binding to an antigen as the term is used herein. An immunoglobulin single variable domain may be a human antibody variable domain, but also includes single antibody variable domains from other species such as rodent (for example, as disclosed in WO 00/29004), nurse shark and Camelid VHH dAbs. Camelid VHH are immunoglobulin single variable domain polypeptides that are derived from species including camel, llama, alpaca, dromedary, and guanaco, which produce heavy chain antibodies naturally devoid of light chains. Such VHH domains may be humanised according to standard techniques available in the art, and such domains are still considered to be "domain antibodies" according to the invention. As used herein, "VH", includes camelid VHH domains. NARV are another type of immunoglobulin single variable domain which were identified in cartilaginous fish including the nurse shark. These domains are also known as Novel Antigen Receptor variable region (commonly abbreviated to V(NAR) or NARV). For further details, see Shao et al., (2006) Mol. Immunol. 44, 656-665 and US2005/0043519.

The term "chimeric antigen receptors" ("CARs") as used herein, refers to an engineered receptor which consists of an extracellular target binding domain (which is usually derived from a monoclonal antibody), a spacer region, a transmembrane region, and one or more intracellular effector domains. CARs have also been referred to as chimeric T cell receptors or chimeric immunoreceptors (CIRs). CARs are genetically introduced into hematopoietic cells, such as T cells, to redirect specificity for a desired cell-surface antigen.

The terms, "subject" and "patient," are used interchangeably herein, and refer to an animal such as a mammal, in particular a human, which is afflicted with or suspected of having, at risk of, or being predisposed to multiple myeloma (MM). The terms also include domestic animals bred for food, sport, or as pets, including horses, cows, sheep, poultry, fish, pigs, cats, dogs, and zoo animals, goats, apes (e.g. gorilla or chimpanzee), and rodents, such as rats and mice.

The term, "diagnosed," as used herein, refers to the recognition of a disease by its signs and symptoms, or genetic analysis, pathological analysis, histological analysis, and the like.

"Prognosis", as used herein, refers to a prediction of the course of a disease, such as multiple myeloma. The prediction can include determining the likelihood of a subject to develop aggressive, recurrent disease, to survive a particular amount of time (e.g. determine the likelihood that a subject will survive 1, 2, 3, 4, or 5 years or the likelihood of disease relapse), to respond to a particular therapy (e.g., monoclonal antibody therapy), or combinations thereof.

The invention will now be described further with reference to the following Examples:

EXAMPLES

Example 1. Human Myeloma Cell Lines

Human myeloma cell lines (HMCL) were authenticated using STR profiling, or purchased from ATCC, and were cultured in RPMI/10% foetal calf serum (FCS).

Cells were cultured in RPMI (Lonza)/10% FCS (Gibco)/100 U/ml penicillin & 100 µg/ml streptomycin (Gibco) unless otherwise specified. BCMA expressing ARH-77 cells were generated by adding 2 µg of plasmid DNA: pCDNA3.1 E51 hBCMA, BioCat: 128192, 2×10$^6$ ARH-77 cells (GenMab) and 100 µl of Nucleofector solution V to each Amaxa Nucleofector cuvette and electroporating on programme O-017 in an Amaxa Nucleofector™ II (all Lonza). From 24 hours, Geneticin (G418, 1 mg/ml) was added to growth media. Following expansion, 10×10$^6$ of these bulk transfected cells were labelled with 10 µg/mL of FITC conjugated rat anti-BCMA antibody (Vicky-1, Enzo) and then single cell sorted on a FACS Aria II high speed sorter (BD) selecting the highest 1% and lowest 5% of fluorescently stained cells.

Example 2—BCMA Antibodies

The parent anti-BCMA antibody is Fc enhanced by defucosylation using Biowa™ technology which utilizes FUT8 deficient producer cells to form J6M0. This Fc-enhanced antibody is conjugated to the microtubule-disrupting agent MMAF via a protease resistant maleimidocaproyl (mc) linker to produce J6M0-MMAF. J6M0 was used for confocal microscopy and flow cytometry receptor internalization and recycling studies. The wild type Fc form of J6M0 (J6M0-wtFc) was used for quantification of soluble BCMA and PE conjugated for flow cytometry of patient cells. For immunohistochemistry, a murine reverse chimera of J6M0 was engineered (J6M0 muIgG2a). Two other murine monoclonals were used: S307118G03, FITC conjugated and used for flow cytometry, and S336105A07 in confocal microscopy. Details of antibodies used are summarised in Table 1.

TABLE 1

Anti-BCMA antibodies summary.

| Name | Species and Isotype | Conjugation | Use |
|---|---|---|---|
| J6M0-wtFc | WT Fc huIgG1 | Unconjugated or PE | PE-Flow unconjugated-ELISA assessment of sBCMA |
| J6M0 | Human IgG1-Fc enhanced | None | Investigation of receptor dynamics by flow or confocal microscopy |

TABLE 1-continued

Anti-BCMA antibodies summary.

| Name | Species and Isotype | Conjugation | Use |
|---|---|---|---|
| J6M0-MMAF | Human IgG1-Fc enhanced | MMAF | Cytotoxic assays Investigation of receptor dynamics by flow. |
| Human IgG1 isotype control | Human IgG1 Fc enhanced | None | Isotype control and Fc block for flow |
| S307118G03 | Murine IgG2a | Alexa 488 | Flow |
| S336105A07 | Murine IgG | None | Confocal microscopy |
| J6M0 muIgG2a | Human/murine chimera with J6M0 variable region and muIgG2a Fc portion | None | IHC |
| Mu IgG2a isotype control | Murine IgG2a | Alexa 488 | Flow control |

Example 3—Patients and Bone Marrow Processing

Patients gave full informed consent using a protocol approved by the UCL/UCLH Committee for Ethics of Human Research. Mononuclear cells (MNCs) from BM aspirates were obtained by density gradient centrifugation (Ficoll Paque, GE lifesciences). All patients had FISH analysis on CD138-selected cells at the time of bone marrow sampling. Adverse genetics was defined as the presence of. t(4;14), t(14;16), t(14;20), 1q gain, 13q loss, 1p loss and/or del(17p)(>50%).

Example 4—BCMA Expression on Patient Cells by Flow Cytometry

Cells were incubated with FITC-conjugated S307118G03 or with PE-conjugated J6M0-wtFc for 30 minutes at 4° C., washed, resuspended in FACS buffer and analysed (BD Facsverse). The MFI ratio refers to the mean cell fluorescence with specific antibody compared to isotype control.

For assessment of surface BCMA expression, murine anti-BCMA (clone S307118G03, conjugated to AlexaFluor488), and the humanised antibody, J6M0-wtFc conjugated to PE were used in parallel. In the case of primary MM cells, staining was carried out on bone marrow (BM) mononuclear cells (MNCs) in 100 μl PBS (Lonza)/ 0.5% BSA(PAA), using anti CD138 APC (Miltenyi), to identify tumour cells. Relevant isotype controls were used but in the case of J6M0-wtFc PE, cells were pre-incubated with Biowa huIgG1 for 10 minutes prior to addition of J6M0-wtFc PE, to block non-specific binding to Fc receptors. Anti CD20 Pacific Blue (PB) (Biolegend), anti CD28 PB (Biolegend) and anti CD56 PE (Miltenyi) were also used. All incubations with antibodies were performed at 4° C. for 30 minutes, after which cells were washed with PBS/0.5% BSA, and run on the Cyan flow cytometer (Beckman Coulter) or BD Facs Verse. Summit software was used to analyse data. A semi-quantitative measure of BCMA surface expression on MM cells was obtained from the ratio of the MFI of anti BCMA, versus isotype control stained samples (MFI ratio).

To quantify antigen expression, 50 μl PE Quantibrite beads (BD) were run concurrently, and antibodies bound per cell were calculated as per manufacturer's instructions.

Example 5—BCMA Expression by Immunohistochemistry

Formalin-fixed paraffin-embedded tissue was stained with J6M0 muIgG2a alone or with anti BLIMP1 (clone ROS195G, CNIO, Madrid, Spain) using a protocol optimised on the Bond-III automated staining platform (Leica Biosystems). Staining for BLIMP1 was used to identify plasma cells. The BCMA/BLIMP1 score refers to the proportion of BLIMP+ cells that were also BCMA+ (scores of 0-5 correlating to 0%, 1-10%, 10-40%, 40-60%, 60-80% and >80% respectively).

First, J6M0 muIgG2a (2 mg/ml) in purified unconjugated form was tested for its reactivity and specificity for detection of the target protein in formalin-fixed paraffin-embedded (FFPE) material on the Bond-III automated staining platform (Leica Biosystems, Newcastle Upon Tyne, UK). Control material took the form of FFPE cell pellets of the EBV-transformed B lymphoblastoid cell line ARH-77 transduced with varying amounts of BCMA. Next, 2-3 μm thick sections were cut onto charged slides, drained and baked at 60° C. for 1 hour before undergoing initial automated dewaxing and blocking of endogenous peroxidase using 3-4% (v/v) hydrogen peroxide. Dilution curves were performed with a range of epitope retrieval methods; no pre-treatment; protease digestion; or heat induced epitope retrieval (HIER) using citrate-based (pH6.0) and EDTA-based (pH9.0) retrieval solutions; negative controls were at ambient temperature. The primary antibody was incubated for 15 minutes and signal visualized using the Bond Polymer Refine Detection kit (DS9800) with DAB Enhancer (AR9432) and haematoxylin counterstain with a standard protocol. All reagents related to immunohistochemistry (IHC) on the Bond-III were purchased from Leica Biosystems, Newcastle Upon Tyne, UK. Stained sections were washed in water and sequentially taken through graded alcohols to xylene prior to mounting with xylene-based permanent mounting medium. The slides were reviewed and optimal conditions chosen based upon the criterion of background-free selective cellular labelling. J6M0 muIgG2a was taken forward for use on patient tissue samples at a dilution of 1/400 with HIER using citrate-based (pH6.0) retrieval solution for 20 minutes with 15 minute primary antibody incubation.

Dual staining for BCMA and BLIMP-1 (clone ROS195G) (CNIO, Madrid, Spain) was also performed on the Bond-III platform. IHC for BCMA was performed as for single staining with omission of the haematoxylin counterstain. Immediately following visualisation of BCMA an additional HIER step with the EDTA-based (pH9.0) solution for 20 minutes was performed with subsequent applications of anti-BLIMP-1 supernatant at a 1/4 dilution for 2×45 minutes. Signal was detected using the Bond Polymer Refine Red Detection kit (DS9390) and visualized with Vector Blue Alkaline Phosphatase Substrate Kit (SK-5300, Vector Laboratories, Peterborough, UK) incubating for approximately 5 minutes. Slides were washed in Bond Wash and distilled water prior to dehydration through clean graded alcohols, air drying and mounting with VectaMount permanent mounting medium (H-5000, Vector Laboratories, Peterborough, UK).

Example 6—Investigation of Receptor Dynamics Following Antibody Binding

Confocal microscopy was used to visualise internalised antibody. Aliquots of H929 cells were incubated with S336105A07, washed, and incubated for various timepoints before incubation with J6M0 to detect newly expressed surface BCMA. Cells were then permeabilized and incubated with secondary antibodies before imaging on a Zeiss LSM510 Meta confocal microscope. Flow cytometry using J6M0-MMAF and J6M0 was used to assess changes in surface BCMA.

Confocal Microscopy.

H929 cells were incubated in 200 µl of RPMI 1640/1% FCS and 10 µg/ml murine anti-BCMA antibody (GSK, S336105A07) at 37° C. for 15 minutes, washed twice in PBS, plated on 12 mm round Poly-L Lysine coated coverslips (BD), fixed with 4% paraformaldehyde (PFA) (Sigma) for 10 minutes before secondary stain with goat anti-mouse Alexa 488 (Invitrogen) at 10 µg/ml in PBS/1% BSA for 1 hour at room temperature (RT). Plated cells were then washed in PBS, mounted with Prolong Gold with DAPI (Invitrogen) and imaged on a Zeiss LSM510 Meta confocal microscope.

To assess BCMA internalization and re-expression overtime, aliquots of H929 cells initially stained with murine antibody were washed, then resuspended in RPMI/1% FCS and incubated for varying timepoints, stained with J6M0 (10 µg/ml) and fixed. Following permeabilization with 0.1% Triton (Sigma), and blocking with PBS/1% BSA, cells were incubated with a mix of 0.5 µg/ml goat anti-mouse Alexa 488 (Invitrogen), 0.5 µg/ml goat anti-human Alexa 568 (Invitrogen), and 4 µg/ml Rabbit anti EEA (Calbiochem) for 1 hour at room temperature. Finally, after washing, cells were incubated in 0.5 µg/ml goat anti-rabbit Alexa 633 (Invitrogen) for 1 hour at room temperature, washed and mounted. Time points reported refer to period from first antibody to fixing, and accounting for time to prepare cells as outlined, aliquots cultured for 0 or 6 hours after initial murine antibody assessed BCMA at 1 and 7 hours, respectively.

Flow Cytometry.

$1 \times 10^6$ H929 cells received a single dose of J6M0-MMAF or J6M0 in RPMI/10% FCS for 15 minutes or 2 doses of 10 µg/ml at 0 and 24 hours. Cells were washed twice and resuspended in growth media and at timepoints, aliquots of incubated cells were fixed in 1% PFA and stained with 1 µg/ml of anti-human IgG APC (Southern Biotech). To assess the contribution of de novo protein synthesis to surface BCMA re-expression, cycloheximide (10 or 100 µg/ml) was included during the incubations before secondary staining.

Example 7—Measurement of Soluble BCMA Levels

Levels of soluble BCMA (sBCMA) were measured by Meso-Scale Discovery (MSD) immunoassay. In brief, 96-well high bind plates (MSD, L15XB-3) were solution coated with 25 µL/well of 3 µg/mL J6M0-wtFc monoclonal antibody in PBS (Gibco) and incubated overnight at 2-8° C. Plates were washed 3×175 µL/well with PBS+0.05% Tween 20 and blocked with 25 µl/well of diluent #2 (MSD, R51BB) for 30 minutes at room temperature on a shaker set to 600 revolutions per minute (rpm). A BCMA standard curve was prepared using human BCMA extracellular domain (1-53) protein (GSK) from 0.1 to 100 ng/mL in BCMA depleted pooled human serum (GSK). Twenty-five microliters per well of standards or serum samples were added to plates and incubated for 1 hour as described previously. Plates were washed as described above followed by addition of 25 µL/well of 3 µg/mL biotinylated polyclonal goat anti BCMA antibody (R&D) and 3 µg/mL sulfo-TAG streptavidin (MSD) in PBS 1% BSA (Sigma). Plates were incubated for 1 hour as described previously. After further washes, 150 µL/well of 1×MSD read buffer T (MSD) diluted in MQ water was added. Plates were read on an MSD Sector Imager 6000 within 15 minutes.

Example 8—Cytotoxicity Assays

HMCL were cultured with J6M0-MMAF and viable cell number determined using AnnexinV-FITC/PI (BD) and flow cytometry (BD Facsverse) with Flow-Check Fluorospheres (Beckman-Coulter). For primary BM CD138+ cells, whole MNCs were incubated with J6M0-MMAF in RPMI and 20% pooled myeloma patient plasma (Quinn et al., 2011), and viable MM cells were enumerated by staining with CD138-APC (Miltenyl) followed by flow cytometry using AnnexinV-FITC/PI as above. To assess MM progenitor killing, HMCL were cultured with J6M0-MMAF, and aliquots removed for clonogenic assays in metho-cellulose (MethoCult, Stemcell Technologies). Colonies were enumerated after 14 days culture at 37° C.

Statistical Tests

P values <0.05 were considered significant. Statistical tests used as indicated and were calculated using Prism version 6.0 (Graphpad Software).

Example 9—Expression of BCMA on Malignant Plasma Cells

Figure 1B:
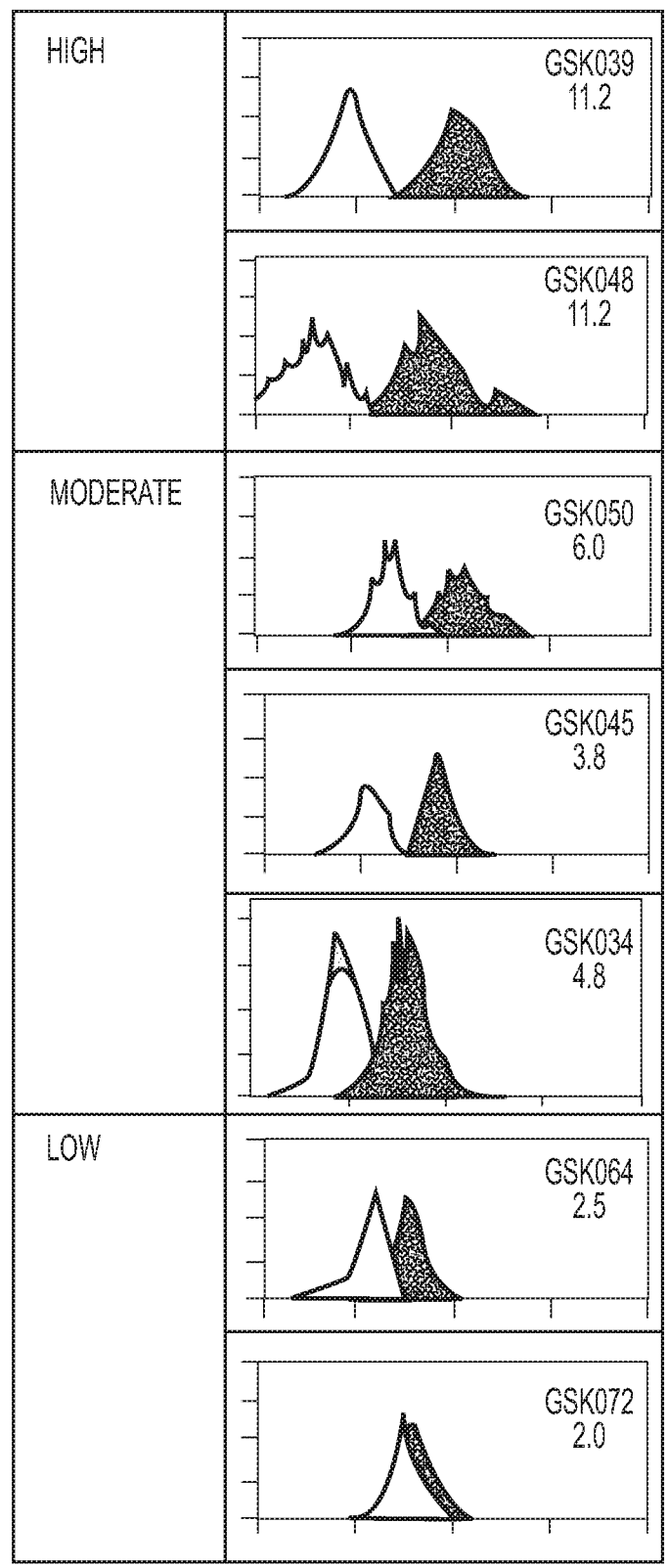
Figure 1C:
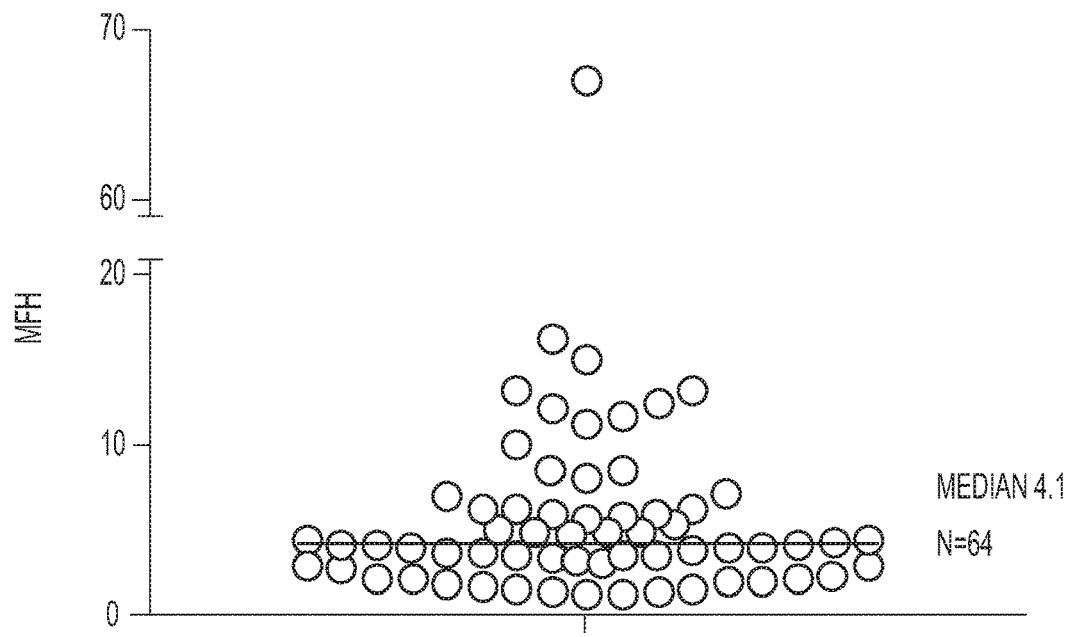
Figure 1D:
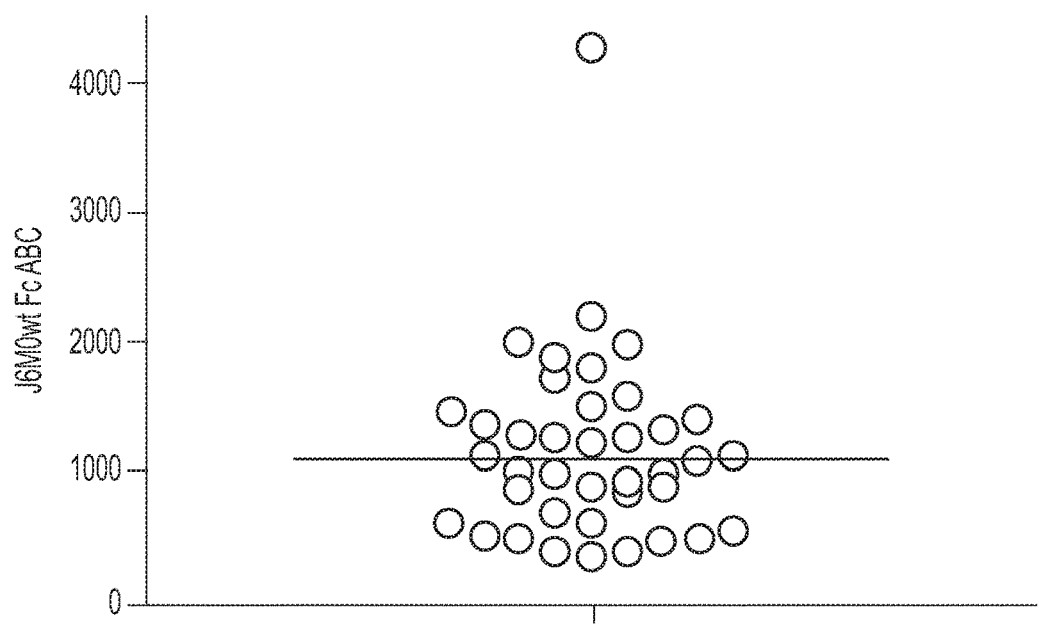
Figure 2A:
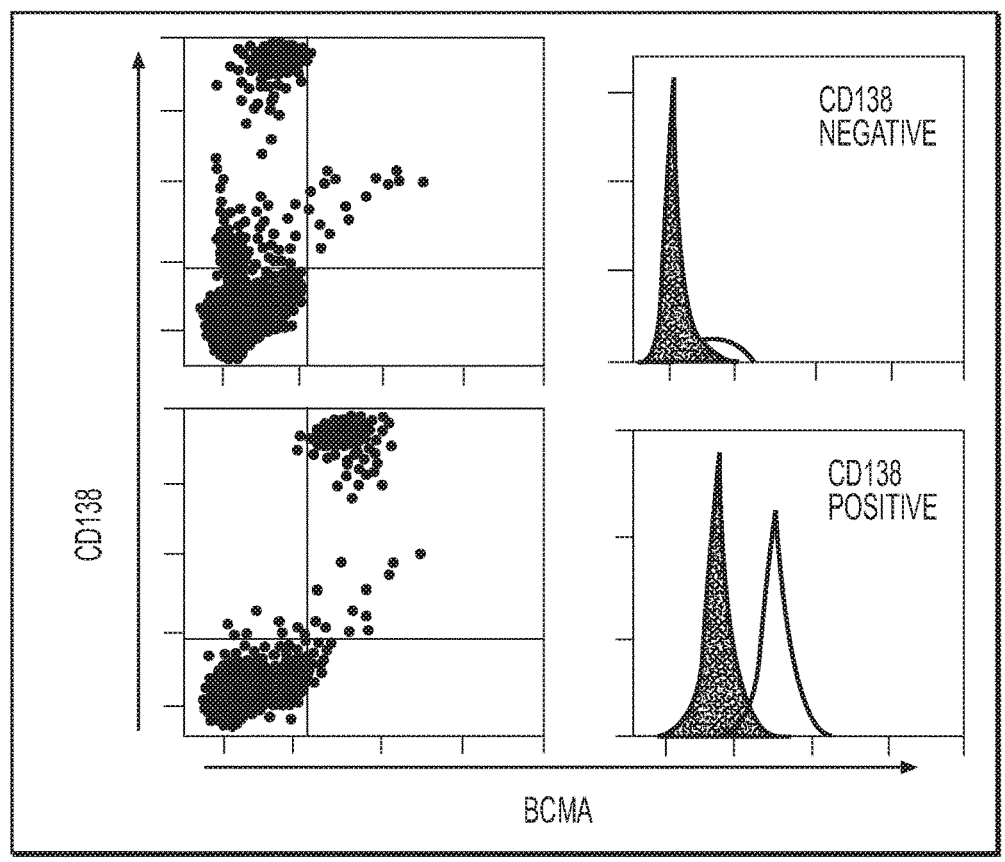
FIG. 2: BCMA expression and bone marrow MNCs. (A) CD138+ cells in patient BM have higher surface BCMA levels, compared to CD138− cells (top panel), and other cell subsets (CD45+ CD138− or CD45−CD138−, lower panel). (B) BM MNCs were incubated with FITC-conjugated anti-BCMA (S307118G03), together with anti CD138 APC and anti CD56 PE, anti CD20 PB or anti CD28 PB and analysed by flow cytometry. CD138+ cells co-expressing CD56 (i), CD20 (ii) or CD28 (iii), were gated for analysis of BCMA expression (right panels, filled histograms, BCMA, open histograms, isotype control).
Figure 2A:
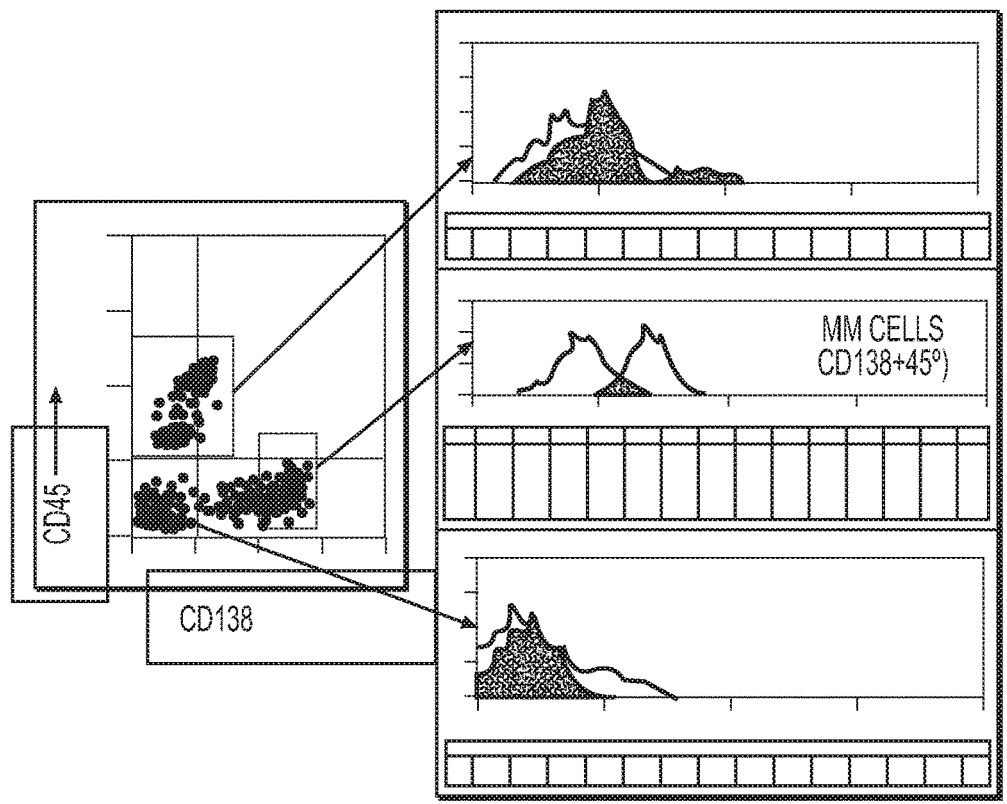
Figure 2B:
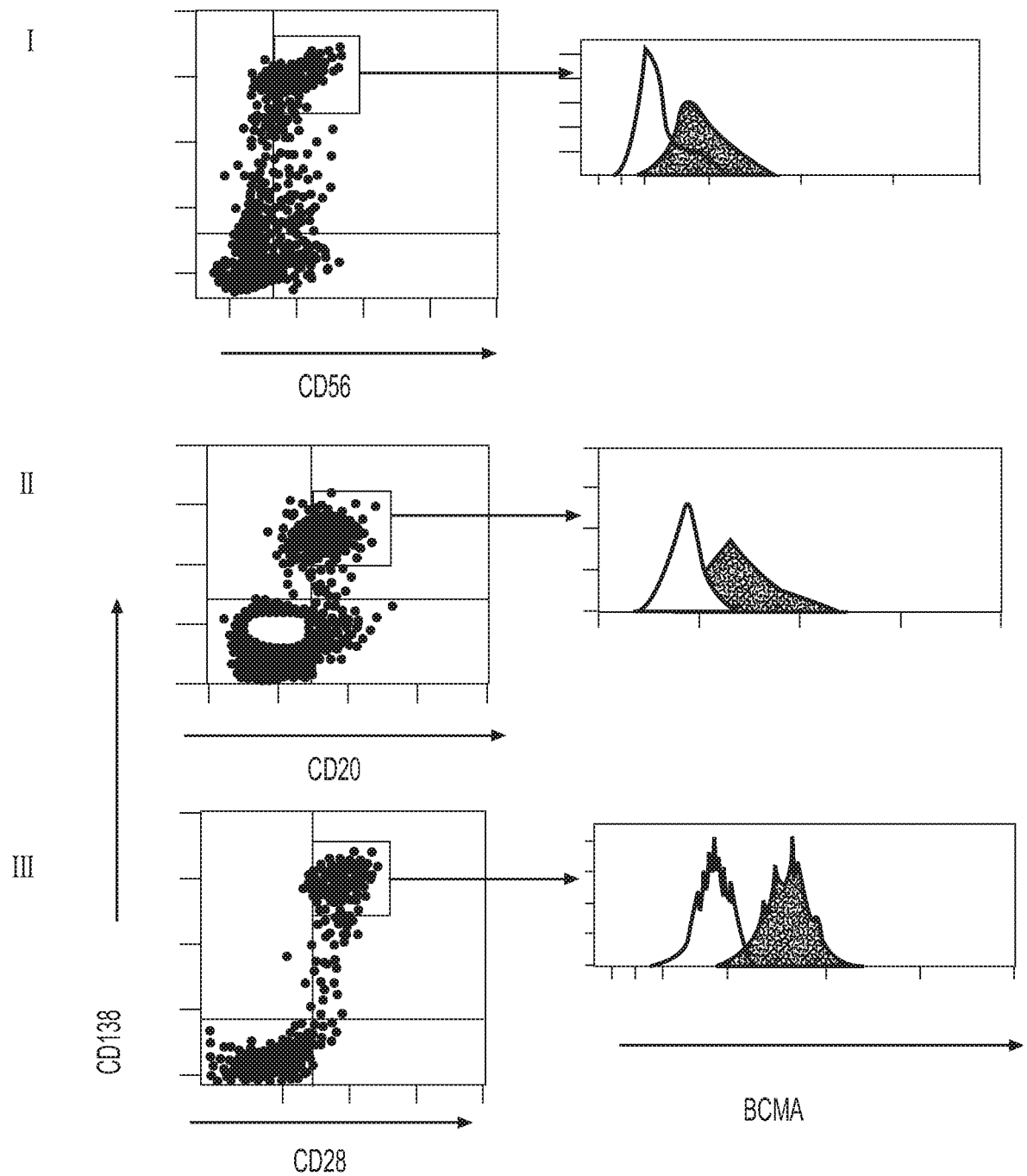

HMCL expressed varying levels of surface BCMA, with high levels on H929, MM1.s and JIM3, compared with low expression on KMM1. Non-MM cell lines were negative (SupT1, Raji) or low (Daudi) by flow cytometry (FIG. 1A). BM MNCs from 64 patients were assessed for BCMA expression by flow cytometry, gating on the CD138+ population. Primary MM cells also varied in their surface antigen levels, ranging from uniformly high, to low/negative expression (FIG. 1B). BCMA MFI ratios ranged from 1 to 67 (FIG. 1C). Quantibrite beads (BD) were used to assess number of antibodies bound per cell (ABC) in 39 patients. The results confirm variation in receptor density (median 1084.9, range 348.7-4268.4 ABC, FIG. 1D). CD138− cells in the BM did not express BCMA (FIG. 2A). The inventors observed that co-expression of surface BCMA with other MM antigens, including CD28, CD20, and CD56, found no correlation with MM surface phenotype (FIG. 2B).

Of the 70 patients in the inventors' cohort, 64 patients had BM trephines available for immunohistochemistry (IHC). Double staining for BLIMP1 was used to identify PC (FIGS. 3A-D). BLIMP1 is a transcription factor that controls plasma cell differentiation (Honey, 2003), and appears critical for the survival of normal and malignant PC (Lin et al., 2007). Furthermore, staining for BLIMP1 identifies the CD138+ plasma cell compartment in MM bone marrow (FIG. 4) (Cattoretti et al., 2005). The nuclear location of this antigen facilitates the visualisation of cytoplasmic and membrane BCMA, While both surface and intracellular protein was demonstrated in all cases, some variation in antigen density as well as proportion of BCMA positive PC was seen (FIG. 4A). Bone marrow samples were given a BCMA/BLIMP1 score of 0-5 according to the proportion of MM cells staining positive for BCMA, as detailed above. There was broad correlation between the IHC score and the MFI ratio as determined by flow cytometry (Table 2).

TABLE 2

Summary of clinical correlates according to BCMA/BLIMP1 score

| | | BCMA/BLIMP1 Score | | |
|---|---|---|---|---|
| | | 1 | 2-3 | 4-5 |
| Number N | | 16 | 30 | 18 |
| BCMA expression by Flow Cytometry Median MFI ratio, range | | 3.9, 1.0-12.1 | 4.1, 1.0-13.2 | 4.9, 1.5-67.0 |
| Age Median, range | | 65, 28-82 | 65, 44-83 | 61, 41-72 |
| Sex n (%) | M | 11 (68.8%) | 22 (73.3%) | 11 (61.1%) |
| | F | 5 (31.3%) | 8 (26.7%) | 7 (38.9%) |
| Disease state n (%) | D | 6 (37.5%) | 9 (30%) | 5 (27.8%) |
| | R | 10 (62.5%) | 21 (70%) | 13 (72.2%) |
| Cytogenetic risk n (%) | Standard | 9 (56.3%) | 10 (33.3%) | 6 (33.3%) |
| | Poor | 6 (37.5%) | 20 (66.7%) | 12 (66.7%) |
| | NA | 1 (6.3%) | 0 | 0 |
| Isotype n (%) | IgG | 9 (56.3%) | 19 (63.3%) | 13 (72.2%) |
| | IgA | 2 (12.5%) | 10 (33.3%) | 1 (5.6%) |
| | IgD and LC | 5 (31.3%) | 1 (3.3%) | 4 (22.2.7%) |
| Follow up Median months, range | | 29, 4-38 | 24, 1-38 | 17, 2-38 |
| Response to treatment n (%) | CR/PR | 9 (56.3%) | 17 (56.7%) | 6 (33.3%) |
| | Less than PR | 6 (37.5%) | 12 (40%) | 12 (66.7%) |
| | NA | 1 (6.3%) | 1 (3.3%) | 0 |
| PFS Median months | | 13.5 | 12 | 6 |
| OS Median months | | NR | NR | 18 |

Table 2 legend:
M: male;
F: female;
D: diagnosis;
R: relapse;
NA: not available/applicable;
CR/PR: complete/partial response;
PR: partial response;
PFS: progression free survival;
OS: overall survival;
NR: not reached.

Figure 3A:
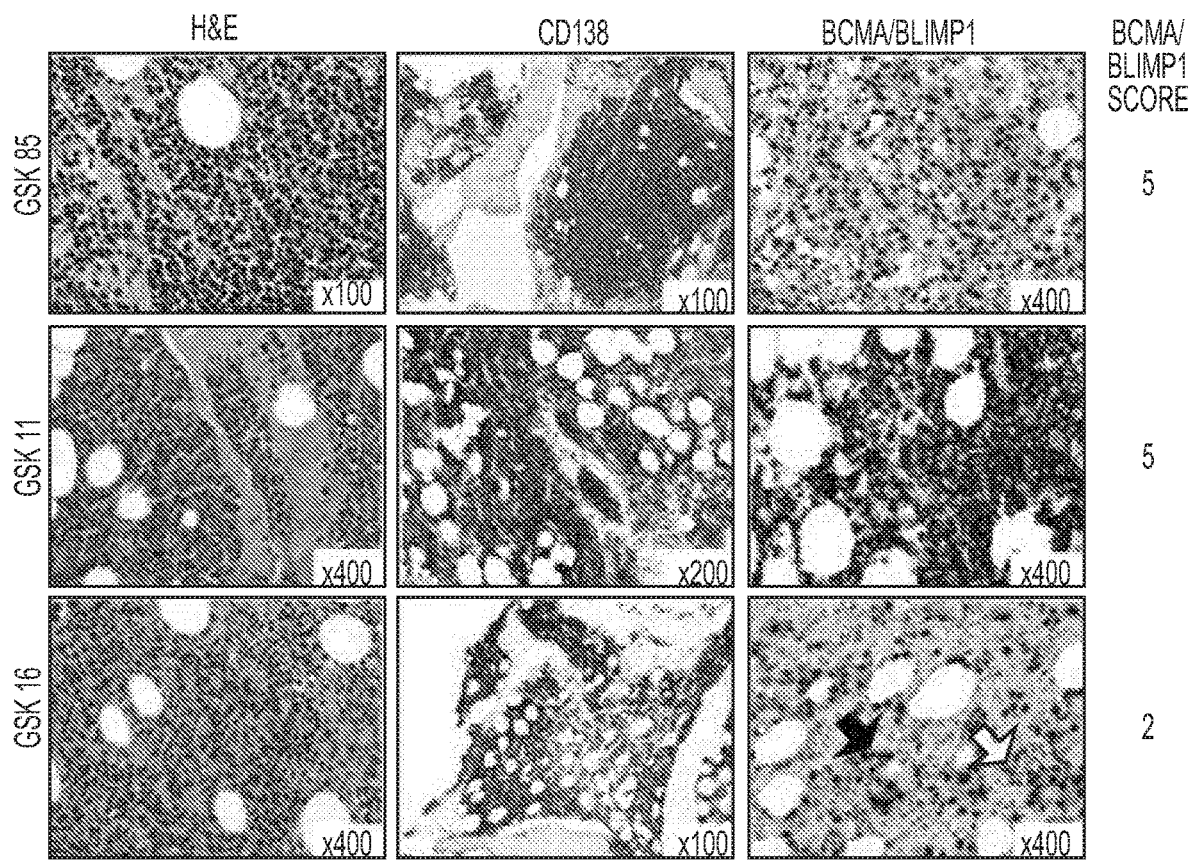
FIG. 3: BCMA expression by IHC. (A) IHC staining of bone marrow trephines from myeloma patients. In the BCMA/BLIMP1 panels, BLIMP1 (nuclear) staining is seen as blue, and BCMA (cytoplasmic and membrane) as brown. GSK 85 and 11 are examples of uniform BCMA expression. GSK 16 shows patchy BCMA expression with areas of BCMA positive (black arrow) and BCMA negative plasma cells (white arrow). BCMA expression as determined by BCMA/BLIMP1 score indicated. H&E, haematoxylin and eosin. (B) IHC staining of sequential samples from three myeloma patients showing BCMA expression in sequential samples at different disease stages. D diagnosis, R1 first relapse, R2 second relapse, PD progressive disease. (C) IHC from a patient in second relapse of IgA multiple myeloma with a hepatic extramedullary plasmacytoma and corresponding bone marrow trephine showing retained BCMA expression with extramedullary involvement. (D) IHC of bone marrow trephines from myeloma patients post therapy revealing BCMA expression on residual plasma cells. The first patient with lambda light chain myeloma was in first plateau phase 6 months post ASCT and the second was in first plateau phase post chemotherapy.
Figure 3B:
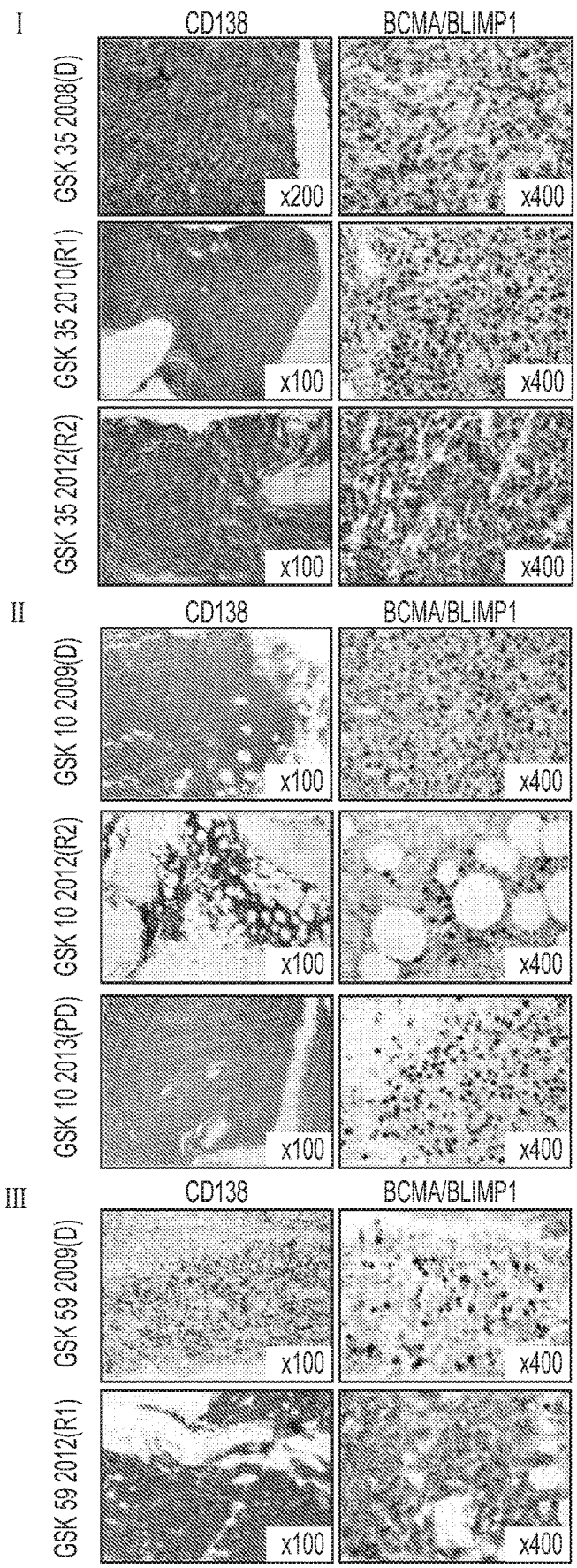
Figure 3C:
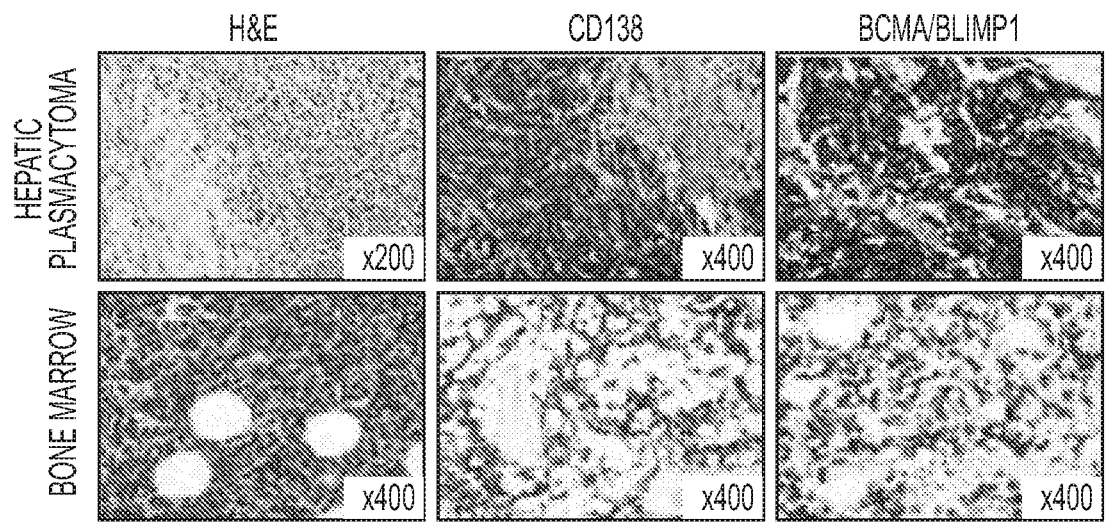
Figure 3D:
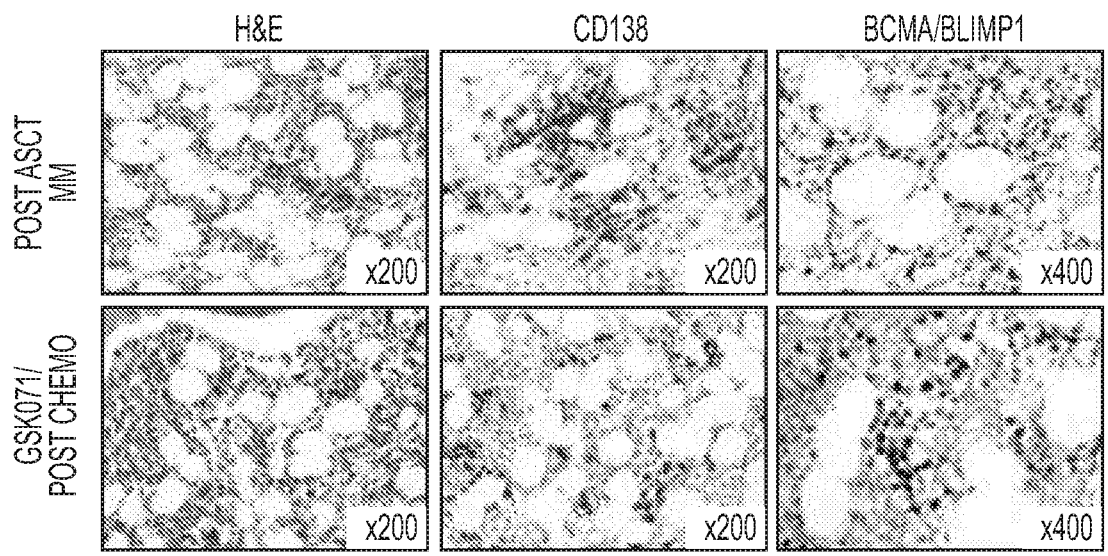
Figure 4:
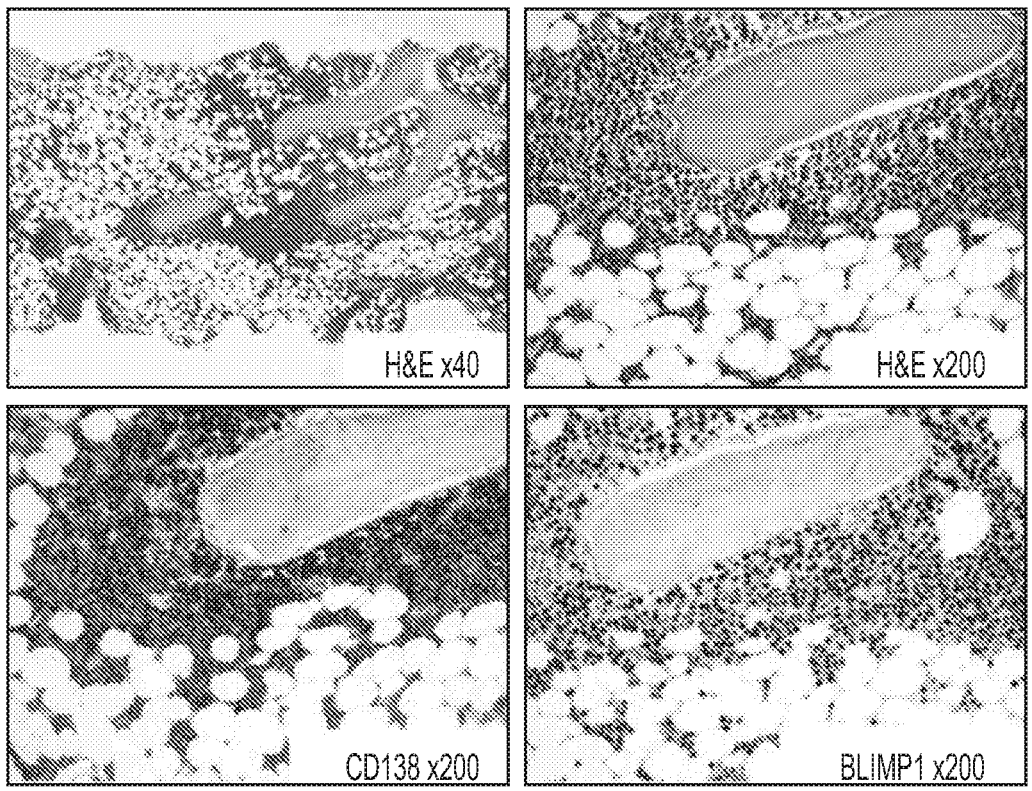
FIG. 4: BLIMP1 staining correlated to CD138 on IHC. Bone marrow trephines were routinely stained with H&E and CD138 to identify plasma cells prior to dual staining with BCMA/BLIMP1. As demonstrated, there was good and consistent correlation between CD138 and BLIMP1 staining.
Figure 5:
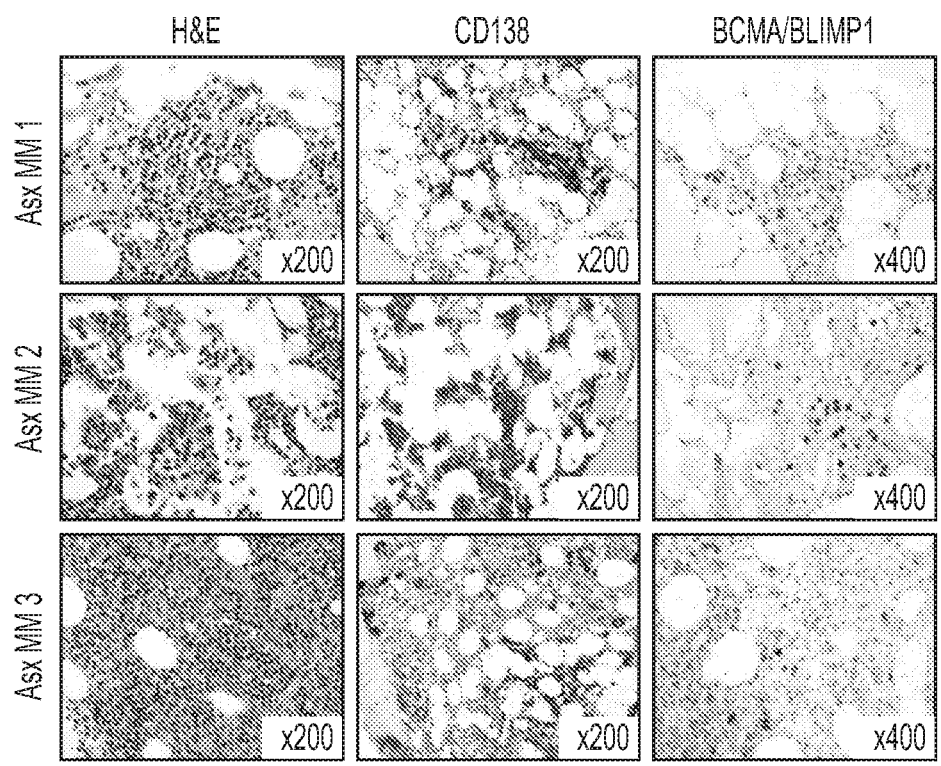
FIG. 5: IHC of bone marrow trephines from patients with asymptomatic myeloma. BCMA/BLIMP1 score of 0 seen on IHC of BM trephines from 3 patients with asymptomatic myeloma.
Figure 6:
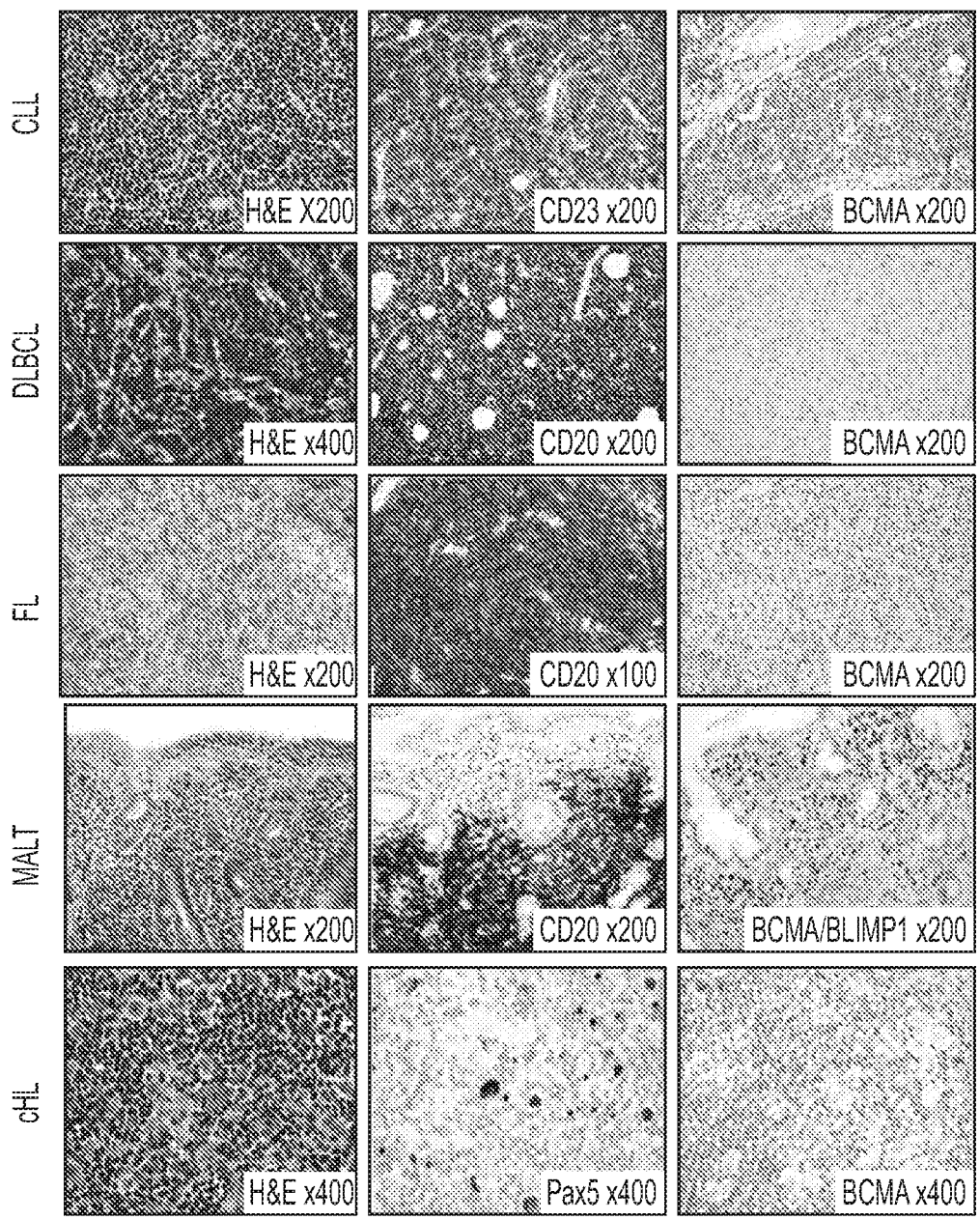
FIG. 6: IHC of B cell malignancies. BCMA expression absent in chronic lymphocytic leukemia (CLL), diffuse large B cell lymphoma (DLBCL) and follicular lymphoma (FL) but present on plasma cells in mucosal associated lymphoid tissue (MALT) and classical Hodgkin Lymphoma (cHL) where it is clear that BCMA expression is absent on tumour cells themselves.
Figure 7:
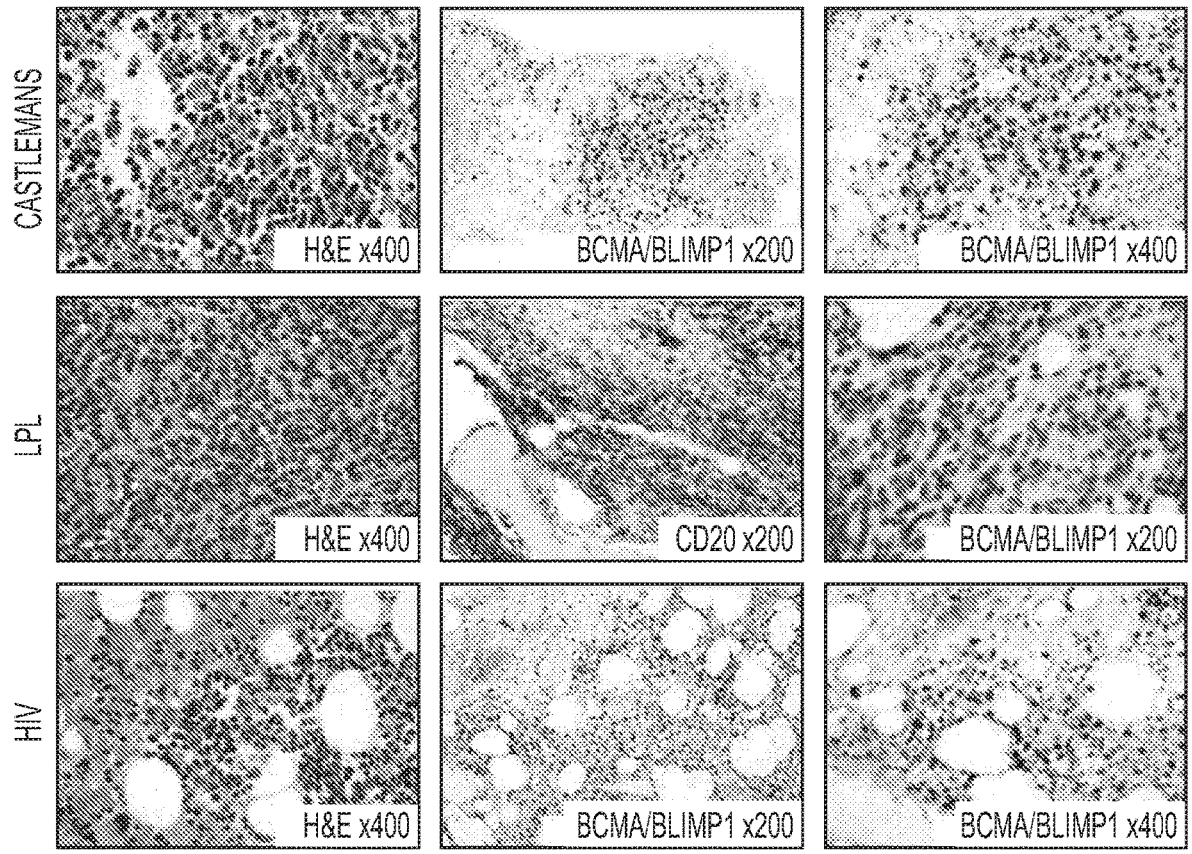
FIG. 7: IHC of plasma cell containing neoplasms. Weak BCMA staining is seen in Castlemans disease, Lymphoplasmacytic lymphoma (LPL), and polyclonal plasmacytosis in bone marrow from an HIV patient.

In a small series of patients with sequential BM samples, the inventors observed that BCMA expression persisted through several relapses (FIG. 3B). High BCMA expression was seen in extramedullary plasmacytomas, correlating with levels in medullary tumour (FIG. 3C). It was also observed that in patients in stable plateau phase following autologous stem cell transplant (ASCT) or chemotherapy, residual MM cells remained BCMA positive (FIG. 3D), while tumour cells from patients with smouldering/asymptomatic MM had low level/negative expression (FIG. 5). In contrast, most B-cell lymphomas, including chronic lymphocytic lymphoma (CLL), follicular lymphoma (FL) and diffuse large B cell lymphoma (DLBCL), showed no expression of BCMA (FIG. 6). Exceptions were the PC in Castleman's disease, that showed weak staining, and in lymphoplasmacytic lymphoma (LPL), where CD138+, but not CD20+, cells were weakly positive for BCMA (FIG. 7).

Figure 8:
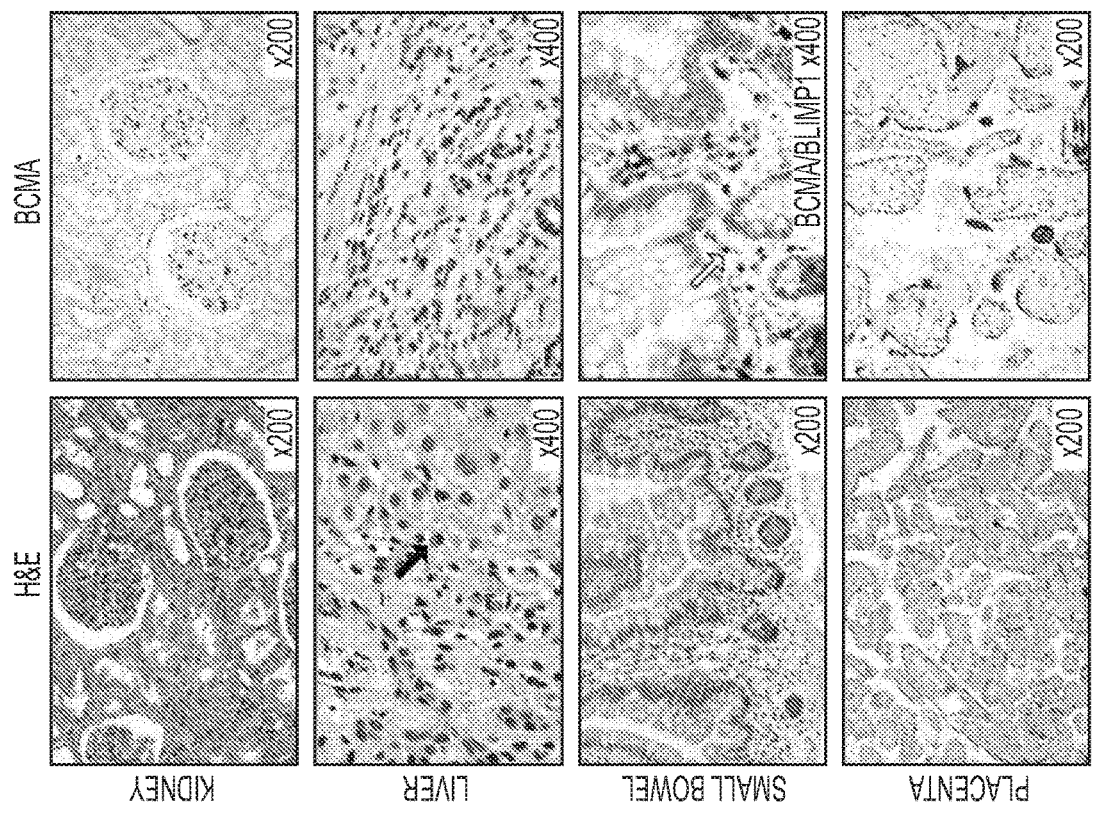
FIG. 8: IHC of normal tissues. BCMA expression is seen in plasma cells in liver from patient with viral hepatitis (plasma cell seen on H&E and on BCMA stain, black arrow) and plasma cells in lamina propria of small bowel (white arrow).
Figure 8:
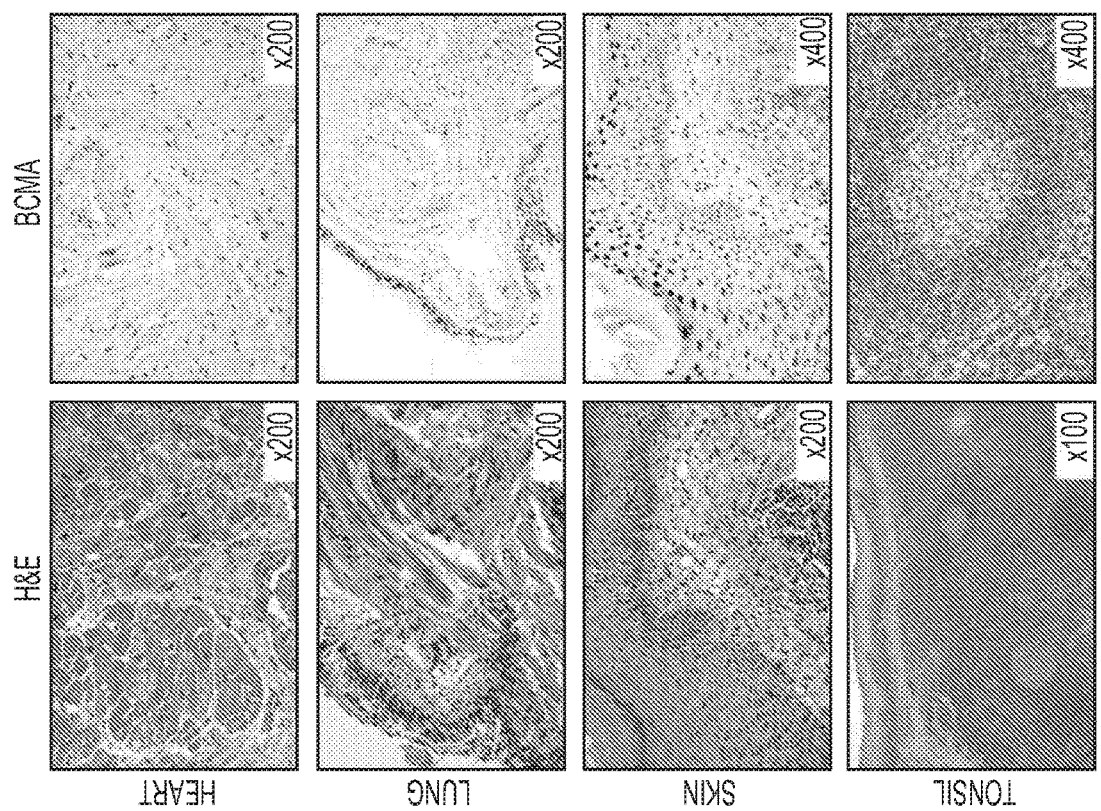

BCMA expression was investigated in non-neoplastic plasmacytoses; BM PC from HIV-positive patients displayed low level BCMA expression (FIG. 7). To understand the distribution of BCMA expression in non haemopoietic tissue, a large number of normal tissues were stained, and no BCMA expression in heart, lung, kidney, tonsil and placenta was found. In the gastro-intestinal tract, BCMA expression was confined to PC in lamina propria of small bowel (FIG. 8). PC in liver sections from a patient with viral hepatitis also expressed BCMA (FIG. 8).

Example 10—Soluble BCMA Levels

Figure 9A:
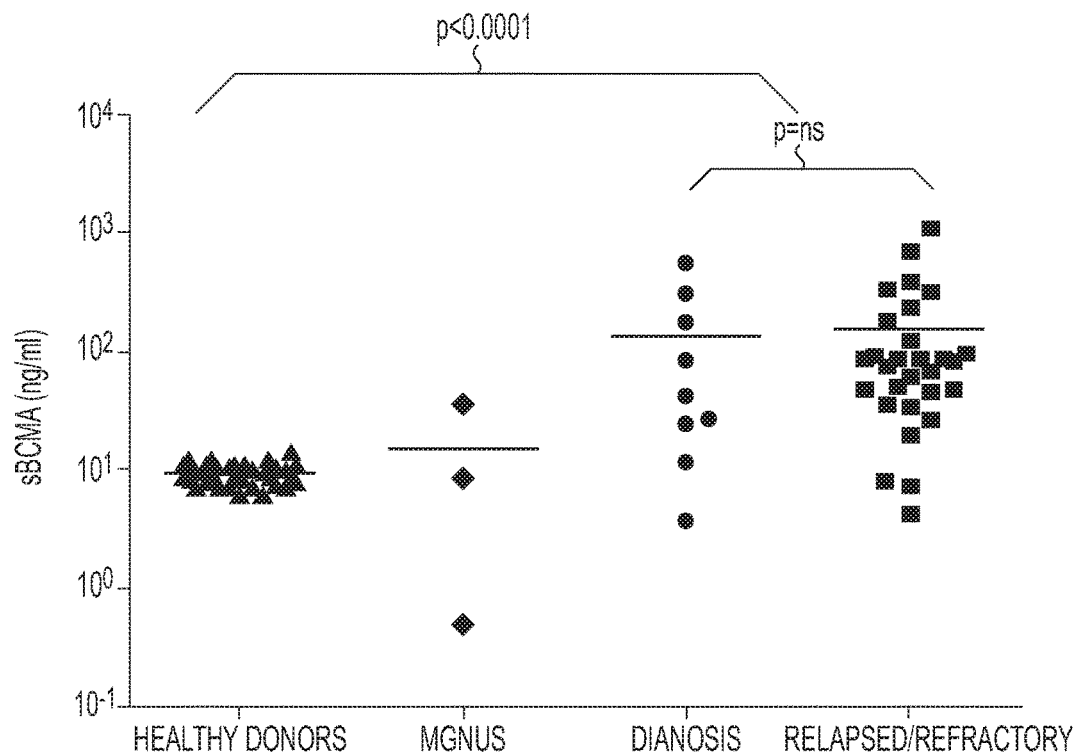
FIG. 9: Soluble BCMA compared to disease stage and tumour BCMA expression. A total of 42 patients had soluble BCMA (sBCMA) levels for analysis (3 with monoclonal gammopathy of uncertain significance, 1 asymptomatic MM, 38 with symptomatic MM). (A) sBCMA levels in healthy donors, MGUS, new MM diagnosis and relapsed or refractory MM with means indicated. Healthy donors (n=38, mean=9.3), MGUS (n=3, mean=15.2), new diagnosis (n=9, mean=134.8.2), relapsed or refractory MM (n=29, mean=154.5). There was no statistical difference between healthy donors and patients with MGUS or new diagnosis of myeloma and relapsed patients (p>0.05 by Mann-Whitney U for both). However, sBCMA level of all patients with symptomatic myeloma was greater than that in healthy donors (p<0.0001 by Mann Whitney U). (B) There is a positive correlation between sBCMA and the product of %
Figure 9B:
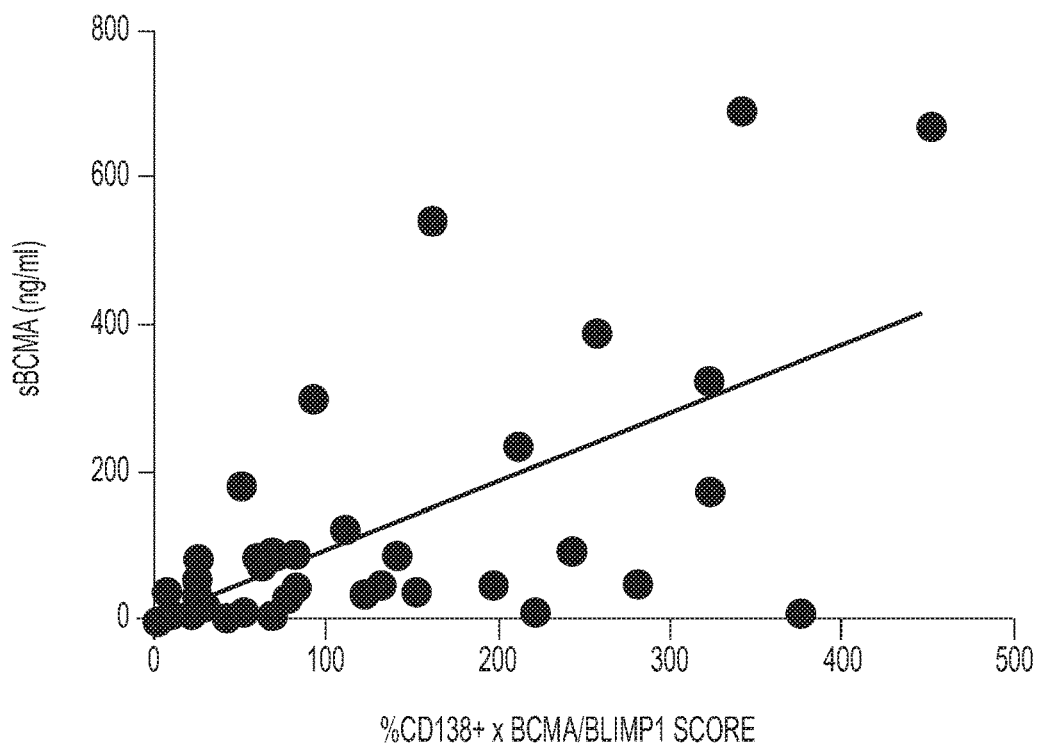

A subset of patients had sera available for soluble BCMA (sBCMA) measurements. In patients with MM, circulating BCMA levels ranged from 3.8-1062 ng/ml (FIG. 9). MM sera also contained higher levels of BCMA compared with normal controls ($p<0.0001$), with no difference observed between newly diagnosed patients and those with relapsed disease (FIG. 9A), even when adjusting for percentage of CD138+ cells in bone marrow. To investigate the correlation of bone marrow BCMA expression with circulating soluble antigen, a composite score of bone marrow plasmacytosis (% CD138+ cells) and BCMA expression level (BCMA/BLIMP1 score) was used. In 40 patients with both sBCMA and a bone marrow trephine available, serum BCMA levels correlated positively with the product of % CD138+ cells in BM and the BCMA/BLIMP1 score ($r^2=0.37$, FIG. 9B).

Example 11—Correlation of BCMA Expression with Disease Characteristics

In the patient cohort summarised in Table 3, the possible association of BCMA expression on MM cells with clinical and disease parameters was investigated, using the IHC score (BCMA/BLIMP1 score) for simplicity. There was no correlation of BCMA expression with patient demographics, disease stage (i.e. new diagnosis vs. relapse), cytogenetic risk, disease isotype or response to next line of treatment (Table 2).

TABLE 3

Summary of poor risk cytogenetics in patient cohort.

| Poor Prognostic Lesion | n (%) |
| --- | --- |
| t (4;14) | |
| with 1q+ | 6 (8.6%) |
| with 17p− | 1 (1.4%) |
| with both | 2 (2.8%) |
| t (14;16) | |
| with 1q+ | 1 (1.4%) |
| with 17p− | 1 (1.4%) |
| 1p−/1q+ | 18 (25.7%) |
| 17p− (>50%) | 7 (10%) |
| 1p−/1q+ with 17p− | 3 (4.3%) |
| Complex-hypoploid | 1 (1.4%) |

Median follow up from time of BM biopsy was 24 months (range: 1-38). Median progression free survival (PFS) and overall survival (OS) were shortest in patients with a high BCMA/BLIMP1 score of 4-5 (6 and 18 months respectively compared to 13 months and median not reached for BCMA/BLIMP score 1-3, FIG. 10B). This difference was not statistically significant (p=0.52 for PFS and 0.19 for OS by log rank).

Figure 10B:
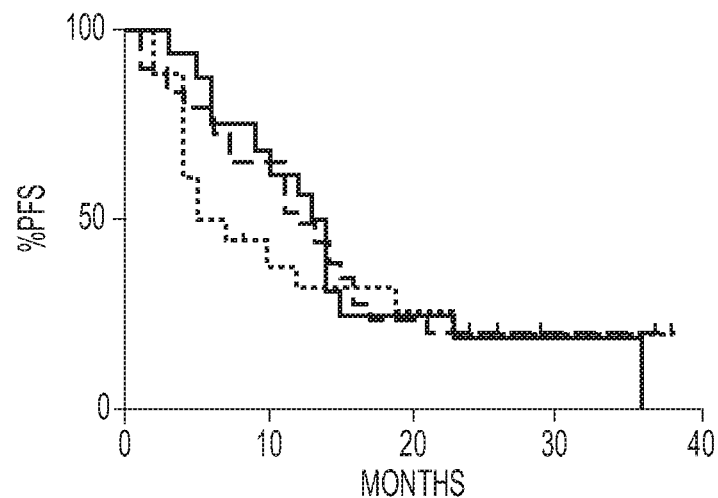
Figure 10B:
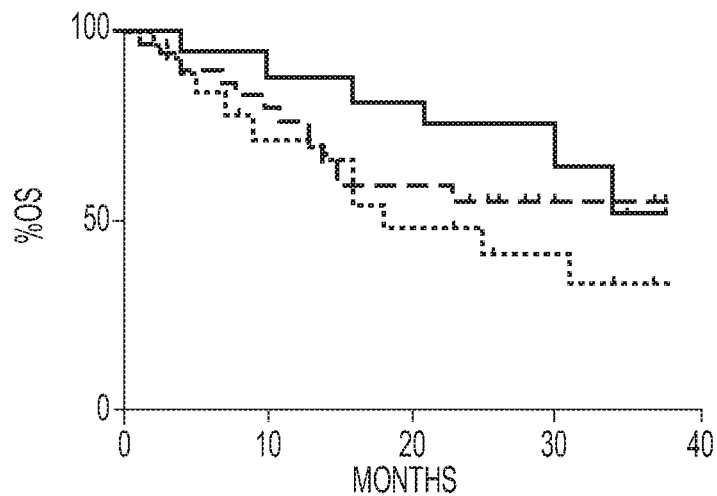
Figure 10C:
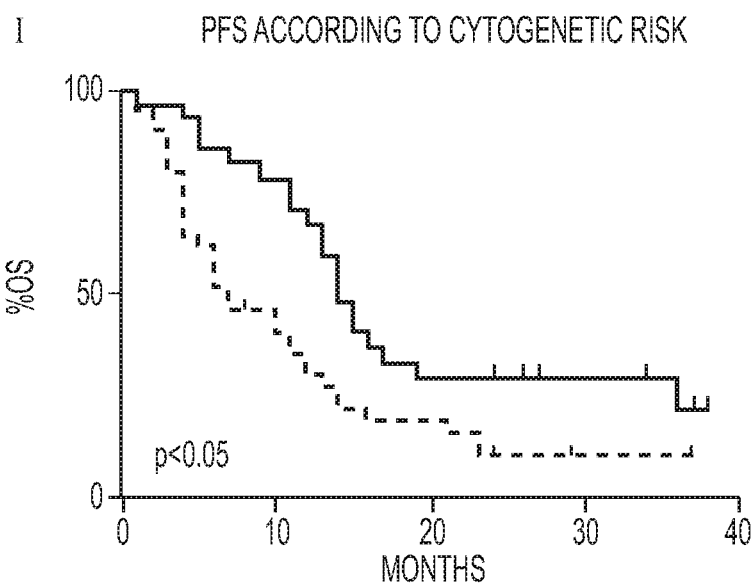
Figure 10C:
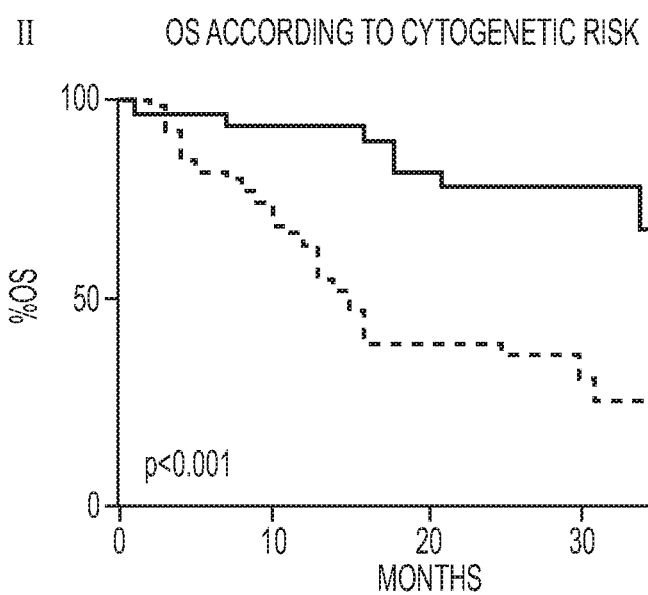
Figure 10D:
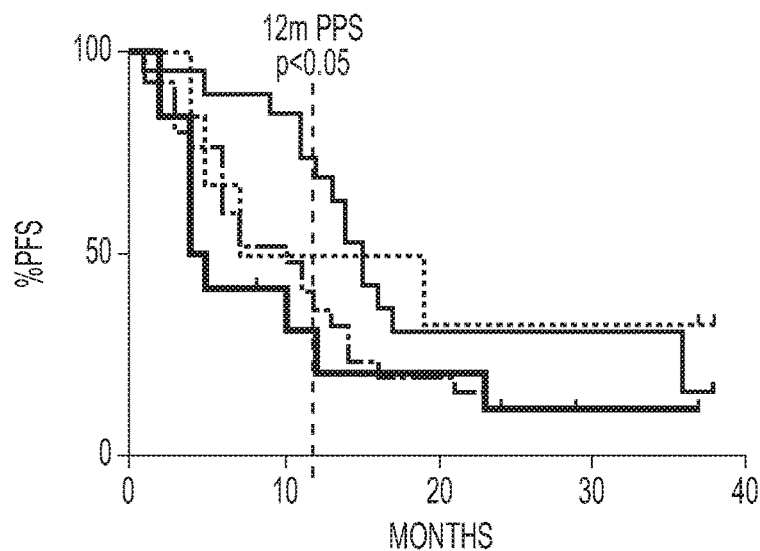
Figure 10D:
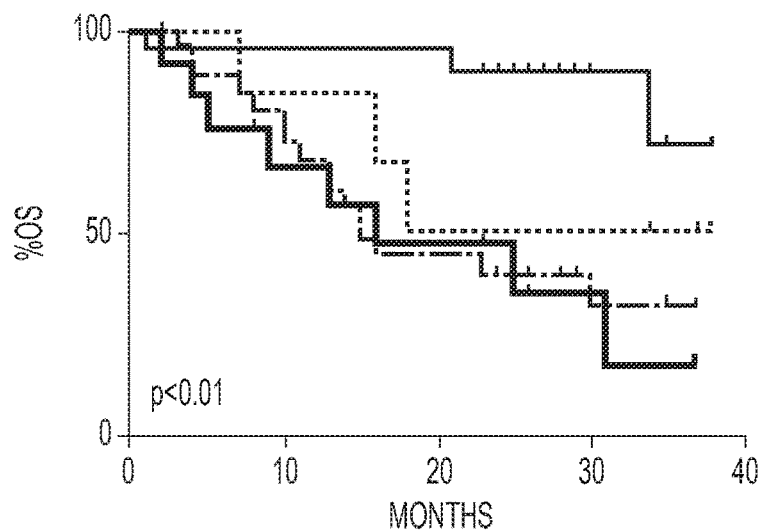

When PFS and OS were analysed by genetic risk, it was observed, as expected, a significantly shorter disease free and overall survival for patients with adverse FISH (median PFS 7 months vs. 14 for standard risk group, p<0.05 by log rank test, and median OS 15 months vs. NR, p<0.001, FIG. 10C). BCMA/BLIMP1 score appeared to provide additional prognostic information over and above the FISH results, such that patients could be risk stratified for early relapse and overall survival. Significantly, coexistent high BCMA levels (BCMA/BLIMP1 score 4-5) identified a small subgroup of patients with standard risk genetics who had earlier relapse and shorter survival. Patients with standard risk genetics and low BCMA (BCMA/BLIMP1 score 1-3), standard risk genetics and high BCMA, adverse genetics and low BCMA, or adverse genetics and high BCMA had a 12 month PFS of 68%, 50%, 36%, 20% (p<0.05 by log rank test) and an OS of NR, 28, 15, 16 months (p<0.01 by log rank test) respectively (FIG. 10D).

Example 12—BCMA Surface Receptor Dynamics and Re-Expression

Figure 11A:
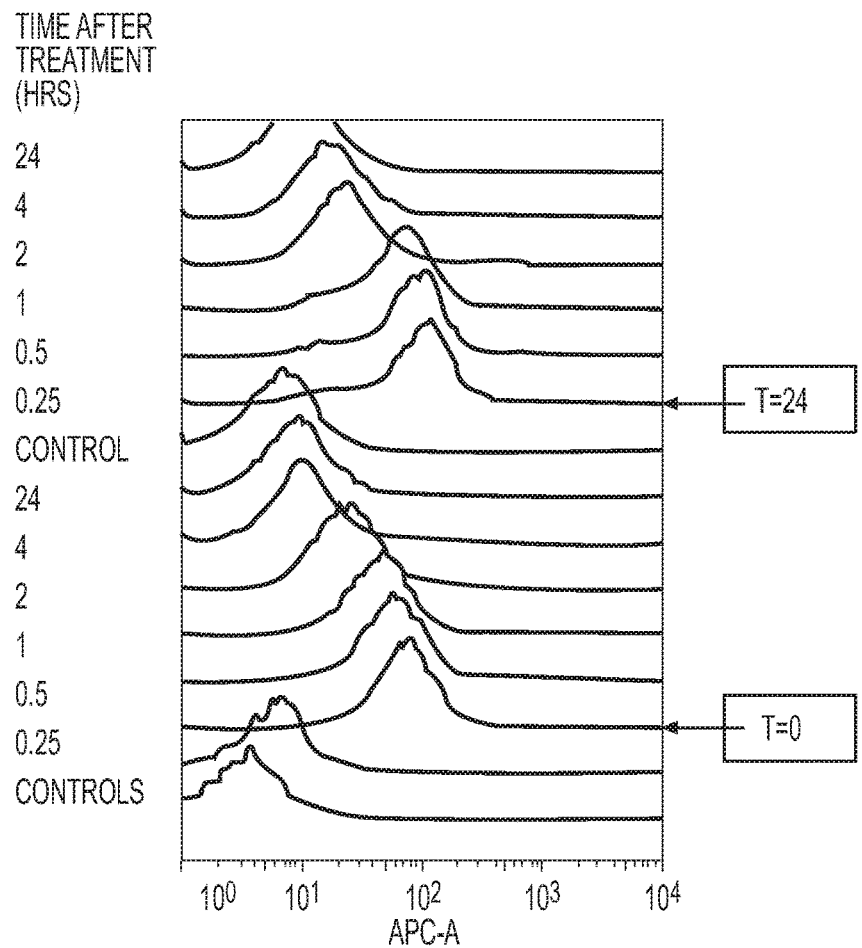
Figure 11B:
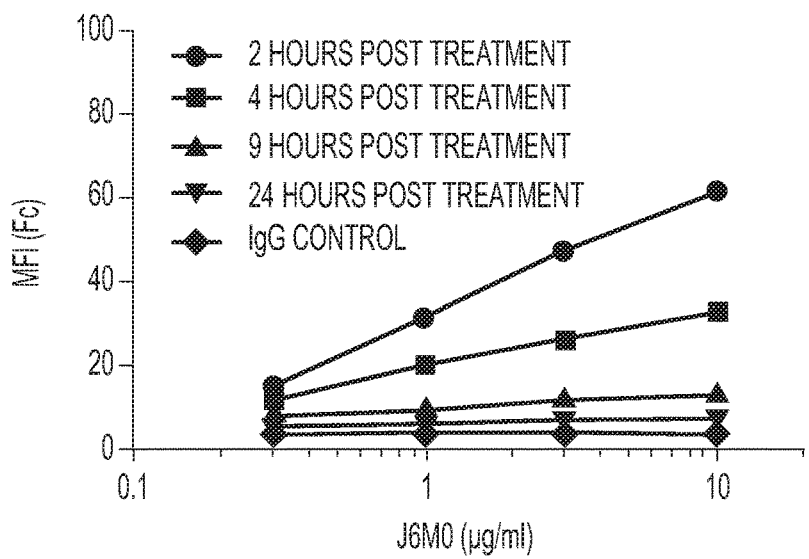

Given the variability in surface antigen density among patients and the demonstration of intracellular BCMA, the possibility that surface receptors are internalized and new, or re-cycled receptors expressed on the cell surface was investigated. When H929 MM cells were pulsed with a saturating amount of J6M0-MMAF for 15 minutes, washed and remaining surface bound antibody monitored by anti-human Fc staining at time points, surface BCMA/antibody complex decreased in a time dependent manner reaching undetectable levels by 24 hours. When a second saturating pulse of J6M0-MMAF was applied at 24 hours, this displayed a similarly rapid decline (FIGS. 11A-B).

Figure 11C:
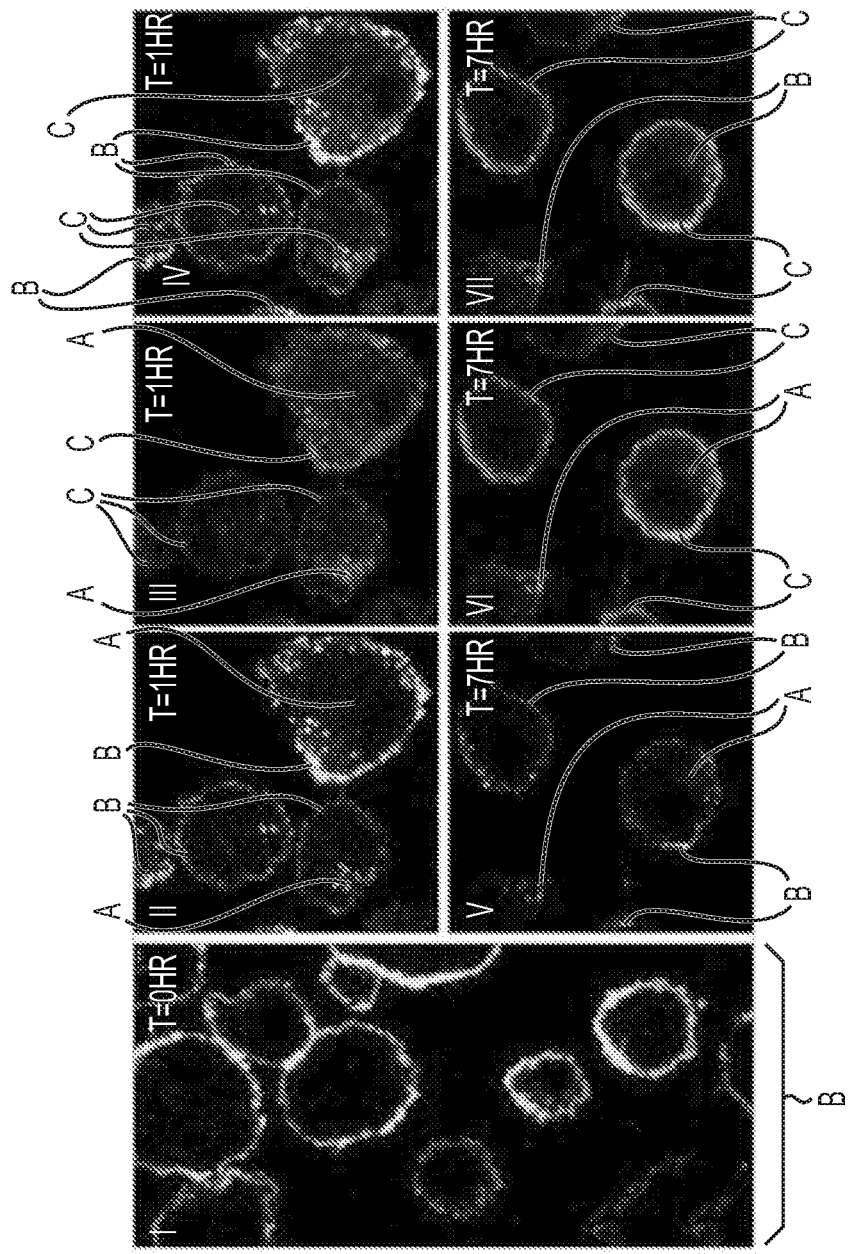
Figure 11D:
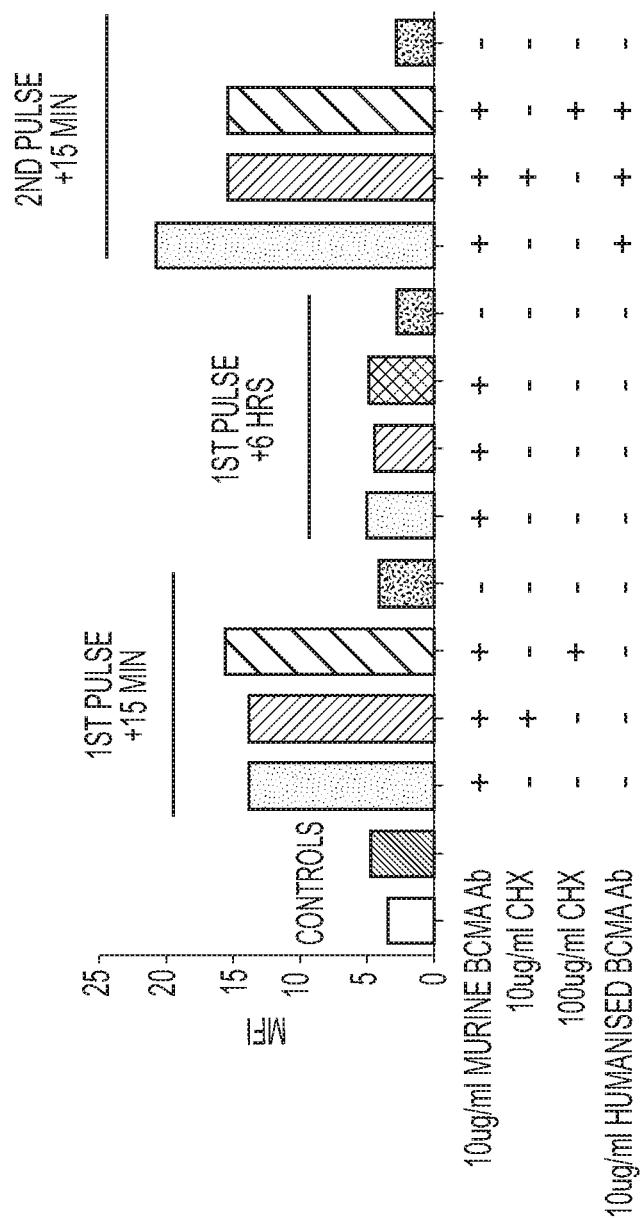

Confocal microscopy was used to track cell associated BCMA, as revealed by antibody binding. Following an initial pulse with S336105A07, surface BCMA decreased noticeably by 1 hour and continued to decrease for up to 7 hours. From 1 hour it was evident that at least some of this surface BCMA (green) was internalized and co-localized to endosomes labelled with anti EEA. In parallel, subsequent staining with J6M0 at intervals revealed newly expressed receptor on the cell surface from 1 hour (FIG. 11C, red). At least some of newly expressed surface BCMA is protein synthesis dependent, as indicated by experiments with cycloheximide (FIG. 11D). Internalisation of bound antibody with re-expression of re-cycled/newly synthesized protein on the cell surface provides a mechanism for J6M0-MMAF activity in the context of low level antigen expression. This hypothesis would also predict that tumour cells with low surface BCMA would require longer exposure to the antibody-drug conjugate for optimal cytotoxicity.

Example 13—Cytotoxicity of J6M0-MMAF on HMCL

Figure 12A:
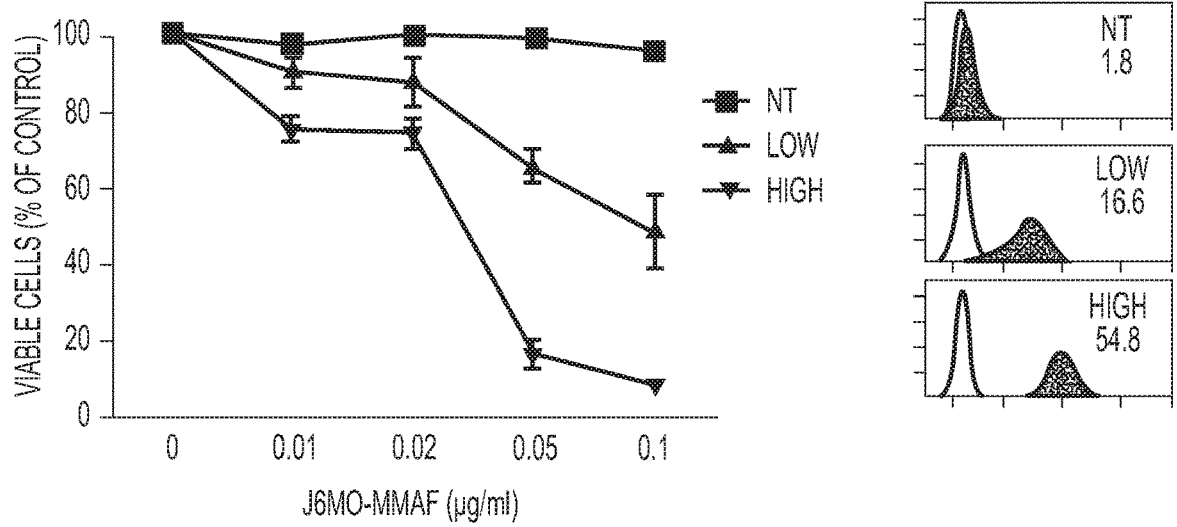
Figure 12B:
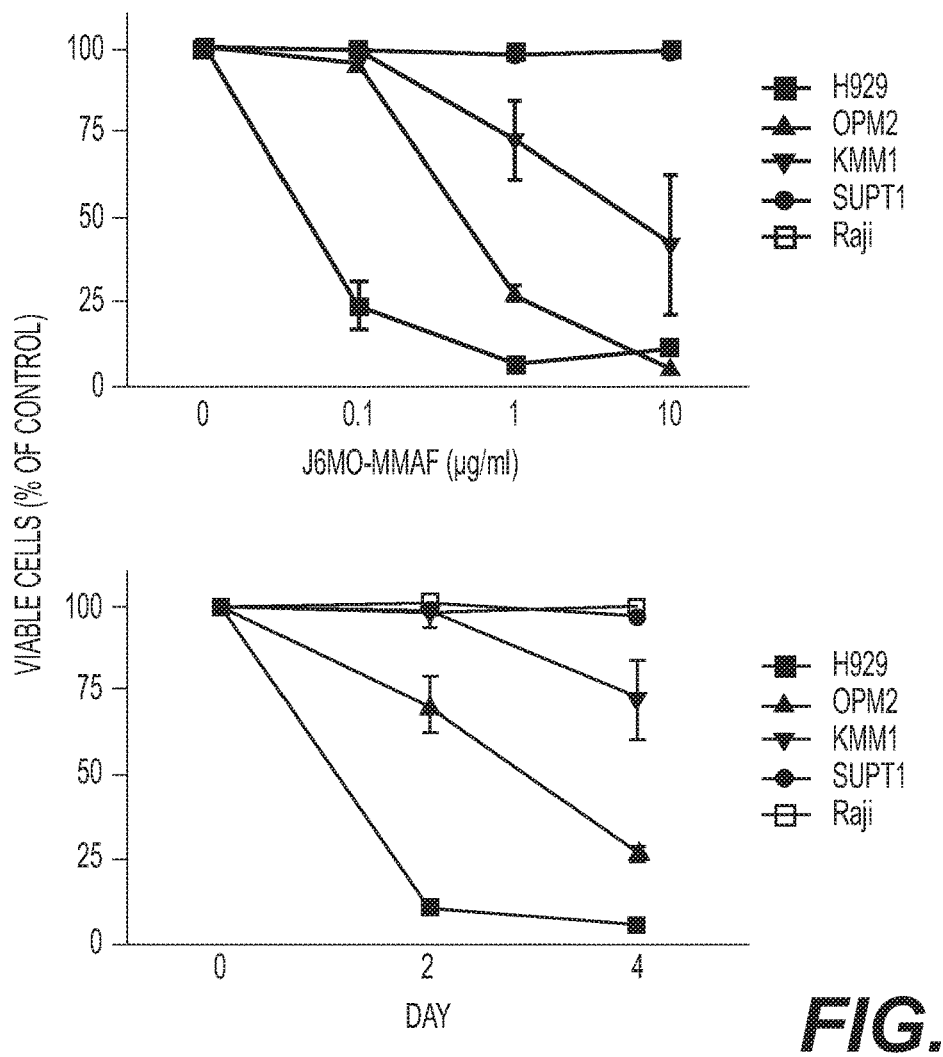
Figure 12C:
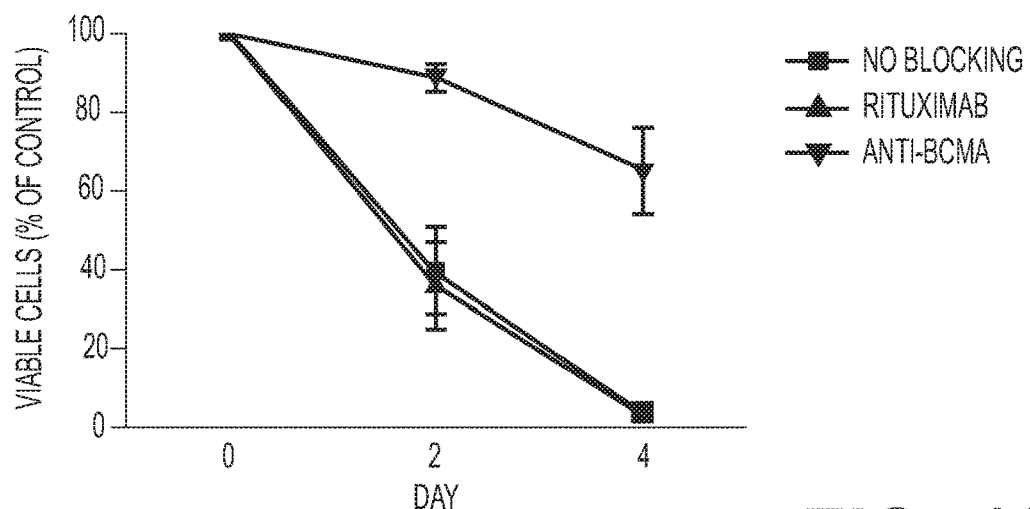
Figure 12D:
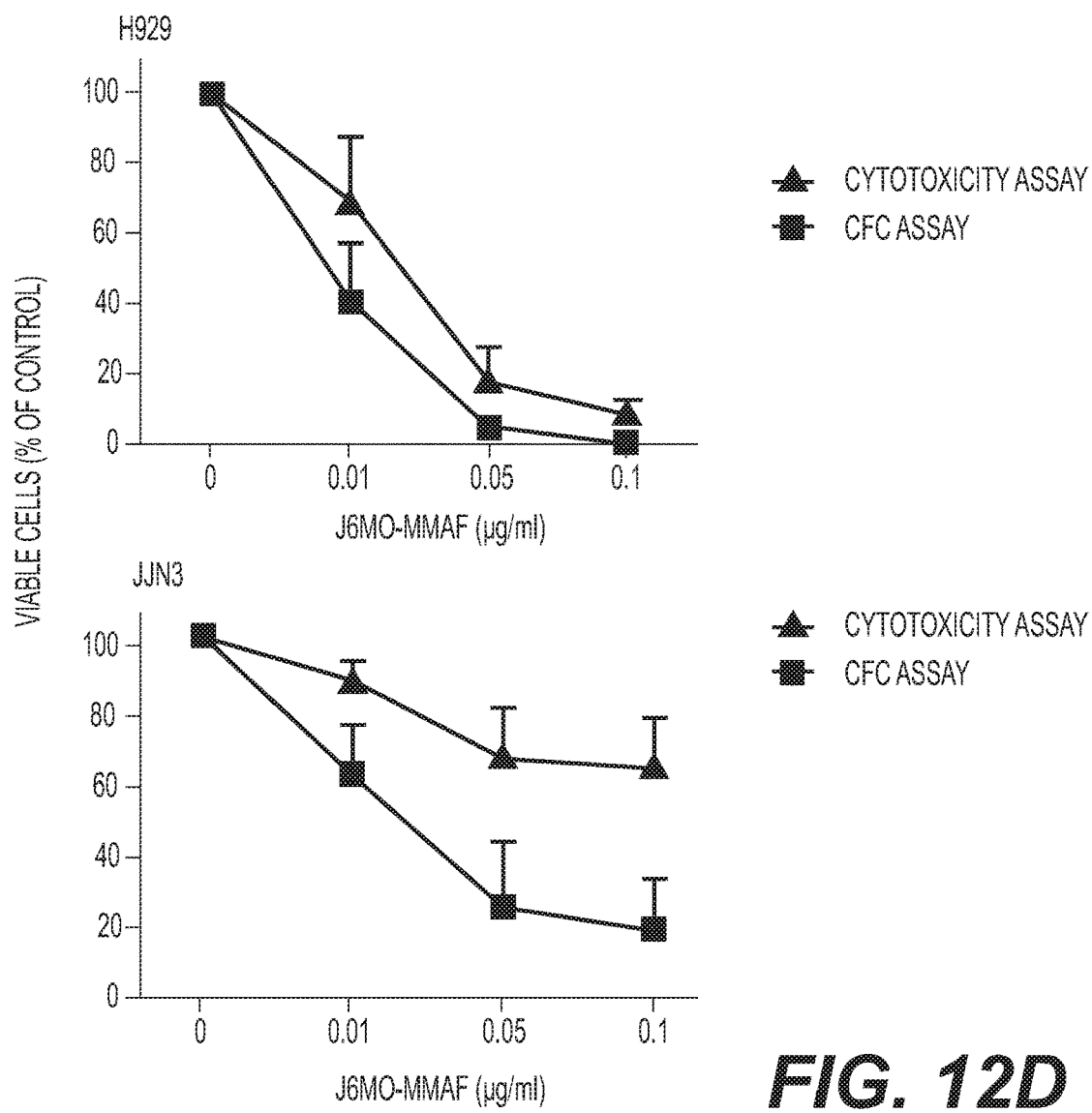

Next, J6M0-MMAF was tested on HMCL and non-MM cell lines. Cytotoxicity was time-dependent but also correlated with surface BCMA expression level, as revealed with modified ARH-77 cells transduced to express varying surface densities of BCMA (FIG. 12A). Thus, wild-type (WT) cells expressing negligible surface BCMA had little evidence of cell death, while the killing of transduced cells correlated with surface BCMA levels as indicated by inset FACS plots and MFI ratios. Non-MM cell lines do not express BCMA and were not affected by J6M0-MMAF, whilst HMCL showed evidence of cytotoxicity that was dose and time dependent. Thus, H929 cells expressing high levels of BCMA underwent rapid cell death (50%, by 24 hours, FIG. 13) at low concentrations of J6M0-MMAF (0.05 µg/ml), while longer incubation and higher doses of J6M0-MMAF are needed for equivalent cell kill with HMCL expressing lower BCMA levels (OPM2, KMM1, FIG. 12B). Killing was inhibited in the presence of S307118G03, but not anti-CD20 (FIG. 12C), indicating antigen specificity of this effect. In the HMCL JJN3, the progenitor population, as revealed by clonogenic assays, appeared to be more sensitive than the bulk population of cells (FIG. 12D). This cell line expresses low levels of BCMA, and maximal total cell kill achievable even after several days is around 40%. MM progenitors, however, appear to be more sensitive to J6M0-MMAF, as revealed by colony assays where up to 80% of clonogenic cells are killed at low J6M0-MMAF doses. A similar difference in sensitivity between bulk cells and clonogenic compartment is also seen in the H929 HMCL, although this is less marked, possibly due to higher levels of surface BCMA. The J6M0-MMAF has negligible effect on normal haemopoietic BM progenitors, as assessed in clonogenic assays.

Example 14—Cytotoxicity of J6M0-MMAF on Primary Myeloma Cells

Figure 14A:
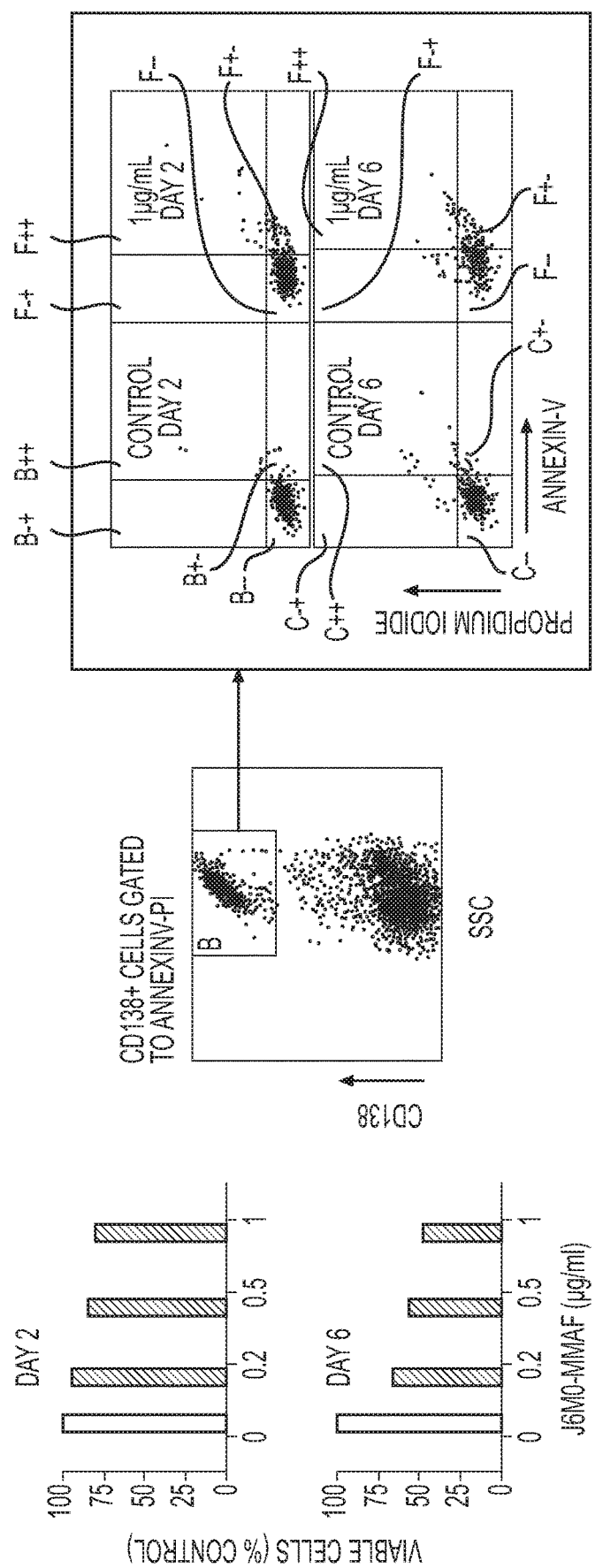
Figure 14B:
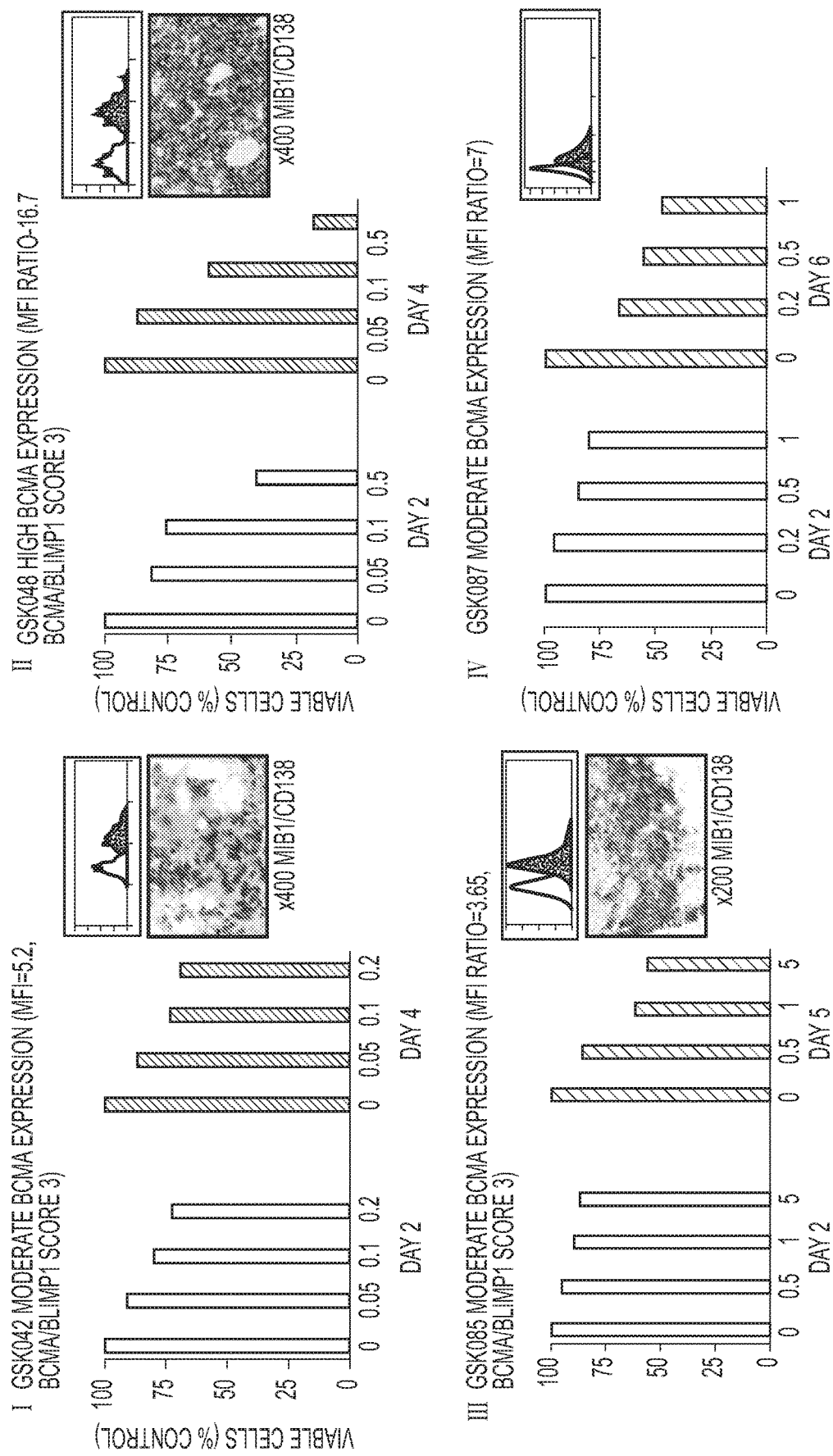

J6M0-MMAF mediated cytotoxicity on primary tumour cells from 13 patients was then assessed by incubating BM MNCs from patients with J6M0-MMAF at varying concentrations (0.02-10 µg/mL). To better represent in vivo conditions in the patient, all assays were carried out using whole BM MNCs, together with 20% MM patient plasma, which were previously demonstrated to improve CD138+ cell survival in vitro (Quinn et al., 2011). This assay format allowed cultures to be extended to up to 7 days with good recovery of primary tumour cells. MM plasma also contains soluble BCMA (Sanchez et al., 2012), allowing the assessment of J6M0-MMAF activity in this context. Target cell cytotoxicity at varying time points was then determined by CD138/PI/annexin V staining and flow cytometry (FIG. 14A). As expected, cytotoxicity of CD138+ MM cells was time dependent, but correlation was also seen with BCMA surface expression, and with proliferative level, as assessed by dual CD138/Ki67 staining using IHC. FIG. 14B shows results for four different patients: (i) in patient 042, whose tumour cells express moderate levels of surface BCMA but have a high proliferative fraction of >10%, significant tumour cell killing is seen at 0.2 µg/ml of J6M0-MMAF by day 4, (ii) on the other hand, tumour cells from patient 048 have a low proliferative fraction (<1%) but high levels of surface BCMA, resulting in nearly 80% killing by day 4 of culture with 0.5 µg/ml of J6M0-MMAF. For patient 085 (iii), whose tumour cells express moderate BCMA levels, and have a proliferative fraction of around 10%, significant killing (40-50%) is only seen at higher doses of J6M0-MMAF. No trephine sample for IHC was available from patient 087 (iv), however, significant killing is seen by day 6 in the context of moderate BCMA expression as seen on the FACS histogram. Cytotoxicity experiments were initially conducted with lower doses of J6M0-MMAF, and higher ranges were adopted with later experiments, hence the variation in doses shown. Data on 3 patients whose BM samples were incubated with the same range of J6M0-MMAF doses are shown in FIG. 15 which illustrates the time and dose-dependent effect of the J6M0-MMAF.

DISCUSSION

Curative strategies for MM are hampered by the toxicity of currently available classes of agent, co-morbidities of this elderly patient group, inherent genetic heterogeneity of the disease, and the changing dominance of multiple clones with each disease relapse. Thus, there is an urgent need for more specific targeting of the malignant PC, ideally utilising an antigen that is widely expressed on these cells, stably expressed throughout the disease, and using a strategy with minimal off-target toxicity. Monoclonal antibodies have emerged as the mainstay of therapy for other B-cell tumours, combining efficacy with good tolerability, especially in the elderly patients who do not benefit from multi-agent protocols (Rai, 2015). Many antigens previously and currently being targeted for MM are not specific for PC, e.g. CD38, CS1 (Chillemi et al., 2013; Veillette and Guo, 2013), thus careful consideration needs to be given regarding dosing and long term use, for example in maintenance. BCMA is almost exclusively expressed on PC, and may function in the survival and drug resistance of MM tumour cells.

The Examples described herein report the range of antigen expression on PC from patients at various stages of disease. The expression of BCMA on PC from virtually all bone marrow samples from patients with symptomatic MM, with both intra-cellular and surface expression, are reported. Expression levels vary among patients, with a trend towards higher levels in advanced disease, and in tumours with high risk genetic features. BCMA is expressed in extra-medullary tumours, suggesting once again a correlation with high risk disease and a role for the BCMA-APRIL axis in survival of MM cells outside the bone marrow. Indeed, APRIL-rich plasma cell niches have been postulated in several extra-medullary tissues (Huard et al., 2008). Importantly, patients whose tumour cells expressed moderate BCMA levels at diagnosis appear to retain expression through subsequent disease re-activation. Furthermore, residual tumour cells that persist during periods of disease stability following treatment, including high dose therapy, retain antigen expression, providing the rationale for maintenance strategies targeting BCMA. The reactivity of J6M0 with a range of normal tissues was examined, and the specificity of this antibody for PC was confirmed, with some binding of normal PC in tissues like the gastro-intestinal tract. Circulating BCMA levels are higher in MM patients compared with control subjects.

Rapid internalisation of the receptor following antibody binding was observed, with re-expression over 24 hours. Thus, tumour cells expressing low surface levels of BCMA, by re-expressing surface BCMA and binding more antibody, would likely also be sensitive to J6M0-MMAF mediated killing once sufficient cys-mcMMAF had accumulated within each cell. Antibody dependent cellular cytotoxicity via enhanced de-fucosylated Fc in J6M0 would also play a role but this may not be a major one in tumours with low surface BCMA.

The activity of J6M0-MMAF was studied against both immortalised cell lines and primary MM cells. As expected, dose and time dependent lysis of MM cell lines was seen, that was also dependent upon the surface expression of BCMA. Cell death occurred by apoptosis, as indicated by AnnexinV staining, and was BCMA specific, as it was blocked by a different anti-BCMA antibody, but not by anti-CD20 antibody. Notably, MM progenitors appear to be more sensitive to the effects of J6M0-MMAF, as observed in JJN3 MM cells, where progenitor cell cytotoxicity was greater at all doses tested, and reached greater maximal cell kill (80%), when compared with the bulk cell population. To assess the activity of J6M0-MMAF against primary MM cells, whole BM cultures were utilised, thus including autologous NK cells and monocytes/macrophages for ADCC. Additionally, MM patient plasma was used in place of FCS, as MM patient plasma has previously been found to better support MM cell survival and growth in vitro. In the context of these studies, MM plasma may contain soluble BCMA, thus would more closely approximate conditions in vivo. Very little cell kill was observed at 2 days, but there was increasing evidence of cytotoxicity at 4 days and beyond. These kinetics may reflect the slow proliferative rate of MM neoplasms, but may also lend support to the notion that receptor re-expression is required in order that intra-cellular concentrations of cys-mcMMAF reach toxic levels. Proliferative rate is also likely to influence J6M0-MMAF activity. Significant activity of J6M0-MMAF was demonstrated at relatively low concentrations (up to 0.2 µg/mL) in tumour cells with only moderate expression of BCMA, but a high proliferation rate.

An interesting observation was the shorter disease-free survival associated with a high BCMA/BLIMP1 score. Integration of BCMA expression score with genetic risk was able to identify a subgroup of patients with standard risk genetics who have inferior outcomes, suggesting that BCMA expression may impart additional prognostic information. Recent insights into the existence of multiple clones in MM patients, even from diagnosis, and the changing dominance of sub-clones, driven by drug exposure and the intrinsic genetic instability of the disease, underscore the challenges to effective therapy (Brioli et al., 2014).

Resistance to proteasome inhibitors and IMiDs, either at the level of the progenitor, or due to heterogeneity of biomarker expression, means that compounds with different modes of action that are independent of biologic or genetic risk, are urgently needed. Thus, antibody-based therapeutics are emerging as crucial players in this regard. BCMA is not only specific to PC, but is likely to play an indispensable role in MM cell survival, given its central place in PC physiology.

In summary, the instant inventors report the universal expression of BCMA in primary BM MM cells, with both intra-cellular and surface molecules that may represent continued recycling. The inventors confirm continued expression of BCMA throughout disease course, including in low level disease states post-ASCT. They also document an association with early relapse and the potential additional prognostic value of BCMA expression, when integrated with cytogenetic risk. These observations, together with the specificity of this antigen for PC, suggest BCMA to be an excellent target for novel therapies. The inventors also confirm the activity of a humanized anti-BCMA antibody with de-fucosylated Fc, conjugated to a microtubule-disrupting agent, against both MM cells lines and primary CD138+ MM cells. Features of J6M0-MMAF activity are consistent with its mode of action and suggest that both proliferative fraction and BCMA antigen level would be crucial biomarkers in phase 1 studies of this compound.

All publications, including, but not limited to, patents and patent applications, cited in this specification, are herein incorporated by reference as if each individual publication were specifically and individually indicated to be incorporated by reference herein as though fully set forth.

The above description fully discloses the invention, including preferred aspects thereof. Modifications and improvements of the aspects specifically disclosed herein are within the scope of the following claims. Without further elaboration, one skilled in the art can, using the preceding description, utilize the present invention to its fullest extent. Therefore, the Examples provided herein are to be construed as merely illustrative and are not a limitation of the scope of the present invention in any way.

```
Sequence listing

SEQ ID 1-CA8 CDRH1
NYWMH

SEQ ID 2-CA8 CDRH2
ATYRGHSDTYYNQKFKG

SEQ ID 3-CA8 CDRH3
GAIYDGYDVLDN

SEQ ID 4-CA8 CDRL1
SASQDISNYLN

SEQ ID 5-CA8 CDRL2
YTSNLHS

SEQ ID 6-CA8 CDRL3
QQYRKLPWT

SEQ ID 7-CA8 VH domain (murine)
EVQLQQSGAVLARPGASVKMSCKGSGYTFTNYWMHWVKQRPGQGLEWIGATYRGHS
DTYYNQKFKGKAKLTAVTSTSTAYMELSSLTNEDSAVYYCTRGAIYNGYDVLDNWGQG
TLVTVSS SEQ ID 8-CA8 VH domain (murine) (Polynucleotide)
GAGGTGCAGCTGCAGCAGAGCGGCGCCGTGCTGGCCAGGCCCGGAGCTAGCGTG
AAGATGAGCTGCAAGGGCAGCGGCTACACCTTCACCAACTACTGGATGCACTGGGT
GAAACAGAGGCCCGGCCAGGGACTGGAGTGGATCGGCGCCACCTACAGGGGCCA
CAGCGACACCTACTACAACCAGAAGTTCAAGGGCAAGGCCAAGCTGACCGCCGTGA
CCTCAACCAGCACCGCCTACATGGAACTGAGCAGCCTGACCAACGAGGACAGCGC
CGTCTATTACTGCACCAGGGGCGCCATCTACAACGGCTACGACGTGCTGGACAATT
GGGGCCAGGGAACACTAGTGACCGTGTCCAGC SEQ ID 9-CA8 VL domain (murine)
DIQLTQTTSSLSASLGDRVTISCSASQDISNYLNWYQQKPDGTVELVIYYTSNLHSGVPS
RFSGSGSGTDYSLTIGYLEPEDVATYYCQQYRKLPWTFGGGSKLEIKR SEQ ID 10-CA8 VL domain (murine) (Polynucleotide)
GATATCCAGCTGACCCAGACCACAAGCAGCCTGAGCGCCTCCCTGGGCGACAGGG
TGACCATTAGCTGCAGCGCCAGCCAGGACATCAGCAACTACCTGAACTGGTACCAG
CAGAAGCCCGACGGCACCGTGGAGCTCGTGATCTACTACACCTCCAACCTGCACAG
CGGCGTGCCCAGCAGGTTCTCTGGCAGCGGCAGCGGCACCGACTACAGCCTGACC
ATCGGCTATCTGGAGCCCGAGGACGTCGCCACCTACTACTGCCAGCAGTACAGGAA
GCTGCCCTGGACCTTCGGCGGAGGCTCTAAGCTGGAGATTAAGCGT SEQ ID 11-CA8 Humanised VH J6
QVQLVQSGAEVKKPGSSVKVSCKASGGTFSNYWMHWVRQAPGQGLEWMGATYRGH
SDTYYNQKFKGRVTITADKSTSTAYMELSSLRSEDTAVYYCARGAIYDGYDVLDNWGQ
GTLVTVSS
```

Sequence listing

SEQ ID 12-CA8 Humanised VH J6 (Polynucleotide)
CAGGTGCAGCTGGTCCAGAGCGGCGCCGAAGTGAAGAAGCCCGGCAGCTCCGTGA
AAGTGAGCTGCAAGGCCAGCGGCGGCACCTTCAGCAACTACTGGATGCACTGGGT
GAGGCAGGCCCCCGGACAGGGCCTGGAGTGGATGGGCGCCACCTACAGGGGCCA
CAGCGACACCCTACTACAACCAGAAGTTCAAGGGCCGGGTGACCATCACCGCCGACA
AGAGCACCAGCACCGCCTACATGGAACTGAGCAGCCTCAGGAGCGAGGACACCGC
TGTGTATTACTGCGCCAGGGGCGCCATCTACGACGGCTACGACGTGCTGGACAACT
GGGGCCAGGGCACACTAGTGACCGTGTCCAGC SEQ ID 13-CA8 Humanised VH J8
QVQLVQSGAEVKKPGSSVKVSCKASGYTFTNYWMHWVRQAPGQGLEWMGATYRGH
SDTYYNQKFKGRVTITADKSTSTAYMELSSLRSEDTAVYYCTRGAIYDGYDVLDNWGQG
TLVTVSS SEQ ID 14-CA8 Humanised VH J8 (Polynucleotide)
CAGGTGCAGCTGGTCCAGAGCGGCGCCGAAGTGAAGAAGCCCGGCAGCTCCGTGA
AAGTGAGCTGCAAGGCCAGCGGCTACACCTTCACCAACTACTGGATGCACTGGGTG
AGGCAGGCCCCCGGACAGGGCCTGGAGTGGATGGGCGCCACCTACAGGGGCCAC
AGCGACACCTACTACAACCAGAAGTTCAAGGGCCGGGTGACCATCACCGCCGACAA
GAGCACCAGCACCGCCTACATGGAACTGAGCAGCCTCAGGAGCGAGGACACCGCT
GTGTATTACTGCACCAGGGGCGCCATCTACGACGGCTACGACGTGCTGGACAACTG
GGGCCAGGGCACACTAGTGACCGTGTCCAGC SEQ ID 15-CA8 Humanised VH J9
QVQLVQSGAEVKKPGSSVKVSCKGSGYTFTNYWMHWVRQAPGQGLEWIGATYRGHS
DTYYNQKFKGRATLTADTSTSTAYMELSSLRSEDTAVYYCTRGAIYDGYDVLDNWGQG
TLVTVSS SEQ ID 16-CA8 Humanised VH J9 (Polynucleotide)
CAGGTGCAGCTGGTCCAGAGCGGCGCCGAAGTGAAGAAGCCCGGCAGCTCCGTGA
AAGTGAGCTGCAAGGGCAGCGGCTACACCTTCACCAACTACTGGATGCACTGGGTG
AGGCAGGCCCCCGGACAGGGCCTGGAGTGGATCGGCGCCACCTACAGGGGCCAC
AGCGACACCTACTACAACCAGAAGTTCAAGGGCCGGGCGACCCTCACCGCCGACA
CGAGCACCAGCACCGCCTACATGGAACTGAGCAGCCTCAGGAGCGAGGACACCGC
TGTGTATTACTGCACCAGGGGCGCCATCTACGACGGCTACGACGTGCTGGACAACT
GGGGCCAGGGCACACTAGTGACCGTGTCCAGC SEQ ID 17-CA8 Humanised VL M0
DIQMTQSPSSLSASVGDRVTITCSASQDISNYLNWYQQKPGKAPKLLIYYTSNLHSGVPS
RFSGSGSGTDFTLTISSLQPEDFATYYCQQYRKLPWTFGQGTKLEIKR SEQ ID 18-CA8 Humanised VL M0 (Polynucleotide)
GACATCCAGATGACCCAGAGCCCTAGCTCACTGAGCGCCAGCGTGGGCGACAGGG
TGACCATTACCTGCTCCGCCAGCCAGGACATCAGCAACTACCTGAACTGGTACCAG
CAGAAGCCCGGCAAGGCCCCCAAGCTGCTGATCTACTACACCTCCAACCTGCACTC
CGGCGTGCCCAGCAGGTTCAGCGGAAGCGGCAGCGGCACCGATTTCACCCTGACC
ATCTCCAGCCTGCAGCCCGAGGACTTCGCCACCTACTACTGCCAGCAGTACAGGAA
GCTCCCCTGGACTTTCGGCCAGGGCACCAAACTGGAGATCAAGCGT SEQ ID 19-CA8 Humanised VL M1
DIQMTQSPSSLSASVGDRVTITCSASQDISNYLNWYQQKPGKAPKLLIYYTSNLHSGVPS
RFSGSGSGTDYTLTISSLQPEDFATYYCQQYRKLPWTFGQGTKLEIKR SEQ ID 20-CA8 Humanised VL M1 (Polynucleotide)
GACATCCAGATGACCCAGAGCCCTAGCTCACTGAGCGCCAGCGTGGGCGACAGGG
TGACCATTACCTGCTCCGCCAGCCAGGACATCAGCAACTACCTGAACTGGTACCAG
CAGAAGCCCGGCAAGGCCCCCAAGCTGCTGATCTACTACACCTCCAACCTGCACTC
CGGCGTGCCCAGCAGGTTCAGCGGAAGCGGCAGCGGCACCGATTACACCCTGACC
ATCTCCAGCCTGCAGCCCGAGGACTTCGCCACCTACTACTGCCAGCAGTACAGGAA
GCTCCCCTGGACTTTCGGCCAGGGCACCAAACTGGAGATCAAGCGT

The invention claimed is:

1. A method for identifying and treating a subset of multiple myeloma patients with standard risk genetics, the method comprising:
    (a) detecting BCMA expression in BLIMP1+ plasma cells in samples from multiple myeloma patients with standard risk genetics;
    (b) identifying the patients with standard risk genetics having BCMA expression in greater than 60% of BLIMP1+ plasma cells as a subset having a poor prognosis, wherein the poor prognosis comprises an increase in risk for recurrence or relapse, decrease in likelihood of survival, decrease in time of survival, or an increase in risk of metastasis as compared to subjects having multiple myeloma with standard risk genetics and having BCMA expression in less than 60% of BLIMP1+ plasma cells; and
    (c) administering to the subset having the poor prognosis a multiple myeloma treatment regimen comprising a therapeutically effective amount of an antibody or a functional fragment thereof that binds to BCMA.

2. The method of claim 1, wherein the BCMA expression is determined using flow cytometry.

3. The method of claim 1, wherein the antibody or the functional fragment thereof comprises:
   i) CDRH1 as set out in SEQ ID NO: 1;
   ii) CDRH2 as set out in SEQ ID NO: 2;
   iii) CDRH3 as set out in SEQ ID NO: 3;
   iv) CDRL1 as set out in SEQ ID NO: 4;
   v) CDRL2 as set out in SEQ ID NO: 5; and
   vi) CDRL3 as set out in SEQ ID NO: 6.

4. The method of claim 3, wherein the antibody or the functional fragment thereof additionally comprises a cytotoxic agent.

5. The method of claim 4, wherein the cytotoxic agent is MMAE or MMAF.

6. The method of claim 1, wherein the antibody or the functional fragment thereof comprises a heavy chain variable region encoded by SEQ ID NO: 11 and a light chain variable region encoded by SEQ ID NO: 17.

7. The method of claim 1, wherein the multiple myeloma treatment regimen comprises a combination therapy.

8. The method of claim 1, wherein the antibody or the functional fragment thereof is administered in a repeated dosing regimen.

* * * * *

SEQUENCE LISTING

<160> NUMBER OF SEQ ID NOS: 20

<210> SEQ ID NO 1
<211> LENGTH: 5
<212> TYPE: PRT
<213> ORGANISM: Artificial Sequence
<220> FEATURE:
<223> OTHER INFORMATION: CA8 CDRH1

<400> SEQUENCE: 1

```
Asn Tyr Trp Met His
1               5

<210> SEQ ID NO 2
<211> LENGTH: 17
<212> TYPE: PRT
<213> ORGANISM: Artificial Sequence
<220> FEATURE:
<223> OTHER INFORMATION: CA8 CDRH2

<400> SEQUENCE: 2

Ala Thr Tyr Arg Gly His Ser Asp Thr Tyr Tyr Asn Gln Lys Phe Lys
1               5                   10                  15

Gly

<210> SEQ ID NO 3
<211> LENGTH: 12
<212> TYPE: PRT
<213> ORGANISM: Artificial Sequence
<220> FEATURE:
<223> OTHER INFORMATION: CA8 CDRH3

<400> SEQUENCE: 3

Gly Ala Ile Tyr Asp Gly Tyr Asp Val Leu Asp Asn
1               5                   10

<210> SEQ ID NO 4
<211> LENGTH: 11
<212> TYPE: PRT
<213> ORGANISM: Artificial Sequence
<220> FEATURE:
<223> OTHER INFORMATION: CA8 CDRL1

<400> SEQUENCE: 4

Ser Ala Ser Gln Asp Ile Ser Asn Tyr Leu Asn
1               5                   10

<210> SEQ ID NO 5
<211> LENGTH: 7
<212> TYPE: PRT
<213> ORGANISM: Artificial Sequence
<220> FEATURE:
<223> OTHER INFORMATION: CA8 CDRL2

<400> SEQUENCE: 5

Tyr Thr Ser Asn Leu His Ser
1               5

<210> SEQ ID NO 6
<211> LENGTH: 9
<212> TYPE: PRT
<213> ORGANISM: Artificial Sequence
<220> FEATURE:
<223> OTHER INFORMATION: CA8 CDRL3

<400> SEQUENCE: 6

Gln Gln Tyr Arg Lys Leu Pro Trp Thr
1               5

<210> SEQ ID NO 7
<211> LENGTH: 121
<212> TYPE: PRT
<213> ORGANISM: Artificial Sequence
<220> FEATURE:
<223> OTHER INFORMATION: CA8 VH domain (murine)
```

<400> SEQUENCE: 7

```
Glu Val Gln Leu Gln Gln Ser Gly Ala Val Leu Ala Arg Pro Gly Ala
1               5                   10                  15
Ser Val Lys Met Ser Cys Lys Gly Ser Gly Tyr Thr Phe Thr Asn Tyr
            20                  25                  30
Trp Met His Trp Val Lys Gln Arg Pro Gly Gln Gly Leu Glu Trp Ile
        35                  40                  45
Gly Ala Thr Tyr Arg Gly His Ser Asp Thr Tyr Tyr Asn Gln Lys Phe
    50                  55                  60
Lys Gly Lys Ala Lys Leu Thr Ala Val Thr Ser Thr Ser Thr Ala Tyr
65                  70                  75                  80
Met Glu Leu Ser Ser Leu Thr Asn Glu Asp Ser Ala Val Tyr Tyr Cys
                85                  90                  95
Thr Arg Gly Ala Ile Tyr Asn Gly Tyr Asp Val Leu Asp Asn Trp Gly
            100                 105                 110
Gln Gly Thr Leu Val Thr Val Ser Ser
        115                 120
```

<210> SEQ ID NO 8
<211> LENGTH: 363
<212> TYPE: DNA
<213> ORGANISM: Artificial Sequence
<220> FEATURE:
<223> OTHER INFORMATION: CA8 VH domain (murine) (Polynucleotide)

<400> SEQUENCE: 8

```
gaggtgcagc tgcagcagag cggcgccgtg ctggccaggc ccggagctag cgtgaagatg      60
agctgcaagg gcagcggcta ccttcacc aactactgga tgcactgggt gaaacagagg      120
cccggccagg gactggagtg gatcggcgcc acctacaggg gccacagcga cacctactac     180
aaccagaagt tcaagggcaa ggccaagctg accgccgtga cctcaaccag caccgcctac     240
atggaactga gcagcctgac caacgaggac agcgccgtct attactgcac caggggcgcc     300
atctacaacg gctacgacgt gctggacaat tggggccagg gaacactagt gaccgtgtcc     360
agc                                                                    363
```

<210> SEQ ID NO 9
<211> LENGTH: 108
<212> TYPE: PRT
<213> ORGANISM: Artificial Sequence
<220> FEATURE:
<223> OTHER INFORMATION: CA8 VL domain (murine)

<400> SEQUENCE: 9

```
Asp Ile Gln Leu Thr Gln Thr Thr Ser Ser Leu Ser Ala Ser Leu Gly
1               5                   10                  15
Asp Arg Val Thr Ile Ser Cys Ser Ala Ser Gln Asp Ile Ser Asn Tyr
            20                  25                  30
Leu Asn Trp Tyr Gln Gln Lys Pro Asp Gly Thr Val Glu Leu Val Ile
        35                  40                  45
Tyr Tyr Thr Ser Asn Leu His Ser Gly Val Pro Ser Arg Phe Ser Gly
    50                  55                  60
Ser Gly Ser Gly Thr Asp Tyr Ser Leu Thr Ile Gly Tyr Leu Glu Pro
65                  70                  75                  80
Glu Asp Val Ala Thr Tyr Tyr Cys Gln Gln Tyr Arg Lys Leu Pro Trp
                85                  90                  95
Thr Phe Gly Gly Gly Ser Lys Leu Glu Ile Lys Arg
```

<210> SEQ ID NO 10
<211> LENGTH: 324
<212> TYPE: DNA
<213> ORGANISM: Artificial Sequence
<220> FEATURE:
<223> OTHER INFORMATION: CA8 VL domain (murine) (Polynucleotide)

<400> SEQUENCE: 10

```
gatatccagc tgacccagac cacaagcagc ctgagcgcct ccctgggcga cagggtgacc      60
attagctgca gcgccagcca ggacatcagc aactacctga actggtacca gcagaagccc     120
gacggcaccg tggagctcgt gatctactac acctccaacc tgcacagcgg cgtgcccagc     180
aggttctctg gcagcggcag cggcaccgac tacagcctga ccatcggcta tctggagccc     240
gaggacgtcg ccacctacta ctgccagcag tacaggaagc tgccctggac cttcggcgga     300
ggctctaagc tggagattaa gcgt                                            324
```

<210> SEQ ID NO 11
<211> LENGTH: 121
<212> TYPE: PRT
<213> ORGANISM: Artificial Sequence
<220> FEATURE:
<223> OTHER INFORMATION: CA8 Humanised VH J6

<400> SEQUENCE: 11

```
Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Asn Tyr
            20                  25                  30
Trp Met His Trp Val Arg Gln Ala Pro Gly Gln Gly Leu Glu Trp Met
        35                  40                  45
Gly Ala Thr Tyr Arg Gly His Ser Asp Thr Tyr Tyr Asn Gln Lys Phe
    50                  55                  60
Lys Gly Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Gly Ala Ile Tyr Asp Gly Tyr Asp Val Leu Asp Asn Trp Gly
            100                 105                 110
Gln Gly Thr Leu Val Thr Val Ser Ser
        115                 120
```

<210> SEQ ID NO 12
<211> LENGTH: 363
<212> TYPE: DNA
<213> ORGANISM: Artificial Sequence
<220> FEATURE:
<223> OTHER INFORMATION: CA8 Humanised VH J6 (Polynucleotide)

<400> SEQUENCE: 12

```
caggtgcagc tggtccagag cggcgccgaa gtgaagaagc ccggcagctc cgtgaaagtg      60
agctgcaagg ccagcggcgg caccttcagc aactactgga tgcactgggt gaggcaggcc     120
cccggacagg gcctggagtg gatgggcgcc acctacaggg ccacagcga cacctactac      180
aaccagaagt tcaagggccg ggtgaccatc accgccgaca agagcaccag caccgcctac     240
atggaactga gcagcctcag gagcgaggac accgctgtgt attactgcgc caggggcgcc     300
atctacgacg gctacgacgt gctggacaac tggggccagg gcacactagt gaccgtgtcc     360
``` agc                                                                       363

<210> SEQ ID NO 13
<211> LENGTH: 121
<212> TYPE: PRT
<213> ORGANISM: Artificial Sequence
<220> FEATURE:
<223> OTHER INFORMATION: CA8 Humanised VH J8

<400> SEQUENCE: 13

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Ala Thr Tyr Arg Gly His Ser Asp Thr Tyr Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Ala Ile Tyr Asp Gly Tyr Asp Val Leu Asp Asn Trp Gly
            100                 105                 110

Gln Gly Thr Leu Val Thr Val Ser Ser
        115                 120

<210> SEQ ID NO 14
<211> LENGTH: 363
<212> TYPE: DNA
<213> ORGANISM: Artificial Sequence
<220> FEATURE:
<223> OTHER INFORMATION: CA8 Humanised VH J8 (Polynucleotide)

<400> SEQUENCE: 14
caggtgcagc tggtccagag cggcgccgaa gtgaagaagc ccggcagctc cgtgaaagtg      60
agctgcaagg ccagcggcta caccttcacc aactactgga tgcactgggt gaggcaggcc     120
cccggacagg gcctggagtg gatgggcgcc acctacaggg gccacagcga cacctactac     180
aaccagaagt tcaagggccg ggtgaccatc accgccgaca agagcaccag caccgcctac     240
atggaactga gcagcctcag gagcgaggac accgctgtgt attactgcac caggggcgcc     300
atctacgacg gctacgacgt gctggacaac tggggccagg gcacactagt gaccgtgtcc     360
agc                                                                    363

<210> SEQ ID NO 15
<211> LENGTH: 121
<212> TYPE: PRT
<213> ORGANISM: Artificial Sequence
<220> FEATURE:
<223> OTHER INFORMATION: CA8 Humanised VH J9

<400> SEQUENCE: 15

Gln Val Gln Leu Val Gln Ser Gly Ala Glu Val Lys Lys Pro Gly Ser
1               5                   10                  15

Ser Val Lys Val Ser Cys Lys Gly Ser Gly Tyr Thr Phe Thr Asn Tyr
            20                  25                  30

Trp Met His Trp Val Arg Gln Ala Pro Gly Gln Gly Leu Glu Trp Ile
        35                  40                  45

```
Gly Ala Thr Tyr Arg Gly His Ser Asp Thr Tyr Tyr Asn Gln Lys Phe
        50                  55                  60

Lys Gly Arg Ala Thr Leu Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Ala Ile Tyr Asp Gly Tyr Asp Val Leu Asp Asn Trp Gly
                100                 105                 110

Gln Gly Thr Leu Val Thr Val Ser Ser
            115                 120

<210> SEQ ID NO 16
<211> LENGTH: 363
<212> TYPE: DNA
<213> ORGANISM: Artificial Sequence
<220> FEATURE:
<223> OTHER INFORMATION: CA8 Humanised VH J9 (Polynucleotide)

<400> SEQUENCE: 16
caggtgcagc tggtccagag cggcgccgaa gtgaagaagc ccggcagctc cgtgaaagtg       60
agctgcaagg gcagcggcta caccttcacc aactactgga tgcactgggt gaggcaggcc      120
cccggacagg gcctggagtg gatcggcgcc acctacaggg ccacagcga cacctactac      180 aaccagaagt tcaagggccg ggcgaccctc accgccgaca cgagccagca caccgcctac      240
atggaactga gcagcctcag gagcgaggac accgctgtgt attactgcac caggggcgcc      300
atctacgacg gctacgacgt gctggacaac tggggccagg gcacactagt gaccgtgtcc      360
agc                                                                    363

<210> SEQ ID NO 17
<211> LENGTH: 108
<212> TYPE: PRT
<213> ORGANISM: Artificial Sequence
<220> FEATURE:
<223> OTHER INFORMATION: CA8 Humanised VL M0

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Asn Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Arg Lys Leu Pro Trp
                85                  90                  95

Thr Phe Gly Gln Gly Thr Lys Leu Glu Ile Lys Arg
            100                 105

<210> SEQ ID NO 18
<211> LENGTH: 324
<212> TYPE: DNA
<213> ORGANISM: Artificial Sequence
<220> FEATURE:
<223> OTHER INFORMATION: CA8 Humanised VL M0 (Polynucleotide)
```

-continued

```
<400> SEQUENCE: 18
gacatccaga tgacccagag ccctagctca ctgagcgcca gcgtgggcga cagggtgacc      60
attacctgct ccgccagcca ggacatcagc aactacctga actggtacca gcagaagccc     120
ggcaaggccc ccaagctgct gatctactac acctccaacc tgcactccgg cgtgcccagc     180
aggttcagcg gaagcggcag cggcaccgat ttcaccctga ccatctccag cctgcagccc     240
gaggacttcg ccacctacta ctgccagcag tacaggaagc tcccctggac tttcggccag     300
ggcaccaaac tggagatcaa gcgt                                             324

<210> SEQ ID NO 19
<211> LENGTH: 108
<212> TYPE: PRT
<213> ORGANISM: Artificial Sequence
<220> FEATURE:
<223> OTHER INFORMATION: CA8 Humanised VL M1

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Asn Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Arg Lys Leu Pro Trp
                85                  90                  95

Thr Phe Gly Gln Gly Thr Lys Leu Glu Ile Lys Arg
            100                 105

<210> SEQ ID NO 20
<211> LENGTH: 324
<212> TYPE: DNA
<213> ORGANISM: Artificial Sequence
<220> FEATURE:
<223> OTHER INFORMATION: 8 Humanised VL M1 (Polynucleotide)

<400> SEQUENCE: 20
gacatccaga tgacccagag ccctagctca ctgagcgcca gcgtgggcga cagggtgacc      60
attacctgct ccgccagcca ggacatcagc aactacctga actggtacca gcagaagccc     120
ggcaaggccc ccaagctgct gatctactac acctccaacc tgcactccgg cgtgcccagc     180
aggttcagcg gaagcggcag cggcaccgat tacaccctga ccatctccag cctgcagccc     240
gaggacttcg ccacctacta ctgccagcag tacaggaagc tcccctggac tttcggccag     300
ggcaccaaac tggagatcaa gcgt                                             324
```